US010508299B2

(12) United States Patent
Hansen et al.

(10) Patent No.: US 10,508,299 B2
(45) Date of Patent: *Dec. 17, 2019

(54) MICROFLUIDIC CELL TRAP AND ASSAY APPARATUS FOR HIGH-THROUGHPUT ANALYSIS

(71) Applicant: The University of British Columbia, Vancouver (CA)

(72) Inventors: Carl Lars Genghis Hansen, Vancouver (CA); Michael VanInsberghe, Vancouver (CA); Adam White, Toronto (CA); Oleh Petriv, Vancouver (CA); Tim Leaver, Vancouver (CA); Anupam Singhal, Mississauga (CA); William Bowden, Vancouver (CA); Veronique Lecault, Vancouver (CA); Dan Da Costa, Vancouver (CA); Leo Wu, Surrey (CA); Georgia Russell, Vancouver (CA); Darek Sikorski, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/793,681

(22) Filed: Oct. 25, 2017

(65) Prior Publication Data
US 2018/0230512 A1 Aug. 16, 2018

Related U.S. Application Data

(63) Continuation of application No. 14/122,653, filed as application No. PCT/CA2011/000612 on May 27, 2011, now Pat. No. 9,902,990.

(51) Int. Cl.
G01N 33/543 (2006.01)
C12Q 1/6806 (2018.01)
(Continued)

(52) U.S. Cl.
CPC ...... *C12Q 1/6806* (2013.01); *B01L 3/502753* (2013.01); *B01L 3/502761* (2013.01);
(Continued)

(58) Field of Classification Search
CPC ...... C12M 23/16; C12M 29/10; C12M 47/04; B01L 2400/086; G01N 33/5005; G01N 33/54366; G01N 1/4077
See application file for complete search history.

(56) References Cited

U.S. PATENT DOCUMENTS 7,144,616 B1 12/2006 Unger
7,452,726 B2 11/2008 Chou et al.
(Continued)

FOREIGN PATENT DOCUMENTS

CN 101285036 10/2008
CN 101550396 10/2009
(Continued)

OTHER PUBLICATIONS

Guo et al., (2011) "Deterministic ratchet based on the deformation of individual cells," Physical Review E 83:051910-5.
(Continued)

*Primary Examiner* — Betty J Forman
(74) *Attorney, Agent, or Firm* — Rudy J. Ng; Bozicevic, Field & Francis LLP

(57) ABSTRACT

Microfluidic devices are provided for trapping, isolating, and processing single cells. The microfluidic devices include a cell capture chamber having a cell funnel positioned within the cell capture chamber to direct a cell passing through the cell capture chamber towards one or more a cell traps positioned downstream of the funnel to receive a cell flowing. The devices may further include auxiliary chambers integrated with the cell capture chamber for subsequent processing and assaying of the contents of a captured cell.
(Continued)

Methods for cell capture and preparation are also provided that include flowing cells through a chamber, funneling the cells towards a cell trap, capturing a predefined number of the cells within the trap, interrupting the flow of cells, flowing a wash solution through the chamber to remove contaminants from the chamber, and sealing the predefined number of cells in the chamber.

22 Claims, 32 Drawing Sheets

Specification includes a Sequence Listing.

(51) Int. Cl.
| | |
|---|---|
| G01N 33/50 | (2006.01) |
| G01N 33/569 | (2006.01) |
| C12M 3/06 | (2006.01) |
| B01L 3/00 | (2006.01) |
| G01N 1/34 | (2006.01) |
| C12Q 1/6844 | (2018.01) |
| B01L 7/00 | (2006.01) |

(52) U.S. Cl.
CPC ............... *C12M 23/16* (2013.01); *G01N 1/34* (2013.01); *G01N 33/5005* (2013.01); *G01N 33/54366* (2013.01); *G01N 33/569* (2013.01); *B01L 7/52* (2013.01); *B01L 2200/0668* (2013.01); *B01L 2300/0816* (2013.01); *B01L 2400/086* (2013.01); *C12Q 1/6844* (2013.01)

(56) References Cited

U.S. PATENT DOCUMENTS

| | | | |
|---|---|---|---|
| 2002/0076825 | A1 | 6/2002 | Cheng et al. |
| 2003/0159932 | A1 | 8/2003 | Betts et al. |
| 2005/0106756 | A1 | 5/2005 | Blankenstein et al. |
| 2006/0160205 | A1 | 7/2006 | BlackBurn et al. |
| 2007/0151855 | A1 | 7/2007 | Schnelle et al. |
| 2008/0219894 | A1 | 9/2008 | Ganesan et al. |
| 2008/0302732 | A1 | 12/2008 | Soh et al. |
| 2009/0004730 | A1* | 1/2009 | Nitta .................. C12N 9/93 435/288.7 |
| 2009/0148937 | A1 | 6/2009 | Schnelle et al. |
| 2010/0055766 | A1 | 3/2010 | Hwang et al. |

FOREIGN PATENT DOCUMENTS

| | | |
|---|---|---|
| EP | 1371419 | 12/2003 |
| EP | 1531003 | 5/2005 |
| EP | 1883693 | 2/2008 |
| WO | WO 2010139295 | 12/2010 |

OTHER PUBLICATIONS

Adewumi et al., (2007) Characterization of human embryonic stem cell lines by the International Stem Cell Initiative, Nature Biotechnology, 25(7):803-816.
Bartel (2004) "MicroRNAs: Genomics, Biogenesis, Mechanism, and Function," Cell 116: 281-297.
Bengtsson et al., (2008) "Quantification of mRNA in single cells and modelling of RT-qPCR induced noise," BMC Molecular Biology 9:63 1-11.
Bontoux et al., (2008) "Integrating whole transcriptome assays on a lab-on-a-chip for single cell gene profiling," Lab on a Chip 8(3):443-450.
Braschler et al., (2005) "Gentle cell trapping and release on a microfluidic chip by in situ alginate hydrogel formation," Lab on a Chip 5: 553-559.
Calin et al., (2004) "MicroRNA profiling reveals distinct signatures in B cell chronic lymphocytic leukemias," Proc. Natl. Acad. Sci. U.S.A. 101: 11755-11760.
Chang, Johnston & Hobert (2003) "A transcriptional regulatory cascade that controls left/right asymmetry in chemosensory neurons of C. elegans," Genes & Development 17: 2123-2137.
Chen et al., (2005) "Real-time quantification of microRNAs by stem-loop RT-PCR," Nucl. Acids Res. 33(20), e179 1-9.
Chen et al., (2004) MicroRNAs Modulate Hematopoietic Lineage Differentiation. Science 303, 83-86.
Cohen et al., (2008) "Chemical Cytometry: Fluorescence-Based Single-Cell Analysis," Annual Review of Analytical Chemistry 1, 165-190.
Cui et al., (2007) "Retroviral insertional activation of the Fli-3 locus in erythroleukemias encoding a cluster of microRNAs that convert Epo-induced differentiation to proliferation," Blood 110(7): 2631-2640.
Dicarlo et al., (2006) "Single-Cell Enzyme Concentrations, Kinetics, and Inhibition Analysis Using High-Density Hydrodynamic Cell Isolation Arrays," Anal. Chem. 78: 4925-4930.
Diehn et al., (2009) "Association of reactive oxygen species levels and radioresistance in cancer stem cells," Nature 458(7239):780-783.
Emmert-Buck et al., (1996) "Laser Capture Microdissection," Science 274: 998-1001.
Gibsonet al., (1996) "A novel method for real time quantitative RT-PCR," Genome Research 6: 995-1001.
Ginzinger (2002) "Gene quantification using real-time quantitative PCR: An emerging technology hits the mainstream," Experimental Hematology 30: 503-512.
Guo et al., (2010) "Resolution of Cell Fate Decisions Revealed by Single-Cell Gene Expression Analysis from Zygote to Blastocyst," Developmental Cell 18(4):675-685.
Ikeda et al., (2007) "Altered microRNA expression in human heart disease." Physiol. Genomics 31, 367-373.
Kamme et al., (2003) "Single-Cell Microarray Analysis in Hippocampus CA1: Demonstration and Validation of Cellular Heterogeneity," J. Neurosci. 23(9) 3607-3615.
Kato et al., (2009) "Real-time functional imaging for monitoring miR-133 during myogenic differentiation." The International Journal of Biochemistry & Cell Biology 41(11): 2225-2231.
King et al., (2007) "A high-throughput microfluidic real-time gene expression living cell array," Lab on a Chip 7(1): 77-85.
Kloosterman et al., (2006) "In situ detection of miRNAs in animal embryos using LNA-modified oligonucleotide probes," Nat Meth 3(1) 27-29.
Kobel et al., (2010) "Optimization of microfluidic single cell trapping for long-term on-chip culture," Lab on a Chip 10: 857-863.
Krichevsky et al., (2003) "A micro RNA array reveals extensive regulation of microRNAs during brain development," RNA, 9: 1274-1281.
Landgraf et al., (2007) "A mammalian microRNA expression atlas based on small RNA library sequencing," Cell 129(7):1401-1414.
Larsson et al., (2010) "In situ detection and genotyping of individual mRNA molecules," Nature Methods 7(5): 395-U381.
Lee et al., (1993) "The C. elegans heterochronic gene lin-4 encodes small RNAs with antisense complementarity to lin-14," Cell 75: 843-854.
Li & Li (2005) "Microfluidic Selection and Retention of a Single Cardiac Myocyte, On-Chip Dye Loading, Cell Contraction by Chemical Stimulation, and Quantitative Fluorescent Analysis of Intracellular Calcium," Anal. Chem. 77: 4315-4322.
Li et al., (2004) "Transport, retention and fluorescent measurement of single biological cells studied in microfluidic chips," Lab on a Chip 4, 174-180.
Livak et al., (1995) "Oligonucleotides with fluorescent dyes at opposite ends provide a quenched probe system useful for detecting PCR product and nucleic acid hybridization," Genome Research 4: 357-362.
Livak (2008) "BioMark Dynamic Arrays for Single-Cell Gene Expression Analysis", Stem Cells Europe Conference, Poster 1045, Amsterdam, The Netherlands.

(56) References Cited

OTHER PUBLICATIONS

Lodish et al., (2004) "MicroRNAs Modulate Hematopoietic Lineage Differentiation," Science, 303(5654): 83-86.
Lozzio et al., (1981) "A multipotential leukemia cell line (K-562) of human origin(41106)," Proc Soc Exp Bioi Med, 166 (4):546-550.
Lu et al., (2005) "Micro RNA expression profiles classify human cancers," Nature 435: 834-838.
Lu & Tsourkas (2009) "Imaging individual microRNAs in single mammalian cells in situ," Nucleic Acids Research 37 (14): e100 1-10.
Ludwig et al., (2006) "Feeder-independent culture of human embryonic stem cells.," Nat Methods 3(8):637-646.
Marcus et al., (2006) "Microfluidic single-cell mRNA isolation and analysis," Anal Chem 78(9):3084-3089.
Marcy et al., (2007) "Dissecting biological "dark matter" with single-cell genetic analysis of rare and uncultivated TM7 microbes from the human mouth," Proc. Natl. Acad. Sci. U.S.A. 104(29): 11889-11894.
Miska et al., (2004) "Microarray analysis of microRNA expression in the developing mammalian brain," Genome Biology 5(9) R68. 1-R68-13.
Neely et al., (2006) "A single-molecule method for the quantitation of microRNA gene expression," Nat Meth 3(1): 41-46.
Nelson et al., (2004) "Microarray-based, high-throughput gene expression profiling of microRNAs," Nat Meth 1(2): 155-161.
Neuman et al., (1999) "Characterization of photo damage to *Escherichia coli* in optical traps," Biophys. J. 77: 2856-2863.
Niu et al. (2006) "Expression of artificial microRNAs in transgenic *Arabidopsis thaliana* confers virus resistance," Nat Biotech 24(11): 1420-1428.
Nolan et al., (2006) "Quantification of mRNA using real-time RT-PCR," Nat. Protocols I(3): 1559-15382.
O'Donnell et al., (2005) "c-Myc-regulated microRNAs modulate E2FI expression," Nature 435, 839-843.
Orba et al., (2003) "Application of laser capture microdissection to cytologic specimens for the detection of immunoglobulin heavy chain gene rearrangement in patients with malignant lymphoma," Cancer Cytopathology 99: 198-204.
Petriv et al., (2010) "Comprehensive microRNA expression profiling of the hematopoietic hierarchy," Proc Natl Acad Sci USA 107(35): 1-6.
Taylor et al., (2009) "Dynamic analysis of MAPK signaling using a high-throughput microfluidic single-cell imaging platform," PNAS, 106(10): 3758-3763.
Ramakrishnan et al. (2008) "Single-cell Gene Expression Analysis Using a Nanofluidic Platform", Advances in qPCR Conference, Poster 1020, Stockholm, Sweden.
Raj et al., (2008) "Imaging individual mRNA molecules using multiple singly labeled probes," Nature Methods 5 (10):877-879.
Riesebergel al., (2001) "Flow cytometry in biotechnology. Applied Microbiology and Biotechnology," 56: 350-360.
Rowat et al., (2009) "Tracking lineages of single cells in lines using a microfluidic device," Proceedings of the National Academy of Sciences 106: 18149-18154.
Scaria et al., (2006) "Host-virus interaction: a new role for microRNAs," Retrovirology 3(68): 1-9.
Schulze et al., (2010) "Assessing Differentiation Status of Human Embryonic Stem Cells Noninvasively Using Raman Microspectroscopy," Analytical Chemistry 82(12):5020-5027.
Shah et al., (2009) "Mutational evolution in a lobular breast tumour profiled at single nucleotide resolution," Nature 461(7265):809-813.
Sims & Allbritton (2007) "Analysis of single mammalian cells on-chip," Lab Chip 7(4):423-440.
Sindelka et al., (2008) "Intracellular expression profiles measured by real-time PCR tomography in the Xenopus laevis oocyte," Nucleic Acids Research 36(2): 387-392.
Skelley et al., (2009) "Microfluidic control of cell pairing and fusion," Nat Methods 6(2):147-152.
Stich et al., (2003) "Live Cell Catapulting and Recultivation," Pathology—Research and Practice, 199: 405-409.
Tang et al., (2006) "220-plex microRNA expression profile of a single cell," Nature Protocols 1, 1154-1159.
Tang et al., (2006) "MicroRNA expression profiling of single whole embryonic stem cells," Nucleic Acids Research 34(2) 1-7.
Tang et al., (2009) "mRNA-Seq whole-transcriptome analysis of a single cell," Nat Methods, 6(5):377-382.
Tang et al., (2010) "RNA-Seq analysis to capture the transcriptome landscape of a single cell," Nature Protocols 5(3):516-535.
Taniguchi et al., (2009) "Quantitative analysis of gene expression in a single cell by qPCR," Nature Methods, 6(7): 603-U550.
Thomson et al., (2004) "A custom microarray platform for analysis of microRNA gene expression," Nat Meth, 1(1): 1-7.
Thorsen et al., (2002) "Microfluidic large-scale integration," Science 298(5593):580-584 (2002).
Thum et al., (2008) "MicroRNAs: novel regulators in cardiac development and disease," Cardiovasc Res, 79: 562-570.
Thum et al., (2007) "MicroRNAs in the Human Heart: A Clue to Fetal Gene Reprogramming in Heart Failure," Circulation 116: 258-267.
Toriello NM, et al., Integrated microfluidic bioprocessor for single-cell gene expression analysis. Proc Natl Acad Sci USA, 105(51):20173-20178 (2008).
Unger et al., (2000) "Monolithic micro fabricated valves and pumps by multilayer soft lithography," Science, 288: 113-116.
Veening et al., (2006) "Single cell analysis of gene expression patterns of competence development and initiation of sporulation in Bacillus subtilis grown on chemically detined media," Journal of Applied Microbiology, 101: 531-541.
Voldman et al., (2002) "A microfabrication-based dynamic array cytometer," Anal. Chem. 74: 3984-3990.
Wang et al., (2009) "Role of microRNAs in cardiac hypertrophy and heart failure," IUBMB Life 61: 566-571.
Warren et al., (2006) "Transcription factor profiling in individual hematopoietic progenitors by digital RT-PCR," Proc Natl Acad Sci USA 103(47):17807-17812.
Wheeler et al., (2003) "Microfluidic device for single-cell analysis," Anal Chem 75(14):3581-3586.
Willenbrock et al., (2009) "Quantitative miRNA expression analysis: comparing microarrays with next-generation sequencing," RNA 15, 2028-2034.
Yuan et al., (2009) "MicroRNA-223 reversibly regulates erythroid and megakaryocytic differentiation of K562 cells," J Cell Mol Med 13(11-12): 4551-4559.
Zare & Kim (2010) "Microfluidic platforms for single-cell analysis," Annu Rev Biomed Eng, 12:187-201.
Zhang et al., (1992) "Whole genome amplification from a single cell: implications for genetic analysis," Proc. Natl. Acad. Sci. U.S.A 89: 5847-5851.
Zhong et al., (2008) "A microfluidic processor for gene expression profiling of single human embryonic stem cells," Lab Chip 8(1):68-74.
Chinese Office Action for Chinese Application No. 201180072343. 3, dated Sep. 26, 2014, 15 pages.

\* cited by examiner

Table 3. Results from sequencing barcoded cDNA produced on-chip. This method is intended to quantify transcript numbers rather than to obtain full gene sequences

| | Transcripts Mapped | Unique Molecules Sequenced | Most Abundant Transcript | 2nd Most Abundant Transcript | 3rd Most Abundant Transcript |
|---|---|---|---|---|---|
| Cell 1 | 1382 | 1909 | acetyl-Coenzyme A carboxylase beta (x49) | 18S ribosomal RNA (x25) | 28S ribosomal RNA (x14) |
| Cell 2 | 2041 | 3205 | acetyl-Coenzyme A carboxylase beta (x75) | 18S ribosomal RNA (x35) | multiple EGF-like-domains 8 (x30) |
| Cell 3 | 1566 | 2330 | 18S ribosomal RNA (x114) | 28S ribosomal RNA (x50) | acetyl-Coenzyme A carboxylase beta (x36) |
| Cell 4 | 2984 | 5159 | 18S ribosomal RNA (x172) | acetyl-Coenzyme A carboxylase beta (x110) | 28S ribosomal RNA (x57) |
| On-Chip Control | 31 | 36 | similar to oncomodulin (x3) | keratin 24 (x3) | acetyl-Coenzyme A carboxylase beta (x2) |
| PCR Control | 62 | 73 | zinc finger protein 182 (x12) | | |

FIG. 32

SEQUENCE LISTING

```
<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1
tgaaatgagg gcttgcgaag                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: Synthetic Sequence

<400> SEQUENCE: 2
aaatccgaag ccaggtgtcc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
atcacctcca ccacctggag                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
aggtccgagg atcaacccag                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 5
aggagggcct tggaagctta                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 6
aatcccccac acctcagagc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 7 atcccccac agaactcata                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 8
actagcccca ctccaacctg                                              20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 9
tcaggctgag aggtctccaa                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 10
agttgctctc caccccgact                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 11
ttctccttct ccagcttcac                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 12
ctcctccggg ttttgctcca                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 13
ttctgcagag ctttgatgtc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 14
cttggcaaat tgctcgagtt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 15
tgatcctctt ctgcttcagg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 16
atcggcctgt gtatatccca                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 17
aaatagaacc cccagggtga                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 18
tcgtttggct gaataccttc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 19
taagctgcag agcctcaaag                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 20
gcagcttaca catgttcttg                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 21
tccacccact tctgcagcaa                                               20

<210> SEQ ID NO 22
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 22
gattttcatt gttgtcagct                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 23
tctgctttgc atatctcctg                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 24
actggttcgc tttctctttc                                                   20

<210> SEQ ID NO 25
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 25
ttgcctctca ctcggttctc                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
ctgcaggaac aaattctcca                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
atctgctgca gtgtgggttt                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
```
atccttctcg agcccaagct                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 29
ttacagaacc acactcggac                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 30
tagtcgctgc ttgatcgctt                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
ctcaaaatcc tctcgttgtg                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 32
ctgagaaagg agacccagca                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
agaggaaagg acactggtcc                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 34
atagcctggg gtaccaaaat                                              20

<210> SEQ ID NO 35
<211> LENGTH: 20
<212> TYPE: DNA
<213> ORGANISM: Artificial Sequence

```
<220> FEATURE:
<223> OTHER INFORMATION: Synthetic Sequence

<400> SEQUENCE: 35
agtacagtgc agtgaagtga                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
ttccccctca gggaaaggga                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
tgacggagac agggggaaag                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
agtttgaatg catgggagag                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
attcctagaa gggcaggcac                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 40
ttttctttcc ctagctcctc                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 41
aaaaaccctg gcacaaactc                                               20
```

<210> SEQ ID NO 42
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 42
ccttagtgaa tgaagaactt                                                     20

<210> SEQ ID NO 43
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 43
accctttgtg ttcccaattc                                                     20

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
aaccagttgc cccaaactcc                                                     20

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
cattgaactt caccttccct                                                     20

<210> SEQ ID NO 46
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 46
gtgggattaa aatcaagagc                                                     20

<210> SEQ ID NO 47
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 47
ccaggcttct ttatttaaga                                                     20

<210> SEQ ID NO 48
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 48
aagtgtgtct atctactgtg                                      20

<210> SEQ ID NO 49
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 49
acccacactg cagcagatca                                      20

<210> SEQ ID NO 50
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 50
cacactcgga ccacatcctt ct                                   22

<210> SEQ ID NO 51
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 51
ccacatcgcc cagcagcttg g                                    21

<210> SEQ ID NO 52
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 52
ttgtgcatag tcgctgcttg at                                   22

<210> SEQ ID NO 53
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 53
aggccagcaa aaacaagg                                        18

<210> SEQ ID NO 54
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 54
caggccagca aaaagaa                                         17

<210> SEQ ID NO 55
```

-continued

```
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 55
ccagacatct ggaggctcat tg                                              22

<210> SEQ ID NO 56
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 56
tgaactagct gaggctggat a                                               21
```

MICROFLUIDIC CELL TRAP AND ASSAY APPARATUS FOR HIGH-THROUGHPUT ANALYSIS

BACKGROUND OF THE INVENTION

1. Field of Invention

This invention relates to microfluidic devices. In particular, the invention relates to microfluidic devices and their uses and methods for assaying cells.

2. Description of Related Art

Single cells represent a fundamental biological unit. However, the vast majority of biological knowledge has emerged as a consequence of studying cell populations and not individual cells. Inevitably, there are fundamental and applied questions, such as those relating to transcriptional control of stem cell differentiation, intrinsic noise in gene expression, and the origins of disease, that may only be addressed at the single cell level. For example, single cell analysis allows for the direct measurement of gene expression kinetics, or for the unambiguous identification of co-regulated genes, even in the presence of de-synchronization and heterogeneity that could obscure population-averaged measurements. Similarly, single cell methods are vital in stem cell research and cancer biology, where isolated populations of primary cells are heterogeneous due to limitations in purification protocols, and it is often a minority cell population that is the most relevant. High-throughput single cell measurement technologies are therefore of interest and have broad applications in clinical and research settings.

Existing methods for measuring transcript levels in single cells include RT-qPCR (1), single molecule counting using digital PCR (2) or hybridization probes (3, 4), and next generation sequencing (5). Of these, single cell RT-qPCR provides combined advantages of sensitivity, specificity, and dynamic range, but is limited by low throughput, high reagent cost, and difficulties in accurately measuring low abundance transcripts (6).

Microfluidic devices employing active valving to position and isolate cells have allowed for the isolation and genome amplification of individual microbial cells (32). Unfortunately, such devices do not allow for high throughput analysis due to the manual effort involved in operating the valving mechanisms. Moreover, the device does not allow isolated cells to be washed from the supernatant prior to treatment or analysis. This in turn allows for contamination events, and further limits the downstream applications of the device.

Accordingly, a goal of microfluidics research has been the development of integrated technology for scalable analysis of transcription in single cells. Microfluidic systems provide numerous advantages for single cell analysis: economies of scale, parallelization and automation, and increased sensitivity and precision that comes from small volume reactions. Considerable effort over the last decade has been directed towards developing integrated and scalable single cell genetic analysis on chip (7, 8). Thus, many of the basic functionalities for microfluidic single cell gene expression analysis have been demonstrated in isolation, including cell manipulation and trapping (9, 10), RNA purification and cDNA synthesis (11-13), and microfluidic qPCR (14) following off-chip cell isolation cDNA synthesis and preamplification. In particular, microfluidic qPCR devices (Biomark Dynamic Array, Fluidigm) have recently been applied to single cell studies (15, 16). Although these systems provide a high-throughput qPCR readout, they do not address the front end sample preparation and require single cell isolation by FACS or micropipette followed by off-chip processing and pre-amplification of starting template prior to analysis. The critical step of integrating all steps of single cell analysis into a robust system capable of performing measurements on large numbers of cells has yet to be reported. A single demonstration of an integrated device for directly measuring gene expression in single cells was described by Toriello et al., combining all steps of RNA capture, PCR amplification, and end-point detection of amplicons using integrated capillary electrophoresis (17). Despite the engineering complexity of this system, throughput was limited to four cells per run, cell capture required metabolic labeling of the cells, and the analysis was not quantitative.

Isolation of single or limited numbers of cells is required prior to many types of analysis and this typically requires the use of a cell trapping mechanism. Low trapping throughput and low trapping efficiency present a significant challenge to the goal of reliable and scalable analysis of single or small numbers of cells. Low capture efficiencies necessitating tens of thousands of cells in order to make a few single cell measurements is not an issue when using cell lines, however it becomes a significant problem when using primary samples of rare cell types, such as stem cells. Also, observations of both the trapped cells and those passing around the traps have indicated that the cell trapping efficiency was dependent on cell size, which could potentially introduce a bias into the single cell measurements.

SUMMARY OF THE INVENTION

The present invention is based in part on the discovery that an integrated microfluidic device may be used for high-throughput analysis of hundreds (thousands of single cells per experiment in a scalable, high performance, cost effective, and sensitive assay in pL to nL volumes (50 pL to 100 nL) as compared to assays in µL volumes. The description and examples provide the first implementation of robust and high-throughput single cell processing and amplification of nucleic acids on a chip, thereby achieving a major milestone in microfluidic biological analysis.

Microfluidic technologies capable of scalable and quantitative single cell genetic analysis are provided herein. Specifically, exemplified herein is an integrated microfluidic device for high-throughput RT-qPCR analysis of mRNA and miRNA expression at a throughput of hundreds to thousands of single cells per experiment. The description shows that this technology provides a powerful tool for scalable single cell gene expression measurements with improved performance, reduced cost, and higher sensitivity as compared to analysis in µL volumes.

The examples provided herein disclose a fully integrated microfluidic device capable of performing high-precision RT-qPCR measurements of gene expression from hundreds of single cells per run. Furthermore, embodiments of the device are capable of executing all steps of single cell processing including cell capture, cell lysis, reverse transcription, and quantitative PCR. In addition to higher throughput and reduced cost, it is shown herein that nanoliter volume processing reduced measurement noise, increased sensitivity, and provided single nucleotide specificity. The description shows an application of this technology to 3300 single cell measurements of i) miRNA expression in K562 cells, ii) co-regulation of a miRNA and one of its target transcripts during differentiation in embryonic stem cells, and iii) single nucleotide variant detection in primary lobular breast cancer cells. The core functionality established here provides the foundation from which a variety of on-chip single cell transcription analyses will be developed. Other aspects and features of the present invention will become apparent to those ordinarily skilled in the art upon review of the following description of specific embodiments of the invention in conjunction with the accompanying figures.

Alternatively, the types of cell processing and assaying may be selected from one or more of the following: rolling circle amplification, multiple displacement amplification, isothermal DNA and RNA amplifications, rapid amplification of cDNA ends (RACE), degenerate oligo primer PCR, mitochondrial DNA PCR; genomic PCR; digital PCR; RT-PCR; sequencing; immunochemistry; proximity ligation PCR, immuno PCR, metabolite analysis, enzymatic assays, reporter expression analysis; hybridization studies According to a first embodiment there is provided, a microfluidic device including: (a) a cell capture chamber, having at least one inlet and at least one outlet, wherein each inlet and outlet has an open and a closed position, whereby when the inlet is in the open position fluid is able to flow into the cell capture chamber and when the outlet is in the open position fluid is able to flow out of the cell capture chamber, and whereby when the inlet is in the closed position fluid is prevented from flowing into the cell capture chamber and when the outlet is in the closed position fluid is prevented from flowing out of the cell capture chamber, and wherein the direction of flow through the cell capture chamber dictates an upstream and a downstream orientation of the cell capture chamber; (b) a cell funnel positioned within the cell capture chamber and operable to direct a cell passing through the cell capture chamber towards one or more desired locations within the cell capture chamber; and (c) a cell trap, positioned generally downstream from the cell funnel, whereby the cell trap is positioned to receive a cell flowing downstream from the cell funnel.

The microfluidic device may further include: (a) a second inlet in fluid communication with a fluid injection channel, the upstream inlet having an open and a closed position, wherein the open position allows for fluid to enter the cell capture chamber from the fluid injection channel and in the closed position prevents fluid flow into the cell capture chamber from the fluid injection channel; and (b) a second outlet in fluid communication with one or more auxiliary chambers, the downstream outlet having an open and a closed position, wherein the open position allows for fluid to exit the cell capture chamber and enter the one or more auxiliary chambers and in the closed position prevents fluid flow into the one or more auxiliary chambers from the cell capture chamber.

The microfluidic device may further include a second inlet in fluid communication with a fluid injection channel, the second inlet having an open and a closed position, wherein the open position allows for fluid to enter the cell capture chamber from the fluid injection channel and in the closed position prevents fluid flow into the cell capture chamber from the fluid injection channel, and wherein the volume of the cell capture chamber is expandable.

The cell capture chamber may have one inlet and one outlet, wherein the inlet is in fluid communication with a fluid injection channel, and wherein the volume of the cell capture chamber is expandable.

The cell funnel may exert a force to direct cells towards the one or more desired locations within the cell capture chamber. The force exerted on the cells by the cell funnel may be selected from one or more of the following: a mechanical force; a gravitational force; an electromagnetic force; an electrostatic force; a magnetic force; an acoustic force; a hydrodynamic force; and an optical force. Furthermore, one or more of the above forces may contribute to directing cells to a desired location. For example, a physical structure may exert a mechanical force on a fluid, which in turn produces a hydrodynamic force. The force exerted on the cells by the cell funnel may be a hydrodynamic force.

The cell trap may be selected from one or more of the following: a mechanical trap; a hydrodynamic trap; a dielectrophoretic trap; a magnetic trap; an acoustic trap; an affinity trap; an optical trap; and a patch clamp trap. The cell trap may be a hydrodynamic trap.

The second outlet may be in fluid communication with a first auxiliary chamber. The first auxiliary chamber may be in fluid communication with a second auxiliary chamber, wherein there is a valve between the first and second auxiliary chambers, wherein the valve has an open position to allow fluid flow from the first auxiliary chamber to the second auxiliary chamber and a closed position to prevent fluid flow from the first auxiliary chamber to the second auxiliary chamber. The first auxiliary chamber may be in fluid communication with a second auxiliary chamber and the second auxiliary chamber is in fluid communication with a third auxiliary chamber, wherein there is a valve between the first and second auxiliary chambers, wherein the valve has an open position to allow fluid flow from the first auxiliary chamber to the second auxiliary chamber and a closed position to prevent fluid flow from the first auxiliary chamber to the second auxiliary chamber, wherein there is a valve between the second and third auxiliary chambers, wherein the valve has an open position to allow fluid flow from the second auxiliary chamber to the third auxiliary chamber and a closed position to prevent fluid flow from the second auxiliary chamber to the third auxiliary chamber.

The volume of the auxiliary chambers may be expandable. The volume of the cell capture chamber may be between 0.1 nL to 100.0 nL. The unexpanded volume of the expandable cell capture chamber may be between 0.1 nL to 100.0 nL. The volume of the cell capture chamber may be 0.6 nL. The unexpanded cell capture chamber may be 0.6 nL. The effective volume of a given chamber may be increased by expanding the initial chamber or by opening a valve to provide fluid flow into one or more auxiliary chambers. The ratio between the second auxiliary chamber and the first auxiliary chamber may be 5:1. The ratio between the second auxiliary chamber and the first auxiliary chamber may be at least 5:1. The ratio between the expanded cell capture chamber and the unexpanded cell capture chamber may be 5:1 or the ratio between the expanded first auxiliary chamber unexpanded first auxiliary chamber may be 5:1. The ratio between the expanded cell capture chamber and the unexpanded cell capture chamber may be at least 5:1 or the ratio between the expanded first auxiliary chamber unexpanded first auxiliary chamber may be at least 5:1. The ratio between the second auxiliary chamber and the first auxiliary chamber, or between the expanded cell capture chamber and the unexpanded cell capture chamber, or between the expanded first auxiliary chamber unexpanded first auxiliary chamber may vary depending on the reaction mixtures chosen, the concentrations of the components of the mixture and the concentration of the material being assayed. Alternatively, the cell capture chamber may be between 0.05 nL and 100.0 nL. Alternatively, the cell capture chamber may be between 0.05 nL and 90.0 nL.

Alternatively, the cell capture chamber may be between 0.1 nL and 95.0 nL. Alternatively, the cell capture chamber may be between 0.1 nL and 90.0 nL. Alternatively, the cell capture chamber may be between 0.1 nL and 85.0 nL. Alternatively, the cell capture chamber may be between 0.1 nL and 80.0 nL. Alternatively, the cell capture chamber may be between 0.1 nL and 75.0 nL. Alternatively, the cell capture chamber may be between 0.1 nL and 70.0 nL. Alternatively, the cell capture chamber may be between 0.1 nL and 65.0 nL. Alternatively, the cell capture chamber may be between 0.1 nL and 60.0 nL. Alternatively, the cell capture chamber may be between 0.1 nL and 55.0 nL. Alternatively, the cell capture chamber may be between 0.1 nL and 50.0 nL. Alternatively, the cell capture chamber may be between 0.1 nL and 45.0 nL. Alternatively, the cell capture chamber may be between 0.1 nL and 40.0 nL. Alternatively, the cell capture chamber may be between 0.1 nL and 35.0 nL. Alternatively, the cell capture chamber may be between 0.1 nL and 30.0 nL. Alternatively, the cell capture chamber may be between 0.1 nL and 25.0 nL. Alternatively, the cell capture chamber may be between 0.1 nL and 20.0 nL. Alternatively, the cell capture chamber may be between 0.1 nL and 15.0 nL. Alternatively, the cell capture chamber may be between 0.1 nL and 10.0 nL. Alternatively, the cell capture chamber may be between 0.1 nL and 9.0 nL. Alternatively, the cell capture chamber may be between 0.1 nL and 8.0 nL. Alternatively, the cell capture chamber may be between 0.1 nL and 7.0 nL. Alternatively, the cell capture chamber may be between 0.1 nL and 6.0 nL. Alternatively, the cell capture chamber may be between 0.1 nL and 5.0 nL. Alternatively, the cell capture chamber may be between 0.1 nL and 4.0 nL. Alternatively, the cell capture chamber may be between 0.1 nL and 3.0 nL. Alternatively, the cell capture chamber may be between 0.1 nL and 2.0 nL. Alternatively, the cell capture chamber may be between 0.1 nL and 1.0 nL.

The device may include between 1-10 cell traps and corresponding cell funnels. Alternatively, a funnel may be used in conjunction with more than one dedicated trap. The cell traps may also be designed to hold more than one cell each and each may be fed by one or more cell funnels. Additionally, cell traps may be sized such that they select for particular cell types if a mixed population of cells is being assayed. Furthermore, the cell traps and funnels may be designed to exclude certain cell types or to select certain cell types.

The cell funnel may include a pair of cell deflectors each having a proximal and a distal end, wherein the proximal ends are positioned at opposite sides of the capture chamber, and wherein each distal end of the cell deflector is angled on the diagonal in a downstream direction relative to the proximal ends, whereby the distal ends of the cell deflectors provide an opening sized to permit the passage of a cell between the distal ends of the cell deflectors. The cell trap may be generally cup or "U" shaped, or have a region that is generally cup or "U" shaped such that cells may enter the interior of the "U" shape from one side but not pass through. The cell trap may provide for fluid flow through the cell trap. The flow through of the trap may be before, during and after a cell is captured in the trap. Such flow through may assist with capturing the cell and with washing of a captured cell. Furthermore, the cell funnel or the cell trap may have a structure as shown in any one of FIG. 1, panels A-X, FIG. 2, panels A-E, FIG. 12, panels B-I, and FIG. 24.

According to a further embodiment there is provided, a cell capture and preparation method, the method including: (a) flowing cells in a fluid through a chamber; (b) funneling the cells in the fluid towards a cell trap; (c) capturing a predefined number of the cells within the chamber; (d) interrupting the flow of cells in the fluid; (e) washing the captured cells by flowing a wash solution through the chamber, wherein the flow of wash solution removes contaminants from the chamber; and (f) sealing the predefined number of cells in the chamber.

According to a further embodiment there is provided, a cell capture and preparation method, the method including: (a) flowing cells in a fluid through a chamber; (b) funneling the cells in the fluid towards a cell trap; (c) capturing a predefined number of the cells within the chamber; (d) interrupting the flow of cells in the fluid; (e) washing the captured cells by flowing a wash solution through the chamber, wherein the flow of wash solution removes contaminants from the chamber; and (f) sealing the predefined number of cells in the chamber.

The method may further include processing and assaying the washed captured cells, wherein assaying is selected from one or more of the following: rolling circle amplification, multiple displacement amplification, isothermal DNA and RNA amplifications, rapid amplification of cDNA ends (RACE), degenerate oligo primer PCR, mitochondrial DNA PCR; genomic PCR; digital PCR; RT-PCR; sequencing; immunochemistry; proximity ligation PCR, immuno PCR, metabolite analysis, enzymatic assays, reporter expression analysis; hybridization studies, etc.

The method may further include: (a) cell lysis; (b) reverse transcription; and (c) amplification.

The method may further include: (a) cell lysis; (b) reverse transcription; and (c) quantitative amplification.

According to a further embodiment there is provided, a cell assay method, the method including: (a) directing cells to a cell capture chamber, wherein the chamber has a volume of between 0.1 nL to 100 nL; (b) capturing a predefined number of the cells within the chamber; (c) washing the captured cells by flowing a wash solution through the chamber, wherein the flow of wash solution removes contaminants from the chamber; and (d) isolating the predefined number of cells in the chamber.

The method may further include assaying the washed captured cells, wherein assaying is selected from one or more of the following: rolling circle amplification, multiple displacement amplification, isothermal DNA and RNA amplifications, rapid amplification of cDNA ends (RACE), degenerate oligo primer PCR, mitochondrial DNA PCR; genomic PCR; digital PCR; RT-PCR; sequencing; immunochemistry; proximity ligation PCR, immuno PCR, metabolite analysis, enzymatic assays, reporter expression analysis; hybridization studies, etc.

The method may further include: (a) cell lysis; (b) reverse transcription; and (c) amplification.

The method may further include: (a) cell lysis; (b) reverse transcription; and (c) quantitative amplification.

According to a further embodiment there is provided, a cell assay method, the method including: (a) directing cells to a cell capture chamber, wherein the chamber has a volume of between 0.1 nL to 100 nL; (b) capturing a predefined number of the cells within the chamber; (c) washing the captured cells by flowing a wash solution through the chamber, wherein the flow of wash solution removes contaminants from the chamber; (d) isolating the predefined number of cells in the chamber; (e) lysing the cells within the chamber; (f) reverse transcribing the RNA released by the cell lysis; and (g) amplifying the cDNAs transcribed in (f) by polymerase chain reaction (PCR).

According to a further embodiment there is provided, a cell assay method, the method including: (a) directing cells to a cell capture chamber, wherein the chamber has a volume of between 0.1 nL to 100 nL; (b) capturing a predefined number of the cells within the chamber; (c) washing the captured cells by flowing a wash solution through the chamber, wherein the flow of wash solution removes contaminants from the chamber; (d) isolating the predefined number of cells in the chamber; (e) lysing the cells within the chamber; (f) reverse transcribing the RNA released by the cell lysis; and (g) amplifying the cDNAs transcribed in (f) by quantitative polymerase chain reaction (PCR).

According to a further embodiment there is provided, a cell capture and preparation method, the method including: (a) flowing cells in a fluid through a chamber; (b) funneling the cells in the fluid towards a cell trap; (c) capturing a predefined number of the cells within the chamber; (d) interrupting the flow of cells in the fluid; and (e) sealing the predefined number of cells in the chamber.

According to a further embodiment there is provided, a cell capture and preparation method, the method including: (a) flowing cells in a fluid through a chamber; (b) funneling the cells in the fluid towards a cell trap; (c) capturing a predefined number of the cells within the chamber; (d) interrupting the flow of cells in the fluid; and (e) sealing the predefined number of cells in the chamber.

According to a further embodiment there is provided, a cell assay method, the method including: (a) directing cells to a cell capture chamber, wherein the chamber has a volume of between 0.1 nL to 100 nL; (b) capturing a predefined number of the cells within the chamber; and (c) isolating the predefined number of cells in the chamber.

According to a further embodiment there is provided, a cell assay method, the method including: (a) directing cells to a cell capture chamber, wherein the chamber has a volume of between 0.1 nL to 100 nL; (b) capturing a predefined number of the cells within the chamber; (c) isolating the predefined number of cells in the chamber; (d) lysing the cells within the chamber; (e) reverse transcribing the RNA released by the cell lysis; and (f) amplifying the cDNAs transcribed in (e) by polymerase chain reaction (PCR).

According to a further embodiment there is provided, a cell assay method, the method including: (a) directing cells to a cell capture chamber, wherein the chamber has a volume of between 0.1 nL to 100 nL; (b) capturing a predefined number of the cells within the chamber; (c) isolating the predefined number of cells in the chamber; (d) lysing the cells within the chamber; (e) reverse transcribing the RNA released by the cell lysis; and (f) amplifying the cDNAs transcribed in (e) by quantitative polymerase chain reaction (PCR).

The method may further include a cell sorting step prior to directing the cells to a cell capture chamber. The method may further include immobilizing the captured cell prior to washing. Immobilization may further enhance washing of the cells in the capture chamber.

BRIEF DESCRIPTION OF THE DRAWINGS

In drawings which illustrate embodiments of the invention,

FIG. 1, panels M-X, are schematic drawings of cell cages according to various embodiments of the invention involving hydrodynamic cell traps.

FIG. 2, panel B, is a schematic drawing of a cell funnel and cell trap geometry according to one embodiment of the invention.

FIG. 2, panel C, is a schematic of a preferred cell funnel and cell trap geometry according to one embodiment of the invention.

FIG. 2, panel D, is optical micrograph of a single K562 approaching a trap with the geometry presented in FIG. 2, panel C.

FIG. 2, panel E, is optical micrograph of the K562 in FIG. 2, panel C, after being trapped.

FIG. 12, panel B, is an optical micrograph of the array unit corresponding to the area within the black rectangle in FIG. 12, panel A.

FIG. 12, panel C, is an optical micrograph of two cell capture chambers with trapped single cells.

FIG. 12, panel D, is schematic drawing of a single cell suspension injected into the device depicted in FIG. 12, panel A.

FIG. 12, panel E, is schematic drawing of a cell trap isolating a single cell from the fluid stream to permit washing of the cell.

FIG. 12, panel F, is schematic drawing of actuation of pneumatic valves to result in single cell isolation prior to heat lysis.

FIG. 12, panel G, is schematic drawing of injection of reagent for reverse transcription (RT) reaction.

FIG. 12, panel H, is schematic drawing of the reagent injection line being flushed with subsequent reagent for PCR.

FIG. 12, panel I, is schematic drawing of reagent for qPCR being combined with RT product in a 50 nL qPCR chamber.

FIG. 13, panel B, is a graph of 300 real time amplification curves generated from processing sequences of images similar to that in FIG. 12, panel A.

FIG. 13, panel C, is a graph of on-chip and off-chip RT-qPCR for GAPDH from a 8× serial dilution of purified total RNA.

FIG. 13, panel D, is a graph depicting the real-time amplification curves of GAPDH in K562 cell lysate dilutions.

FIG. 13, panel E, is a graph depicting the measured CT values for GAPDH in dilution series of cell lysate.

FIG. 15, panel B, is a scatter plot showing CT measurements for experiment shown in FIG. 15, panel A.

FIG. 15, panel C, is a histogram of the number of GAPDH transcripts measured in single K562 cells (N=233).

FIG. 16, panel B, is a histogram showing the size distribution of cells isolated by microfluidic traps.

FIG. 17, panel B, is a scatterplot of GAPDH measurements in cells washed in PBS on-chip prior to injection into microfluidic device.

FIG. 17, panel C, is a graph of GAPDH measurements from loading purified RNA and washing, or not washing, the cell capture chambers.

FIG. 18, panel B, is a fluorescence image of entire device, corresponding to experiment in FIG. 18, panel A,) after 30 PCR cycles.

FIG. 20, panel B, is a histogram of differential expression of miR-223 between K562 cells and hESCs.

FIG. 20, panel C, is a graph of mean single cell miRNA copy numbers measured by RT-qPCR in a microfluidic device according to one embodiment of the invention compared to digital PCR measurements from bulk cell lysate.

FIG. 20, panel D, is a histogram of differential expression of miR-223 between K562 cells and hESCs.

FIG. 21, panels B and C, are histograms showing the distribution of miR-145 and OCT4 transcripts.

FIG. 21, panel D, is a scatterplot showing co-expression measurements of SP1 wild-type and SNV mutant transcripts in primary cells isolated from a lobular breast cancer sample.

FIG. 22, panel B, is a representative image of undifferentiated CA1S cells.

FIG. 25, panel B, is an image illustrating the stacking of functionalized beads in a chamber according to one embodiment of the invention.

FIG. 32 is Table 3: Results from sequencing barcoded cDNA produced on-chip.

DETAILED DESCRIPTION

Figure 1:
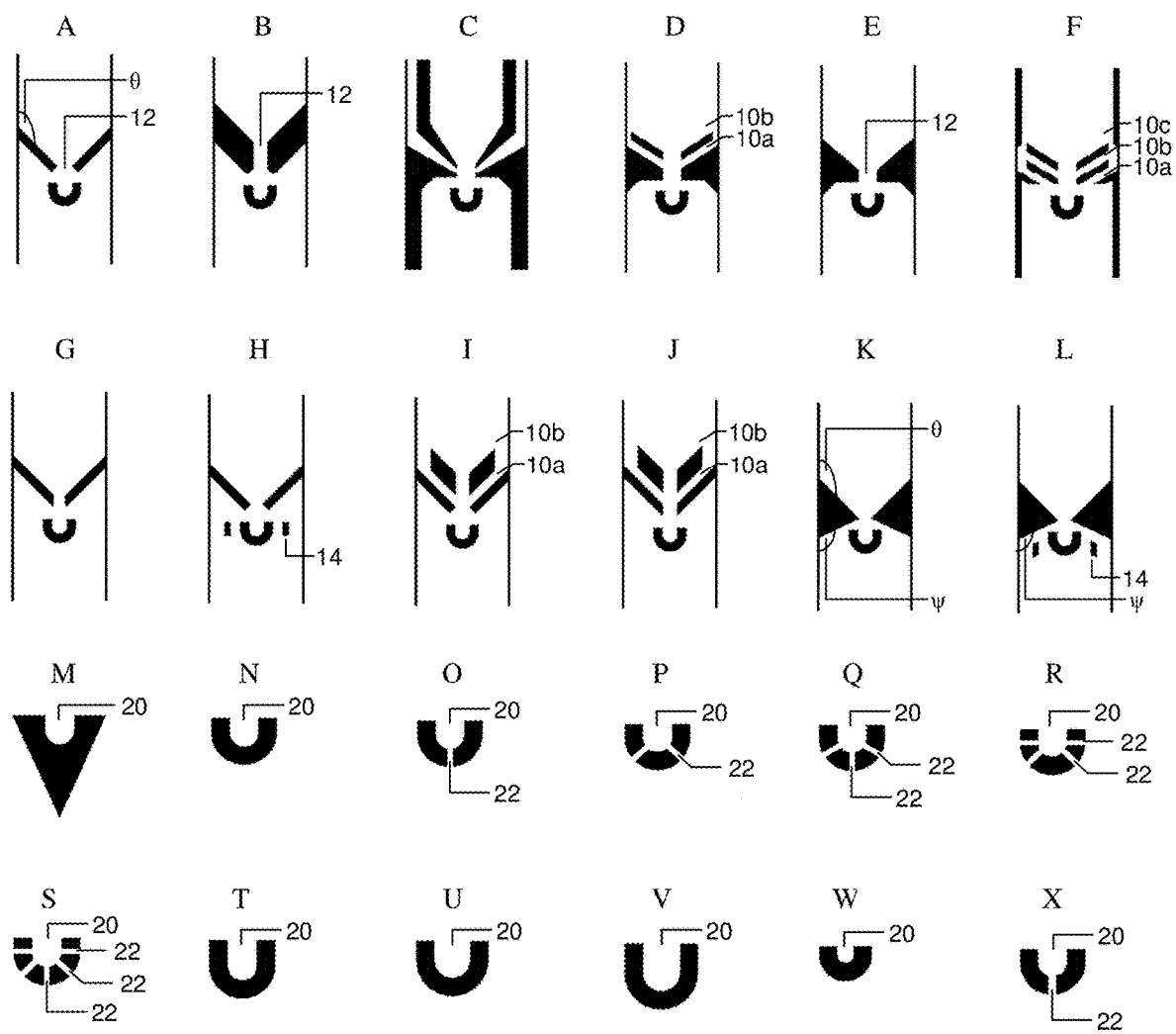
FIG. 1, panels A-L, are schematic drawings of a cell funnel and corresponding cell cages according to various embodiments of the invention involving hydrodynamic cell traps.

A variety of techniques have been developed in order to isolate and measure single cells. These techniques all greatly differ in both the number of cells they are able to analyze and the number of parallel, or multiplexed, measurements they are able to perform.

Definitions

"Flow cytometry", as used herein, is a widespread technique for rapidly and quantitatively examining and sorting populations of cells, organelles and other constituents based on single particle measurements of fluorescence, light scattering and optical absorbance (18). Flow cytometry is able to process and measure up to hundreds of thousands of cells per minute, using optical multiplexing to measure different attributes. This technique has been used to measure both physical properties and chemical composition of single cells (19). Measuring both mRNA (20) and miRNA (21) expression using flow cytometry has been performed by coupling transcriptional reporters such as GFP to genes or miRNA of interest and recording the fluorescence of each cell. Sorting single cells via flow cytometry for further genetic analysis via RT-qPCR has also been previously reported (22).

"Laser capture microdissection" (LCM), a used herein, is a technique in which pure populations from heterogeneous samples under direct visualization can be isolated for further analysis (23). This technique can be used on tissues (23), cytological preparations (24) and live cell culture (25). In LCM, cells of interest are visualized under a microscope and the user selects which regions to isolate from the rest of the sample. These selected regions can then be isolated from the rest of the sample by either ablating the surrounding regions, or cutting out the desired sections from the sample. Because this method is non-destructive to the samples being isolated, cells isolated via this method can be measured using any traditional molecular biology techniques.

A "microfluidic device", as used herein, refers to any device that allows for the precise control and manipulation of fluids that are geometrically constrained to structures in which at least one dimension (width, length, height) is less than 1 mm.

A "cell capture chamber", as used herein, refers to an enclosed space within a microfluidic device in which one or more cells may be isolated from a larger population of cells as the cells are flowed through the device. Each cell capture chamber will have at least one inlet for permitting fluid, including fluid containing cells, to enter the chamber, and at least one outlet to permit fluid to exit the chamber. Persons skilled in the art will understand that an inlet or an outlet can vary considerably in terms of structure and dimension, and may be characterized in a most general sense as an aperture that can be reversibly switched between an open position, to permit fluid to flow into or out of the cell capture chamber, and a closed position to seal the cell capture chamber and thereby isolate and retain its contents, whereby the aperture may also be intermediate between the open and closed positions to allow some fluid flow.

The direction of fluid flow through the cell capture chamber dictates an "upstream" and a "downstream" orientation of the cell capture chamber. Accordingly, an inlet will be located at an upstream position of the chamber, and an outlet will be generally located at a downstream position of the chamber. A person skilled in the art will understand, however, that a single aperture could function as both an inlet and an outlet.

An "inlet" or an "outlet", as used herein, may include any or an aperture whereby fluid flow is restricted through the inlet, outlet or aperture. There may be a valve to control flow, or flow may be controlled by separating the channels with a layer which prevents flow (for example, oil).

A "cell capture chamber", may further include a "cell trap" positioned generally downstream from the "cell funnel", whereby the cell trap is positioned to receive (and retain) a cell flowing downstream from the cell funnel.

A "cell funnel", as used herein, refers to an apparatus which is designed to focus the flow of cells from an upstream location, where the cells are dispersed, to one or more desired downstream locations within the cell capture chamber having a smaller cross sectional area of cell flow. The cell funnel exerts a force to direct cells towards the one or more desired locations within the cell capture chamber. For the purposes of clarity, "force" is defined herein as any influence that causes a free body (e.g. a cell) to undergo a change in velocity. Funnels may either span the entire height and/or width of the cell capture chamber, or partially span the height and/or width.

FIG. 1, panels A-L, provides illustrations of exemplary mechanical funnels according to various embodiments of the invention. The basic mechanical funnel 10 of FIG. 1, panel A, can be modified by making a constriction 12 longer as in FIG. 1, panels B and E. There may be multiple funnels, such as the nested funnels 10a and 10b in FIG. 1, panels D, I and J, and 10c in FIG. 1, panel F. The angle θ of the funnels may be varied as exemplified in FIG. 1, panel K. The constriction 12 of the funnel may be straight as in FIG. 1, panels D, E, F, G, K, or angled as in FIG. 1, panels A, B, H, I, J, K, L. Funneling may be additionally accomplished through a combination of mechanical and hydrodynamic means as in FIG. 1, panel C (i.e. a different fluid, or the same fluid at a different flow rate, may flow in through the outside channels). A funnel may also comprise a change in the cross-section of the upstream channel, such as a groove, that causes cells to be positioned at a specified section along the width of the channel prior to encountering the cell trap.

A "cell trap", as used herein, refers generally to a means for receiving and retaining cells at a pre-determined location over time. A cell trap may comprise localized surface modifications for chemical immobilization of a cell. Alternatively, the cell trap may be a mechanical trap, a hydrodynamic trap (10, 26-28), a hydrodynamic balancing trap (29, 30), an active valving trap (2, 10, 31, 32), a dielectrophoretic trap (33), a DNA immobilization trap (17), a gel encapsulation trap (34), a magnetic trap, an acoustic trap or an optical trap (35). In various embodiments of the current invention, a cell trap will generally be positioned directly in the path of the smaller cross sectional of cell flow created by the funnel. Where a mechanical funnel as illustrated in FIG. 1 is used according to various embodiments of the invention, a trap may be positioned directly after the downstream opening of the funnel.

A "mechanical trap", as used herein, refers to a physical cell trap such as a cage.

A "hydrodynamic trap", as used herein, refers to a cell trap in which the force of the fluid in motion plays a role in retaining a trapped cell in its position. A hydrodynamic trap may be also be comprised of a mechanical trap in which a cell is captured and retained. In certain embodiments of the invention utilizing hydrodynamic traps, it may be desirable to have three or more inlets to the cell capture chamber so that the flows may be adjusted in order to direct cells to the traps.

A "dielectrophoretic trap", as used herein, refers to a cell trap in which cells, being dielectric objects, are retained by the forces generated by a non-uniform electric field.

A "magnetic trap", as used herein, refers to a cell trap employing magnetic fields to retain cells. Typically, cells will be labeled with magnetic particles, and then positioned and retained by the magnetic fields. However, magnetic traps can also be used to trap-non-magnetic cells in suitable buffers.

An "acoustic trap", as used herein, refers to a cell trap in which ultrasonic standing waves are used to generate stationary pressure gradients that exert forces that position and retain cells.

An "optical trap", as used herein, refers to a cell trap in which a tightly focused laser beam, typically a near-infra red laser beam, is used to draw cells in the direction of the beam.

The size of the cell trap may be varied according to the size, type, mechanical properties, or number of cells that is desired to be trapped. A microfluidic device according to various embodiments of the invention may further include a combination of trap designs for the capture of a range of cell types. Furthermore, each cell capture chamber could include multiple traps. In such embodiments, the frequency of cells of that are trapped at each size could be used as a diagnostic. Alternatively, the contents of a group of cells caught in a single trap could be processed and analyzed.

FIG. 1, panels M-X, provides illustrations of exemplary physical cages used in hydrodynamic traps according to various embodiments of the invention. The inner shape of the cages may be cup-shaped, as are the cages 20 in FIG. 1, panels M-X, to accommodate spherical-shaped cells, or may be designed with various geometries to accommodate cells of unique shape and/or size. The cages may form weirs that span essentially the entire height or width of the chamber, or partially span the height or width of the chamber, or both.

The outer shape of the cage may be changed to modulate fluid flow around the trap as in FIG. 1, panel M. Perforations or sieve elements 22 can be added as in FIG. 1, panels O, P, Q, R, S, and X, to facilitate and modulate fluid flow through the cup. The perforation size may be decreased or increased as in FIG. 1, panel X. The perforations may either be the entire height or width of the chamber, or partially span the height or width of the chamber, or both. The size of the cage can be made longer as in FIG. 1, panel T, wider as in FIG. 1, panel U, longer and wider as in FIG. 1, panel V, or shorter and narrower as in FIG. 1, panel W.

The physical structures forming the funnel may be angled on both sides, i.e. also on the side opposite the funneling surface, to facilitate removing cells from the trap, as with angles $\psi$ in FIG. 1, panels K and L. Further features, in addition to the trap, may be located downstream of a funnel to further modulate the fluidic impedance, such as elements 14 in FIG. 1, panels H and L.

A "fluid injection channel", as used herein, refers to any conduit through which fluid may be introduced into a chamber of the device. A fluid injection channel can be used to deliver any fluid to a chamber including cell suspensions, wash buffers, reaction mixes, etc.

An "auxiliary chamber", as used herein, refers to any chamber subsidiary to a cell capture chamber. Auxiliary chamber can be used for treatment or assaying of a captured cell, or its isolated contents. Treatment can include cell preparation steps including culture, washing, lysis, and fractionation. Assaying may include DNA and RNA amplification and detection, including mitochondrial PCR; genomic PCR; digital PCR, RT-PCR, RTq-PCR, multiple displacement amplification (DNA), rolling circle amplification sequencing, degenerate PCR, molecular inversion probes, molecular beacons, as well as other DNA/RNA amplification and detection methods, in vitro transcription, ligation, immunochemistry; reporter expression analysis; hybridization studies; and so forth. Several auxiliary chambers may be connected, in tandem and/or in parallel, to a single cell capture chamber, such that multiple treatments may be performed on the contents of a single cell capture chamber. A valve may be positioned between an auxiliary chamber and the cell capture chamber, or between auxiliary chambers, to regulated fluid flow between chambers.

An "expandable" cell capture chamber, as used herein, refers to a cell capture chamber that may be expanded, or contracted, during operation to accommodate different fluid volumes. As such, a single chamber can be used for the purposes of cell capture and subsequent treatment and analysis that must be conducted in different fluid volumes, and thereby avoid the need for multiple discrete chambers.

Expansion of an expandable cell capture chamber may be effected in several ways. For example, the chamber may comprise a syringe in which chamber volume is modulated by use of a plunger. Alternatively, the chamber may be constructed of resilient materials that can expand with the addition of fluid, or contract when the fluid volume is released. Yet alternatively, the chamber may be partially defined by an immiscible liquid (such as air or oil), such that a greater fluid volume may be accommodated by movement of the liquid boundary.

A person skilled in the art will understand that an auxiliary chamber may be expandable. Accordingly, a microfluidic device may be comprised of a combination of non-expandable and/or expandable cell capture chambers and auxiliary chambers.

"Contaminants", as used herein, refers to any material that may interfere with the precision and/or accuracy of the assays of the cell or cell contents. Contaminants include, but are not limited to proteins, small molecules, salts, buffers, RNA, DNA, other cells, particles, and so forth.

"MicroRNAs" (miRNA), as used herein, are short (19-23 nucleotides long) non-coding ribonucleic acid (RNA) polymers that are implicated in the post-transcriptional regulation of the translation of complementary mRNA into proteins (36). They are expressed as larger transcripts that form self-complementary "hairpin" RNA. miRNA have been shown to be central to many biological pathways including cell proliferation (37), differentiation (38) and death (39), developmental timing (40) and patterning (41), nervous system patterning (39, 42), and virus resistance (43, 44). The wide variety of functional effects, combined with the knowledge that the miRNA expression profile is a unique signature of cellular state (45) suggests that insight into the complicated biochemical nature of many diseases, such as cancer (45-47) and heart disease (48-51), can be gained through studying miRNA expression.

"Reverse transcription quantitative polymerase chain reaction" (RT-qPCR) is a molecular biology technique that is commonly used to measure gene expression (52-54). RT-qPCR extends the functionality of the traditional polymerase chain reaction (PCR), which is a method of specifically and exponentially amplifying a single or a few copies of DNA in situ (54). In RT-qPCR, the first strand of DNA is synthesized from a RNA template through a process called reverse transcription (RT; 54). Specificity is added to the reverse transcription step by exploiting the RT enzymes' need to have a DNA-RNA duplex. Oligonucleotides called primers designed to be complementary to the desired target are thus used to specifically transcribe a piece of RNA into DNA. After the first strand synthesis, traditional PCR is performed in the presence of a fluorescent reporter and primers designed to amplify the DNA transcribed in the previous step (54). The reaction is then monitored after every cycle, and the fluorescence is recorded, producing characteristic sigmoidal curves. After the completion of the reaction, it is then possible to determine the relative starting abundances of the genes (54). The use of RT-qPCR to measure single cell mRNA (55, 56) and miRNA (57, 58) expression levels is well established. It will be understood by those skilled in the art that the analysis of more than one sequence in a single reaction may be performed using optical multiplexing strategies. It will further be understood by one skilled in the art that in addition to quantification of defined sequences, RT-PCR may be used to amplify one or more genes for subsequent recovery and/or analysis.

While the embodiments of the invention described herein are generally concerned with the capture and isolation of cells, and subsequent processing, it will be appreciated that the microfluidic devices according to various aspects of the invention could be used for the capture and analysis predetermined numbers of entities other than cells, including cell organelles, viruses, microparticles, droplets, etc.

Example 1

Example 1.1 Materials and Methods

Nucleic Acid Detection and Quantification

DNA quantification through microarray analysis is a highly multiplexed, well established method to assay a sample for thousands of different targets. Specific DNA sequences that have been immobilized on a solid surface act as probes to target molecules in solution. The solution containing these target molecules is flowed over the surface of the microarray, and target molecules bind to the immobilized probes via standard DNA base pairing. Probe-target hybridization is detected and quantified by the detection of a fluorophore or a silver or chemiluminescent target. While microarray analysis has been used on single cells, it requires an amplification step (59) in order to generate the quantity of target molecules required to meet the assay detection limits.

Single molecule imaging techniques, including fluorescence in situ hybridization (FISH; 60, 61) and single fluorophore imaging (62) have been used to directly count the number of transcripts in a single cell. While these methods stand alone in their ability to quantify transcript abundance by direct observation, they can only be multiplexed optically, and require highly specialized equipment.

Methods that have been developed to specifically detect and quantify miRNA include northern blot (64), in situ hybridization (60, 61), single molecule imaging (62), microarray (65, 66), next-generation sequencing (67) and RT-qPCR with stem-loop RT primers and TaqMan probes (68). Because of the large dynamic range, high degree of specificity and the fact that many methods of single cell transcript quantification require a PCR amplification, RT-qPCR using stem-loop primers and TaqMan probes was chosen in order to measure miRNA abundance. Stem-loop primers contain a self-complementary region, and therefore "fold back" on themselves creating a hairpin structure. This structure prevents the primer from binding to RNA molecules other than at the very end of a molecule, which prevents miRNA precursors from being amplified (68). TaqMan probes are hydrolysis probes designed to increase the specificity of qPCR (69). A hydrolysis probe is an oligonucleotide labeled with a fluorophore on one end, and a quencher on the other. When the complete probe is free in solution, the fluorophore is close enough to the quencher such that any fluorescence emitted by the fluorophore is quenched by the quencher through fluorescence resonance energy transfer (FRET) (69). During PCR, the probe binds to its complementary sequence, and is cleaved through the exonuclease activity of the Taq polymerase, thereby separating the fluorophore and the quencher (69). Thus, after each cycle, there will ideally be a two-fold increase in fluorescence. Through measuring the fluorescence after every cycle, or in "real time", it is possible to determine relative starting abundances. The inclusion of a serial dilution of known concentrations in the experiment (referred to as a standard) produces a calibration curve, allowing the initial starting number of molecules to be calculated.

Fabrication

Multilayer Soft Lithography (MSL) was used to fabricate devices (63, 70). The fabrication process takes advantage of well-established photolithography techniques and advances in microelectronic fabrication technology. The first step in MSL is to draw a design using computer drafting software, which is then printed on high-resolution masks. Silicon wafers covered in photoresist are exposed to ultraviolet light, which is filtered out in certain regions by the mask. Depending on whether the photoresist is negative or positive, either areas exposed (negative) or not (positive) will crosslink and the resist will polymerise. The unpolymerised resist is soluble in a developer solution and is subsequently washed away. By combining different photoresists and spin coating at different speeds, wafers can be patterned with a variety of different shapes and heights. The wafers are then used as moulds to transfer the patterns to polydimethylsiloxane (PDMS). In MSL, stacking different layers of PDMS cast from different moulds on top of each other is used to create channels in overlapping "flow" and "control" layers (63, 70). The two (or more) layers are bound together by mixing a potting prepolymer component and a hardener component at complementary stochiometric ratios to achieve vulcanization. In order to create a simple microfluidic chip, a "thick" layer is cast from the mould containing the flow layer, and the "thin" layer is cast from the mould containing the control layer. After partial vulcanization of both layers, the flow layer is peeled off the mould, and manually aligned to the control layer. These layers are allowed to bond, and then this double slab is peeled from the control mould, and then holes for inlets and outlets are punched and the double slab is bonded to a blank layer of PDMS. After allowing more time to bond, the completed device is mounted on glass slides.

Fluid flow in the device is controlled using off-chip computer programmable solenoids which actuate the pressure applied to fluid in the control layer. When pressure is applied to these lines, the flexible membrane between the overlapping orthogonal control and flow lines deflects into the flow channel, effectively valving the flow. Different combinations of these valves can be used to create peristaltic pumps, multiplexer controls and isolate different regions of the chip.

Example 1.2: Cell Capture

In order to increase the capture efficiency, decrease the size selectivity of the trap design, and attempt to characterize how trap dimensions affect capture efficiencies for different cell types, a variety of different trap geometries were designed and tested on two different cell lines: K562 cells, a human erythroleukemic cell line with an average diameter of 18 microns, and nBAF3, a murine pro-B-cell line with an average diameter of 12 microns.

Figure 2:
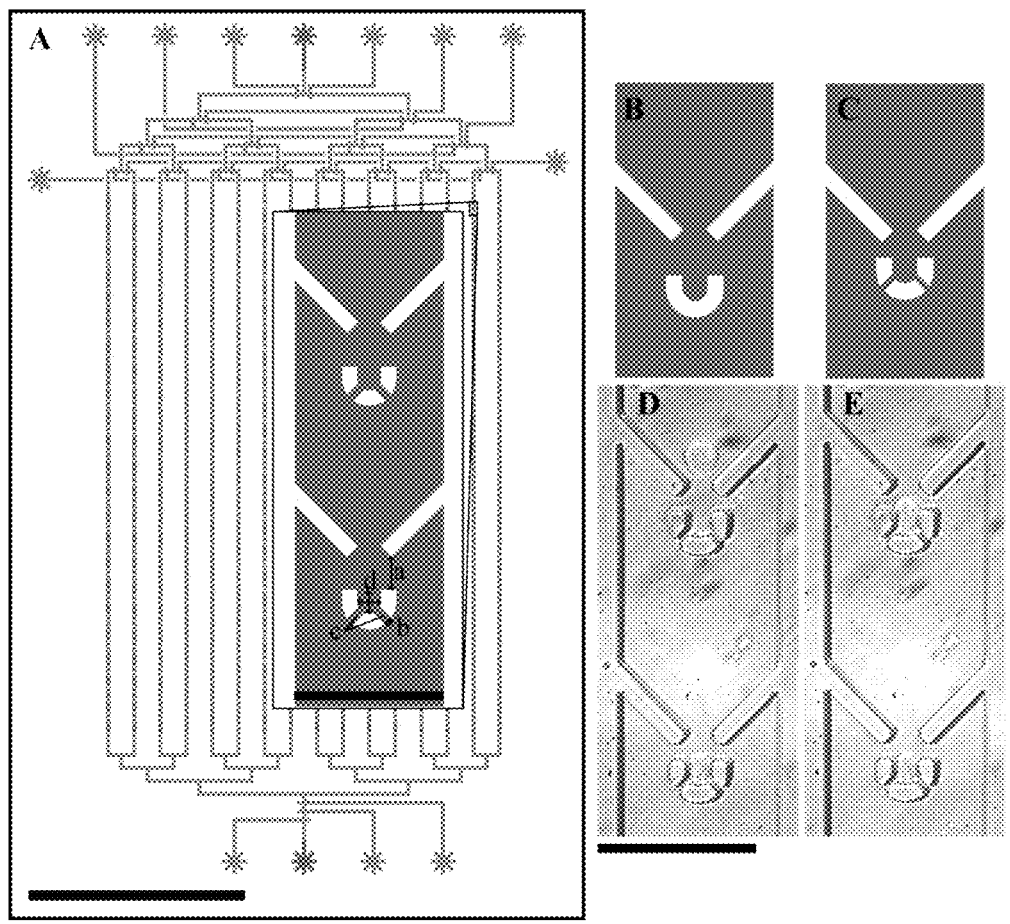
FIG. 2, panel A, is a schematic drawing a of cell capture testing device.

Ninety-six (96) different trap geometries were fabricated and tested in six independent devices. A schematic of cell capture testing device is shown in FIG. 2, panel A. A single device is able to analyze 16 different trap geometries, each replicated 83 times in a single column, with 150 microns separating each trap. A binary demultiplexor (top of device) is used to select the desired trap geometry, and a microfluidic peristaltic pump (bottom of device) is used to pump the cells through the device. The scale bar is 500 microns. The inset shows an enlarged region encompassing two cell traps. The parameters tested in the screen of geometries were "a" the distance between the flow focuser and the capture weir, "b" the width of the sections removed from the weir (i.e. the sieve elements), "c" the number of sections removed (i.e. sieve elements) and d the dimensions of the capture weir. The inset scale bar is 100 microns. FIG. 2, panels B and C, show the original and optimized trap geometries, respectively. FIG. 2, panel D, shows an optical micrograph of a single K562 approaching the trap geometry presented in FIG. 2, panel C. FIG. 2, panel E, shows this same cell after being trapped. The scale bar in B-E is 100 microns.

The fabrication protocol was optimized so that high aspect ratio (ranging from 7:2 to 14:1) could be reproducibly fabricated across a wafer. In all cases, the channel containing the trap, in these embodiments a capture cage forming a weir, was 14 microns high, and the funnels consisted of two angled, 10 microns wide obstacles.

The distance between the cell trap and the funnel was varied between 22.5 and 8.5 microns, corresponding to an approximate range of 1.25 to 0.5× the diameter of an average K562 cell, and 1.9 to 0.7× the diameter of an average nBAF3 cell. Observations of the cells entering the cell capturing chamber indicated the geometries with the capture cell 8.5 microns from the funnel maximized the single cell fill factor. However, while this distance maximized the fill factor, an increase in the number of blockages was also observed, and so a distance of 10.5 microns was chosen to be integrated in the final device.

The capture cage size was varied between 12×12 microns to 20×36 microns. As expected, an increase in the number of traps containing more than a single cell was observed with increasing cup size.

The removal of one, two, three and four sections to create sieve elements with widths varying from 1 micron to 6 microns (1, 2, 4, 6) was also tested. Observations of cells entering the traps indicated that 6 micron wide sieve elements permitted some cells to squeeze through the trap. There were not any observable differences between removing one or two sections from (i.e. between creating one or two sieve elements in) the trap. In order to determine if there was enough flow through the traps with sieve elements such that the funnels could be removed from the design, a selection of the traps with different numbers of sieve elements was tested without the funnels. In all these cases, no cells were observed to be trapped in a trap that wasn't directly downstream of a funnel.

Thus, after testing the 96 different trap geometries, satisfactory capture efficiencies on K562 cells were observed for a 12×12 micron capture cup located 10.5 microns from the flow focusers, with two 4 micron segments removed from the capture weir.

Example 1.3: Lysis

Two lysis methods were selected for their ease of integration into a microfluidic device: heat lysis, which involves heating the sample to 85° C. for 7 minutes, or a heat-inactivated chemical lysis buffer provided in the Invitrogen SuperScript® μl CellsDirect cDNA Synthesis Kit. In order to assess the relative efficiency of each method on releasing miRNA from the cells and determine if further reactions would be inhibited by the chemical lysis buffer, a sample of K562 cells was serially diluted and lysed using each method. Released miRNA from these samples was subsequently reverse-transcribed into cDNA and the amount in each sample was quantified using qPCR.

Figure 3:
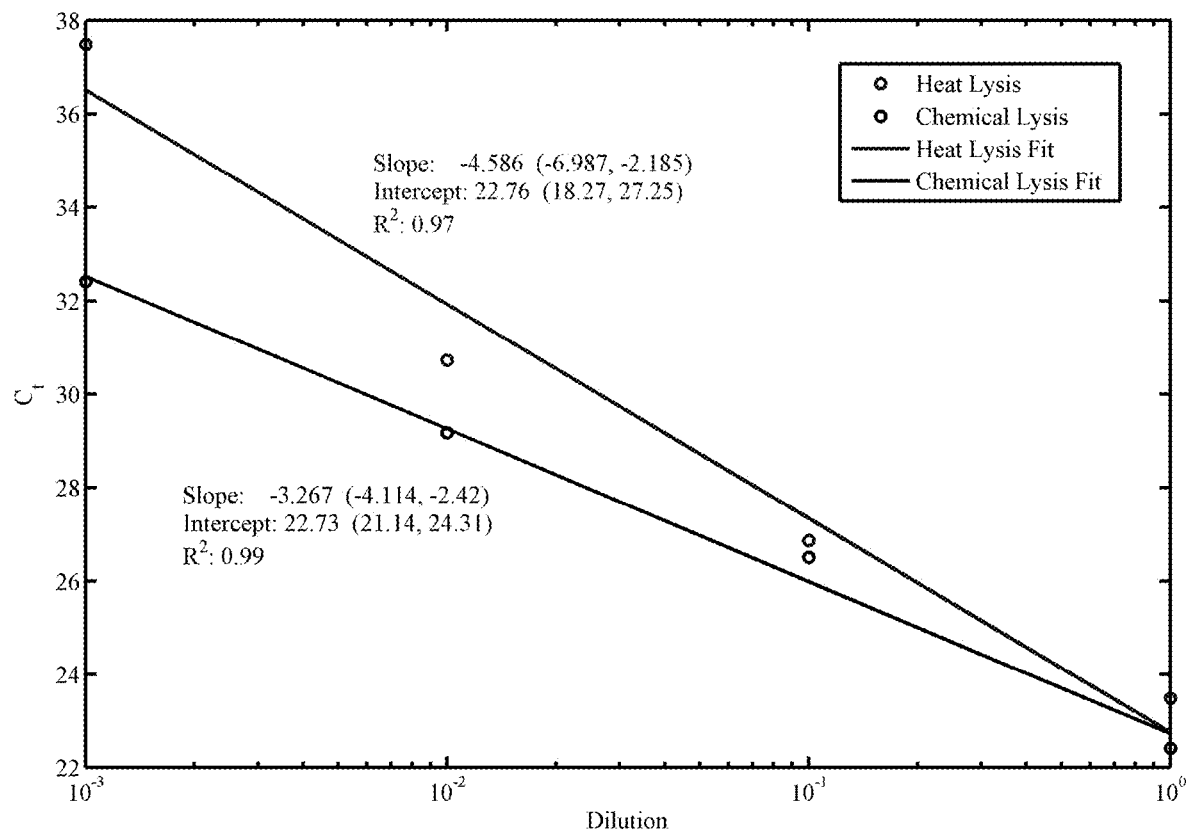
FIG. 3 is a graph depicting the results of a comparison of chemical and heat lysis methods.

The results from this test can be found in FIG. 3. The efficiency of the chemical lysis more closely resembles the expected value of approximately −3.3 cycles per 10-fold dilution. However, the increased benefit of the chemical lysis is reduced by the fact that using it requires the addition of an extra chamber on the final device, thereby sacrificing valuable density.

Example 1.4: Cell Loading and On-Chip Cell Wash

Figure 4:
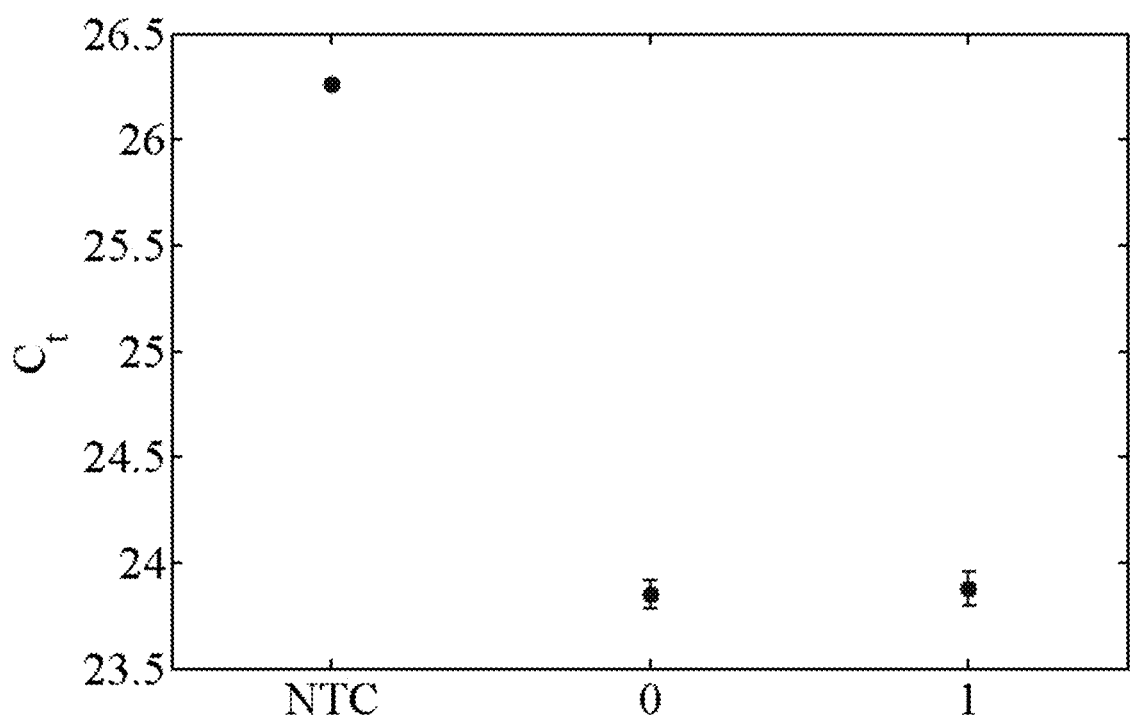
FIG. 4 is a graph comparing background signal to signal from a single cell.

Preliminary results shown in FIG. 4 indicated that it was not possible to distinguish between background signal and the signal from a single cell. However, the possibility that this signal was coming solely from reagent contamination was ruled out as a region of the chip in which cells did not flow through was distinguishable from the rest of the background. This result suggested that there was a non-negligible amount of free floating miRNA in the media the cells were suspended in. The solution to this problem was to wash the cells captured in the traps with clean culture media before lysis, thereby washing any free-floating miRNA, excess cells and any other debris out from the chip.

Example 1.5: Cell Lysate Inhibition of RT-qPCR

High concentrations of cell lysate inhibit molecular biological reactions. The following experiment was performed in order to determine the optimal cell lysate dilution so that subsequent RT and qPCR reactions can be performed on the sample. A 10× dilution series of K562 cell lysate prepared off-chip (10 cells to 1/1000 cell equivalents per capture chamber) was loaded into a custom microfluidic device which contained an array of chambers testing a variety of cell lysate to RT volume dilution ratios. All reactions were performed in technical triplicate. A synthetically synthesized species of miRNA from *Caenorhabditis elegans* (cel-mir-2) was added to the reverse transcription mix at a constant concentration of 0.2 ng/nL. The standard miRNA pulsed reverse transcription 38,39 was performed, the product from this reaction was diluted five-fold, and on-chip qPCR was performed, assaying for the synthetic *C. elegans* miRNA.

Figure 5:
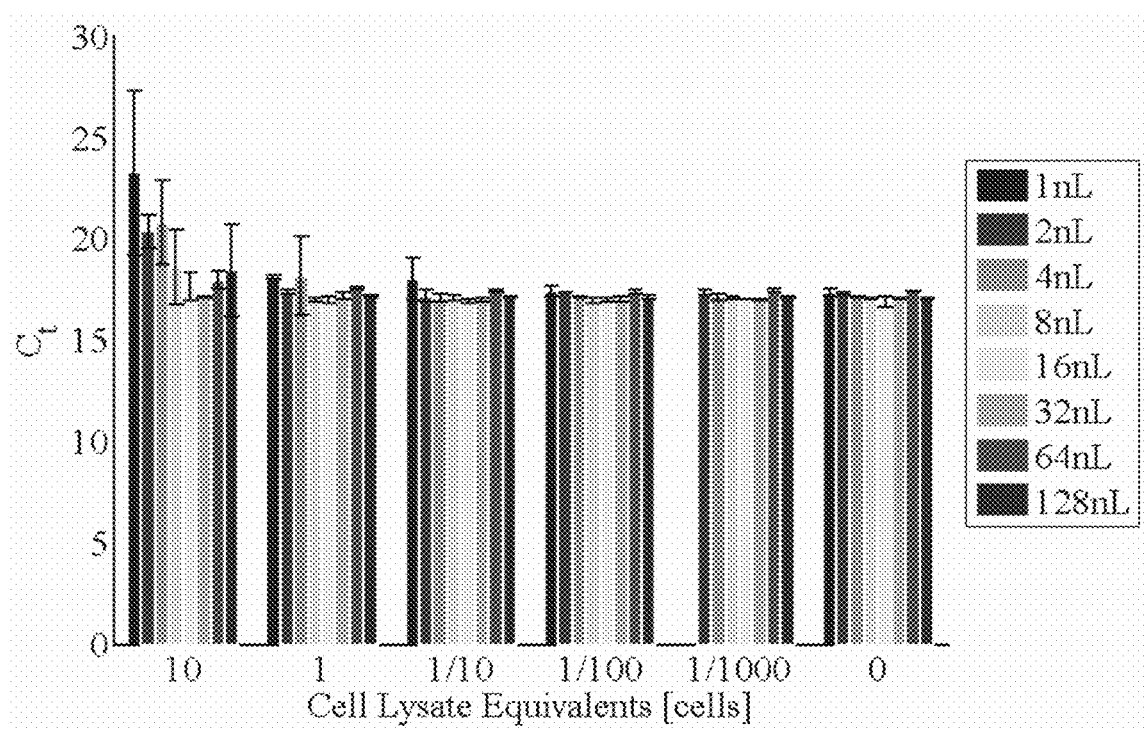
FIG. 5 is a graph depicting the effect of cell lysate concentration on inhibition of RT-qPCR.

Because the assayed miRNA is not found in K562 cells, the effect of inhibition due to different concentrations of cell lysate on RT-qPCR can be inferred. The results from this experiment are presented in FIG. 5. An increase in cycle threshold (Cc) was seen at concentrations of 10 cells per capture chamber at 1 nL, 2 nL, 4 nL and 8 nL RT chamber volumes. This increase in $C_t$ value directly corresponds to reaction inhibition due to cell lysate. Thus, in order to account for a variety of cell sizes and types, a minimum RT chamber volume of dilution of approximately 13× (0.6 nL cell capture chamber into 8 nL RT chamber) is preferred to sufficiently dilute out the cell lysate such that downstream RT-qPCR reactions are not inhibited.

Example 1.6: RT to PCR Dilution

RT to PCR dilution ratios of 1:2.1 to 1:21 were tested in order to determine the effect of this dilution on qPCR performance. K562 lysate was processed in tubes, reverse transcribed, and added in different dilutions to PCR mix.

Figure 6:
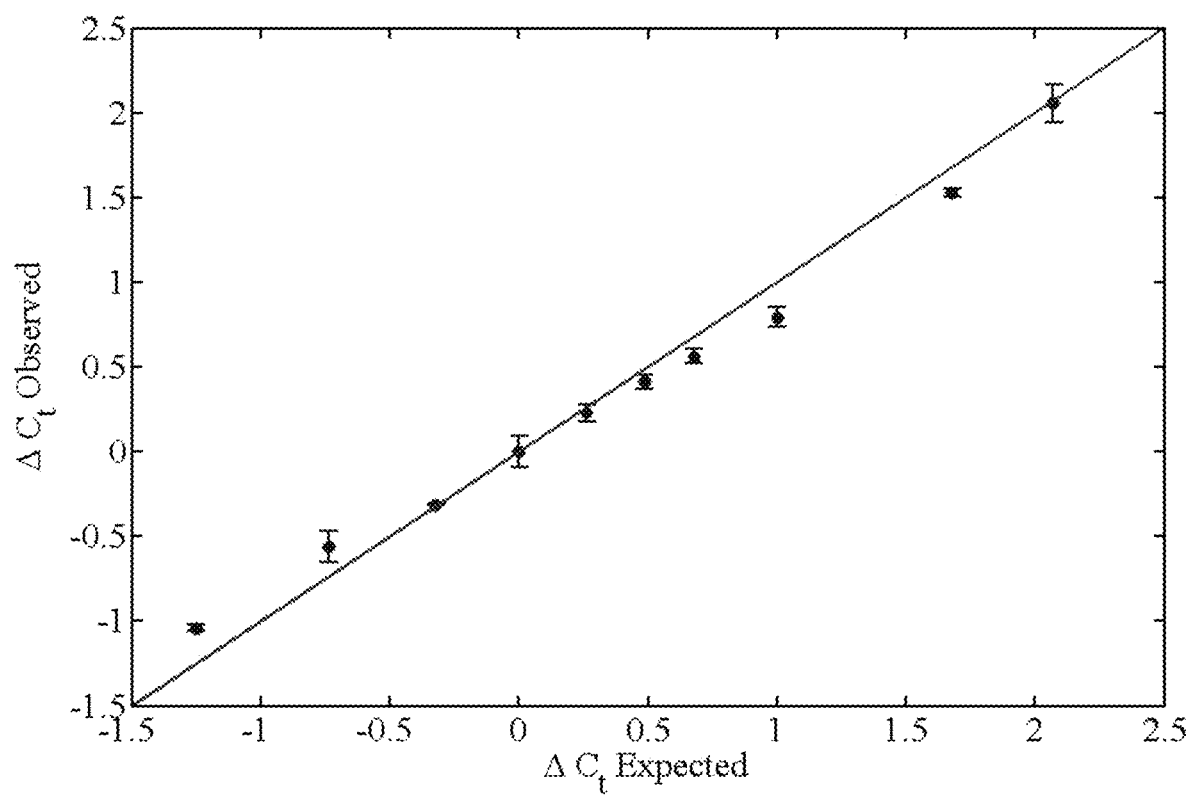
FIG. 6 is a graph showing the effect of different RT to PCR dilutions on qPCR performance.

FIG. 6 shows the effect of different RT to PCR dilutions on qPCR performance. The points, from left to right represent dilutions of factors of 2.1, 3, 4, 5, 6, 7, 8, 10, 16 and 21. All results were normalized to 1:5, as this was used in the protocol presented by ASDF. As can be seen by this figure, reaction inhibition is seen at low (1:2.1, 1:3) dilution factors. The total concentration of template, and hence the sensitivity of analysis is reduced with higher dilution factors. Thus, a dilution factor of 5× was used as the dilution factor in the final device. Error bars represent standard deviation of two samples.

Example 1.7: Pre-Amplification Verification and Elution Efficiency

A device encompassing the design considerations outlined above was designed, fabricated and tested in order to verify the combined functioning of cell trapping, washing, and lysis, followed by reverse transcription and pre-amplification and to test sample elution strategies. A schematic for this device can be found in FIG. 7. This device featured the ability to capture 10 single cells in parallel, a 1 nL cell processing chambers, 15 nL reverse transcription reaction chambers, 75 nL PCR pre-amplification reaction chambers, a factorial demultiplexor, used to individually address each sample, and a peristaltic pump.

Figure 8:
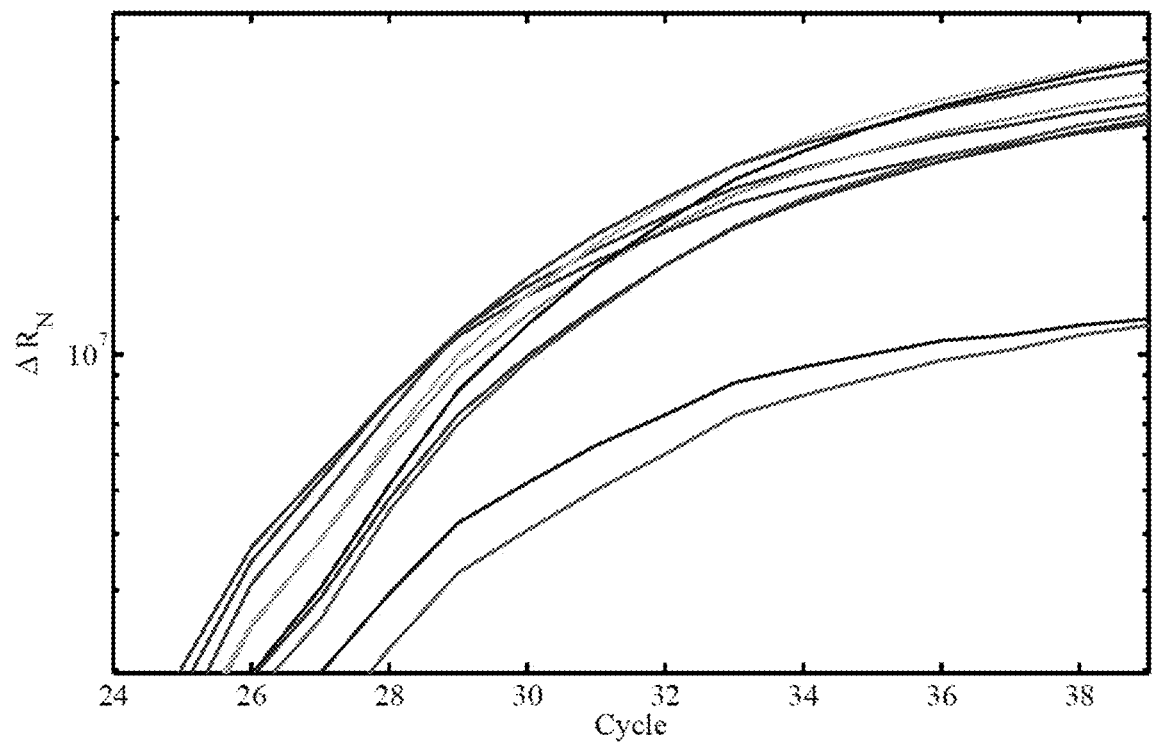
FIG. 8 is a graph depicting qPCR results on nine single cells assayed for miRNA16 and one no cell control.

Ten single K562 cells were trapped and lysed. Human miRNA 16 (hsa-mir-16) was then reverse transcribed, and relative copy number determined via qPCR. The real-time PCR curves from this experiment can be found in FIG. 8. All cells were expressing miRNA 16, and all curves came up with an average cycle threshold of 26, and a standard deviation within 1 $C_t$ of the mean.

Example 1.8 Elution Methods

Figure 7:
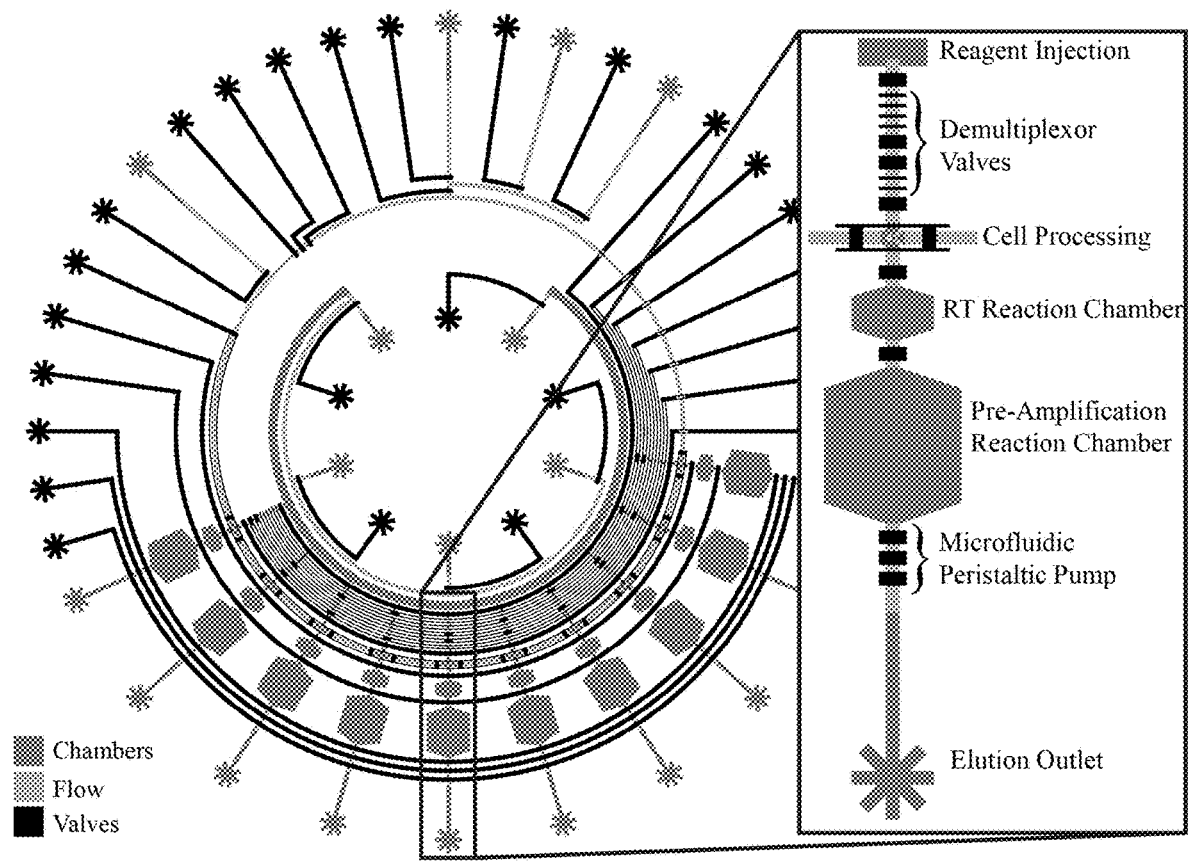
FIG. 7 is schematic drawing for a microfluidic device according to one embodiment of the invention.

As mentioned above, the design used to verify the combined functioning of the biochemical assays presented in FIG. 7 included a factorial demultiplexor so that each chamber could be individually addressed, and a microfluidic peristaltic pump. Both of these design features were integrated in order to test elution methods. Because qPCR measures relative starting concentrations of DNA in solution, it is important to elute each chamber with the same volume. A variety of elution methods were tested: 40 000 microfluidic peristaltic pump cycles, pressure-driven flow for a certain amount of time, elution onto Whatman filter paper followed by DNA resuspension in TE buffer, elution followed by sample drying and resuspension in a known volume and injecting fluid into the device using a Harvard Apparatus syringe pump (PHD 2000). The results of each test are summarized in Table 1. All presented data is the average of 10 replicates, and error is measured as the standard deviation of the measurements.

TABLE 1

Summary of measurements to test elution methods.

| Elution Method Measurement | Method | Mean ± Standard Deviation |
| --- | --- | --- |
| Microfluidic Pump | Weigh Pipette Tips | 3.13 mg ± 0.32 (10%) |
| BD 1 mL Plastic Syringe | Weigh Pipette Tips | 4.10 mg ± 0.20 (5%) |
| BD 1 mL Plastic Syringe | qPCR on Cell Lysate Cycle | 30.7 ± 0.7 |
| Whatman Filter Paper | qPCR on Cell Lysate Cycle | 23 ± 0.4 |

While elution onto Whatman filter paper and elution followed by sample drying produced the most reproducible results, these methods added significant time to the workflow. It was determined that elution using a syringe pump and a high-precision glass syringe (Hamilton, 500 uL) produced both consistent elution results without significantly impeding the experimental protocol. Because the syringe pump can be computer controlled, this elution method is also fully automatable.

Figure 9:
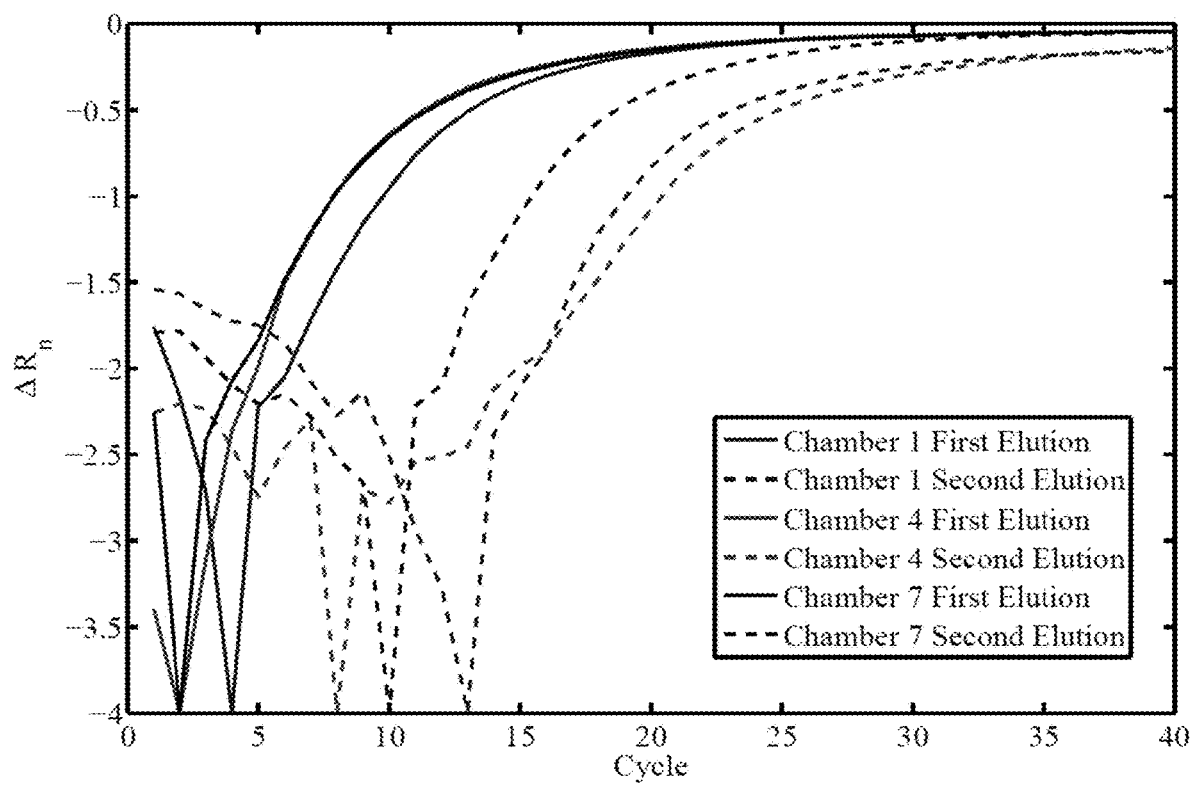
FIG. 9 is a graph depicting elution efficiency measurement of three of the chambers from the experiment presented in section after being eluted twice.

In order to assess the elution efficiency, the qPCR reaction presented in the above section was brought to saturation (40 cycles, see FIG. 8) and the resulting product was eluted from the device by injecting 20 uL using a syringe pump, thereby diluting the product 266×. The real-time curves from these chambers can be seen in FIG. 9. Three of these chambers were then eluted a second time in order to assess the elution efficiency. On average, there was approximately an 813±5 fold decrease in relative abundance, corresponding to an elution efficiency of 99.877%±0.0008%.

Example 1.9: Final Integrated Device Design

Figure 10:
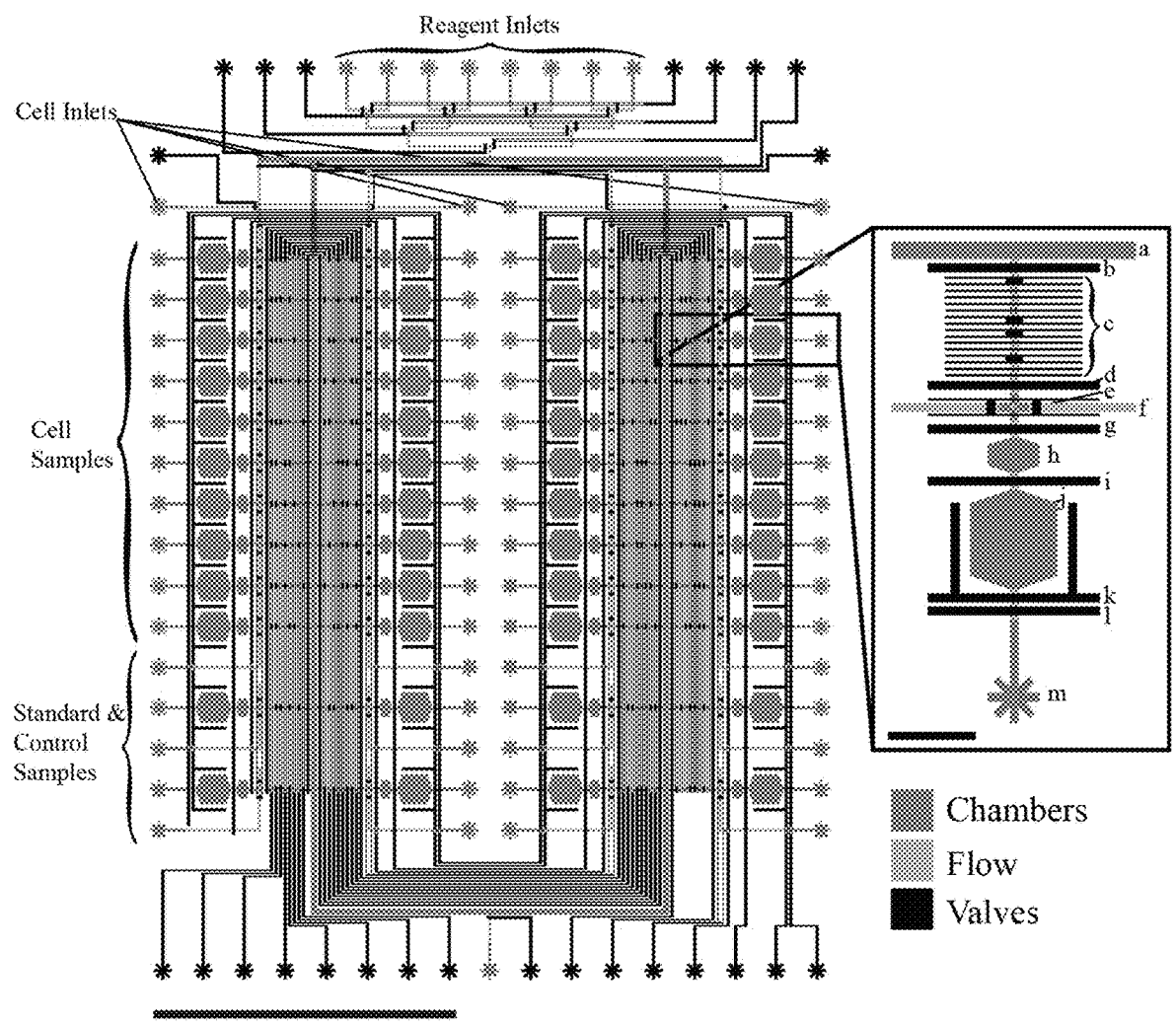
FIG. 10 is a schematic diagram of a microfluidic device for single cell capture analysis according to one embodiment of the invention.

With all of the pieces required for highly multiplexed single cell gene analysis in place, a device was designed that is capable of processing forty single cells, seven standards and an NTC all in parallel. The device was designed to match the throughput of the Fluidigm 48.48 Dynamic Array (DA) being used for endpoint quantification. A schematic of the device can be found in FIG. 10. This device features the ability to process 40 single cells from up to four different populations (up to four independent cell populations can be tested, each containing 10 samples), seven standards, and a no template control, all in parallel. The inset shows an enlargement of one of the units in the array. Each unit is connected to a reagent injection line a, and a cell loading line f. Control line b is used to isolate each unit from the reagent injection line. Control lines c are used to individually address each sample. Control lines d, e and g are used to isolate the cell processing region from subsequent reaction chambers and neighboring processing units. A reverse transcription reaction chamber is downstream of the cell processing region at h, immediately followed by a PCR pre-amplification chamber at j. Control line i is used to separate each reaction chamber. Control line k is used to hydrate the PCR chamber during thermocycling, and control line l is used to isolate the PCR reaction chamber. Pre-amplification product is eluted through the outlet m. The scale bar is 1 cm, and the inset scale bar is 1 mm.

Figure 11:
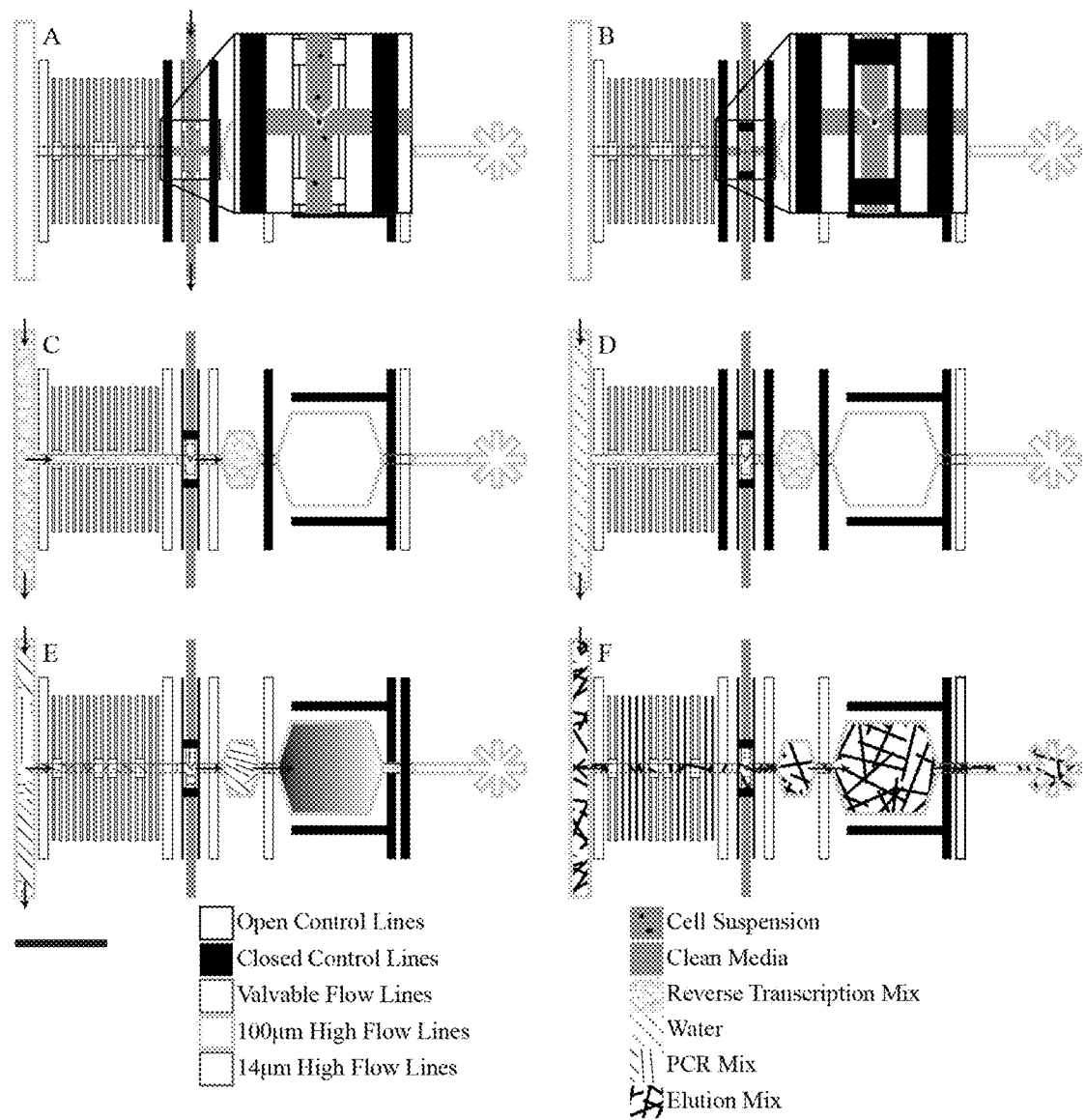
FIG. 11, panels A-F, is a schematic diagram outlining the operation of the microfluidic device of FIG. 10.

A basic schematic of the process is illustrated in FIG. 11. Briefly, cells are captured using the optimized capture weir described in Example 1.1 (FIG. 11, panel A). After the captured cells have been washed by flowing clean culture media over them (washing untrapped cells, debris and any extracellular miRNA out of the device), valves then partition the loading channels into a linear array of 1 nL lysis chambers (FIG. 11, panel B). Cells are then lysed by placing the entire device on a flatbed thermocycler, and heating it to 85.0 for seven minutes. After lysis, reverse transcription mix is injected through the reagent injection lines, pushing the entire contents of each lysis chamber into the reverse transcription chamber (FIG. 11, panel C). The reagent injection lines are flushed with water (FIG. 11, panel D), and the device is then placed on a flatbed thermocycler, and a pulsed RT protocol is run. The RT product is then pushed into the PCR pre-amplification chamber with PCR mix (FIG. 11, panel E). The device is left for one hour at room temperature to allow the RT product and PCR mix to diffusively mix, and the reagent injection lines are once again washed, as depicted in FIG. 11, panel D. The device is once again placed on a flatbed thermocycler, and a low-cycle pre-amplification PCR protocol is run. Following pre-amplification, a capillary pipette tip is plugged into each outlet port, and a syringe in a syringe pump is connected. Each sample is then serially eluted by injecting 10 uL of elution mix into each chamber, diluting the product 100× (FIG. 11, panel F). After being eluted, each sample is then loaded into a separate well on the Fluidigm 48.48 DA chip.

The entire process takes approximately 16 hours, and uses less than 5 µL of RT mix, 10 µL of pre-amplification mix, and 500 µL of qPCR mix. In total, there are approximately 210 pipetting steps. Performing an equivalent experiment in tubes would require more than 240 µL RT mix, 960 µL of pre-amplification mix, and more than 46 mL of qPCR mix. This tube-based experiment would require more than 4700 pipetting steps. Thus, the presented work results in an improved protocol, significantly reducing the cost and time required to perform highly parallel, highly multiplexed single cell analysis.

Example 2

Figure 12:
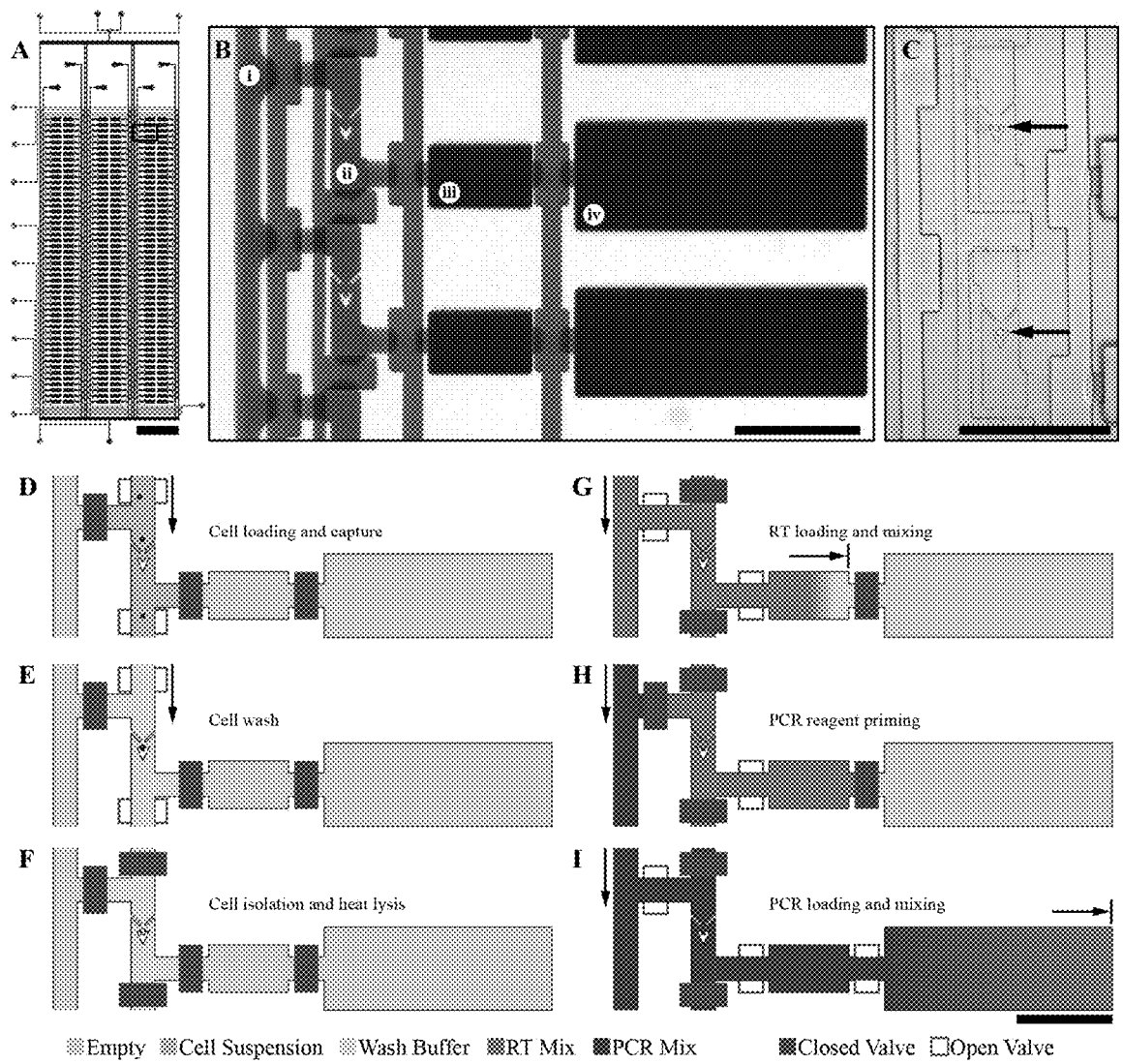
FIG. 12, panel A, is a microfluidic device according to one embodiment of the invention. Scale bar: 4 mm. The device features 6 sample input channels, each divided into 50 compound reaction chambers for a total of 300 RT-qPCR reactions using approximately 20 µL of reagents. Rectangular box indicates the region depicted in FIG. 12, panel B.

An integrated microfluidic device that performs 300 parallel RT-qPCR assays and executes all steps of single-cell capture, lysis, reverse transcription, and qPCR is shown in FIG. 12, panel A. To facilitate the precise comparison of different samples and cell types, the device consists of 6 independent sample-loading lanes, each containing 50 cell-processing units for a total of 300 RT-qPCR reactions using approximately 20 µL of reagents. Design elements were included to 1) allow for efficient distribution of single cells without mechanical damage, 2) minimize background signal arising from free RNA or cell debris in the medium, and 3) avoid reaction inhibition by cell lysates in nL volumes.

In order to reduce device complexity and obviate the need for RNA purification, the device was optimized to be compatible with commercially available assays that use "one-pot" RT-qPCR protocols requiring only the sequential addition of reagents into a single reaction vessel. The rectangular box in FIG. 12, panel A, indicates the region depicted in FIG. 12, panel B. Each cell-processing unit consists of a compound chamber, formed by a cell capture chamber connected sequentially to two larger auxiliary chambers for RT and qPCR (FIG. 12, panel B). Each unit consists of (i) a reagent injection line, (ii) a 0.6 nL cell capture chamber with integrated cell traps, (iii) a 10 nL RT chamber, and (iv) a 50 nL PCR chamber (scale bar: 400 µm). FIG. 12, panel C, is an optical micrograph of two cell capture chambers with trapped single cells indicated by black arrows. Each trap includes a cell funnel comprising deflectors to direct cells into the capture region (scale bar: 400 µm). FIG. 12, panels D-I, are schematic diagrams of the device's operation (scale bar for D-I: 400 µm). In FIG. 12, panel D, a single cell suspension is injected into the device. In FIG. 12, panel E, cell traps isolate single cells from the fluid stream and permit washing of cells to remove extracellular RNA. In FIG. 12, panel F, actuation of pneumatic valves results in single cell isolation prior to heat lysis. In FIG. 12, panel G, reagent for reverse transcription (RT) reaction (10 nL) is injected via a reagent injection line. In FIG. 12, panel H, the reagent injection line is flushed with subsequent reagent for PCR. In FIG. 12, panel I, reagent for qPCR is combined with RT product in a 50 nL qPCR chamber.

This simple fluidic architecture allows the implementation of either heat lysis followed by two-step RT-qPCR (FIG. 12, panels D-I), or chemical lysis followed by one-step RT-qPCR. All lanes are connected to a common feed channel which, following the completion of each reaction step, is used to inject the next reaction master mix through the upstream chambers, thereby diluting the intermediate product (cell lysate or cDNA) and assembling the next reaction mixture. This parallelization of reaction assembly in a microfluidic format ensures equal timing of all reaction steps and greatly reduces technical variability associated with pipetting and mixing steps in µL volumes. Fluorescence measurements were performed to ensure the efficient and reproducible transfer of reactants at each step, showing that losses in sample transfer are below 5%. To minimize device expense and complexity, temperature control and fluorescence detection were performed using peripheral hardware including a CCD detector mounted above a flatbed thermocycler plate.

Example 2.1: Materials and Method

Device Fabrication and Operation

Figure 20:
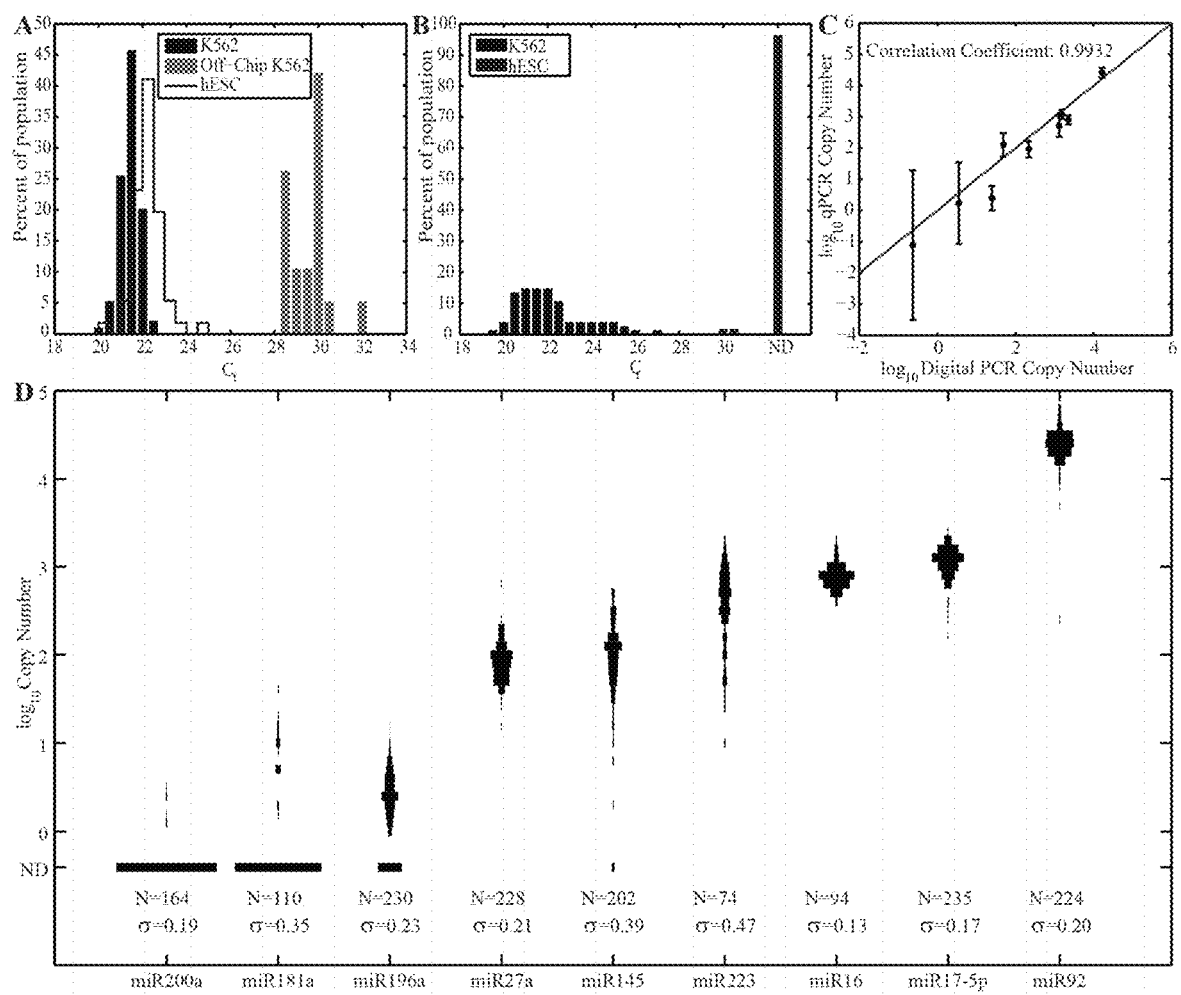
FIG. 20, panel A, is a histogram of single cell measurements of miR-16 expression in K562 cells and hESCs.

Measurements of mRNA and miRNA abundance performed on single cells as described above were found to consistent with average copy numbers measured by digital PCR on cell lysates (FIG. 20, panel C). Microfluidic devices were fabricated by multilayer soft lithography (70, 71). Planar silicon molds were defined by photolithography, using photomasks designed with CAD software (AutoCAD, Autodesk Inc.), and printed on transparency films at a resolution of 20,000 dots per inch (CAD/Art services). The 'control' mold was fabricated using SU8-2025 photoresist (Microchem, USA) to deposit valve features 24 µm in height. The 'flow' mold was fabricated with three lithographic steps. First, the channels for reagent injection, and connections between chambers were fabricated using 13 µm high SPR220-7 photoresist (Shipley, USA). The SPR channels were rounded to facilitate valve closure by incubation at 115° C. for 15 minutes. A hard bake at 190° C. for 2 hours was used to prevent SPR photoresist erosion during addition of subsequent layers. Second, the cell trap features were defined in 14 µm SU8-2010 photoresist (Microchem, USA). Finally, the large chambers and fluidic bus lines were constructed using 150 µm high SU8-100 photoresist. All photoresist processing was performed according to manufacturer specifications.

Microfluidic devices were cast from these molds in polydimethylsiloxane (PDMS, RTV615, General Electric, USA). Each device consists of a three layer elastomeric structure with a blank bottom layer, a middle 'control' layer with channels that act as valves by pushing up and pinching closed channels in the above 'flow' layer. The molds were first treated with chlorotrimethylsilane (TMCS, Aldrich) vapor for 2 min to prevent PDMS from bonding to the photoresist structures. The flow layer was made by pouring a mixture of PDMS (5 parts RTV615A: 1 part RTV615B) onto the flow mold, degassing, and then baking for 60 min at 80° C. A thin control layer was made by spin coating the control mold with PDMS (20 parts RTV615A: 1 part RTV615B) at 1800 rpm and baking for 45 min at 80° C. After baking, the PDMS of the flow layer was peeled from the flow mold and aligned to the control layer. Following a 60 min bake at 80° C., the bonded two layer structure was separated from the control mold, and channel access holes were punched. A blank layer (without channels) was prepared by spinning PDMS (20 parts RTV615A: 1 part RTV615B) on a blank wafer (2000 rpm) and baking 45 min at 80° C. The bonded flow and control structure was mounted on to the blank layer, and baked for 3 hours at 80° C. Finally, the three layer bonded structure was removed from the blank mold, diced into individual devices, and these were each bonded to clean glass slides by baking overnight at 80° C.

The device operation requires control of 9 pneumatic valves and may be operated using a simple manifold of manual valves. For the current study a semi-automated implementation was used in which microfluidic valves were controlled by solenoid actuators (Fluidigm Corp., San Francisco) controlled through a digital input output card (NI-DAQ, DIO-32H, National Instruments) operated using LabView drivers (National Instruments). Tygon tubing connected the solenoids to the microfluidic device by 20 gauge stainless steel pins (Small Parts Inc.) fitted into the control line ports. Krytox (DuPont) oil was used as the fluid in the control lines, and the valves were actuated with 30 psi pressure.

Microfluidic Single Cell RT-qPCR

The device was designed to be compatible with commercially available RT-qPCR products. A protocol for heat lysis, followed by a 2-step RT-qPCR was used with miRNA and OCT4 mRNA assays. Alternatively, a chemical lysis, followed by 1-step RT-qPCR was used for mRNA measurements of SNVs and GAPDH.

Single Cell Transcript Measurements by Heat Lysis and 2-Step RT-qPCR

The device was primed by flowing PBS containing 0.5 mg/mL bovine serum albumin (BSA) and 0.5 U/µL RNase Inhibitor through all channels, while keeping the RT, and PCR chambers empty and isolated by valves. The BSA helped prevent cells from adhering to channel walls. After priming, but prior to cell loading, all valves were closed. A single cell suspension was injected into the device by applying pressure (~2-3 psi) to microcapillery pipette tips plugged into the sample inlets. The sample inlets were first dead-end filled against an inlet valve to prevent air bubbles from entering the device. The sample inlet valves, cell chamber valves and outlet valve were opened to allow the cell suspension to flow through the sample channels. Cells were loaded into the device suspended in culture media (directly from culture). Cell loading concentrations were kept between $5\times10^5$ cells/mL and $1\times10^6$ cells/mL, resulting in over 80% occupancy of cell traps with single cells in 1-2 min at a flow rate of approximately 20 nL/s.

Lower concentrations were found to require proportionately longer times to achieve high occupancy of trapped single cells. Concentrations greater than $2\times10^6$ cells/mL were found to occasionally clog the inlet port or the channel at trap locations. A peristaltic pump was integrated into the device for controlling the flow rate, however pressure driven flow was used for the current study.

After injecting the cell suspension and trapping single cells the cell sample inlet valve was closed, and the cells were washed by flushing the line with the PBS solution used to prime the device. This removed untrapped single cells, extracellular RNA, and debris. Following on-chip washing, the cell chamber valves were closed to partition the cell loading channel and isolate individual cell reactors. Visual inspection of the cell capture chambers with a microscope was used to confirm and count the number of cells in each chamber. The cells were lysed by placing the microfluidic device onto a flatbed thermocycler and heating to 85° C. for 7 minutes (and then cooled to 4° C.).

Reverse transcription (RT) was performed in the device by using the ABI High Capacity Reverse Transcription kit (68), with the addition of a surfactant to prevent adsorption of nucleic acids and proteins to PDMS surfaces (2 µL 10× Reverse Transcription Buffer, 4 µL 5×RT stem-loop miRNA primer from ABI, 1 µL 100 mM dNTPs, 1.34 µL of 50 U/µL. Multiscribe Reverse Transcriptase, 0.26 µL of 20 U/µL RNase Inhibitor, 2 µL 1% Tween 20, 9.4 µL PCR grade water). The RT mix was loaded into the device, and flushed through the reagent injection channels. RT reagent was injected into the reaction by opening the valve connecting the cell chamber to the RT chamber, and the valve connecting the cell chamber to the reagent injection line. The RT chamber was dead-end filled before closing the connection to the reagent injection line. A pulsed temperature RT protocol was carried out by placing the microfluidic device on a flatbed thermocycler (2 min at 16° C., followed by 60 cycles of 30 seconds at 20° C., 30 seconds at 42° C., and 1 second at 50° C.). RT enzyme was inactivated at 85° C. (5 min), and then the device was cooled to 4° C.

The PCR reagent was prepared with 25 µL of 2× TaqMman Universal Master Mix (ABI), 2.5 µL 20× Real-Time miRNA assays (primers and probe, ABI), 5 µL of 1% Tween 20, and 7.5 µL of PCR grade water. The PCR reagent was flowed through the reagent injection channels to flush away the RT reagent. Valves were opened and the PCR reagent was injected to dilute the RT product into the PCR reaction chamber. After completely filling the PCR reaction chamber, the valves closing the PCR chambers were actuated, and the device was transferred to an enclosure for real-time PCR (Prototype version of Biomark™ Instrument, Fluidigm Calif.). The real-time PCR enclosure consists of a custom flatbed thermocycler, a xenon arc lamp and filter set, and a charged coupled device (CCD) imager with optics for fluorescent imaging of the entire device periodically during PCR thermocycling (see description of real-time PCR instrumentation below). PCRs were thermocycled with the following conditions: 10 min at 95° C., followed by 50 cycles of 15 s at 95° C. and 1 min at 60° C. Images were acquired at 60° C.

Single Cell Transcript Measurements by Chemical Lysis and 1-Step RT-qPCR

Measurements of mRNA transcripts (SP1, GAPDH) were performed using the Cells Direct kit (Invitrogen, USA). Operation of the microfluidic device for chemical lysis and 1-step RT-qPCR was similar to the methods described for heat lysis and 2-step RT-qPCR with several distinctions. The device was primed and cells were washed with PBS containing 0.5 mg/mL BSA. Additional RNase Inhibitor was omitted as the chemical lysis buffer (10 µL lysis resuspension buffer, 1 µL lysis enhancer solution, Invitrogen, USA) contained RNA stabilizing agents. Cell loading was the same as in the heat lysis and 2-step RT-qPCR scenario. Single cells were lysed by injecting a chemical lysis buffer through the cell capture chamber and filling the 10 nL chamber (used for RT reagent injection in the 2-step protocol). The lysis reaction was incubated at room temperature for 10 minutes, followed by heat inactivation of the lysis reagent by placing the device on a flatbed thermocycler and incubating at 70° C. for 10 minutes. The one-step RT-qPCR mix (1 µL of SuperScript III RT/Platinum Taq Mix, 25 µL of 2× Reaction Mix (with ROX reference dye), 2.5 µL of 20× Taqman Assay (primers and probes, ABI), 1 µL of 50 mM $MgSO_4$, 5.5 µL of $H_2O$, and 5 µL of 1% Tween 20) was then combined with the cell lysate into the final 50 nL reaction chamber. The device was transferred to the real-time PCR enclosure for temperature control and imaging of the 1-step RT-qPCR (20 min at 50° C. for RT, followed by a hot-start at 95° C. for 2 min, and 50 cycles of 15 s at 95° C. and 30 s at 60° C.).

Digital PCR Experiments

For mRNA digital PCR analysis cells were washed with PBS containing 0.5 mg/mL BSA, lysed in chemical lysis buffer, reverse transcription was performed in tubes according to the protocol described above, and the resulting cDNA product was loaded into digital PCR arrays. For miRNA studies, cells were lysed in PBS containing 0.5 mg/mL BSA and 0.5 U/pt RNase inhibitor. Reverse transcription was performed using miRNA stem-loop primers (Applied Biosystems, USA) and the High Capacity cDNA Reverse Transcription kit (Applied Biosystems, USA) in 10 µL volumes. Prior to injection into microfluidic digital PCR arrays, RT product was added to the PCR reagent as in the on-chip 2-step RT-qPCR protocol described above. Thermal cycling of digital PCR arrays was also performed using the same protocols as described above. PDMS digital PCR arrays consisting of 765 2 nL individual PCR chambers, of similar design to those described in Warren et al. (72), were fabricated by multilayer soft lithography. After thermal cycling, positive chambers were counted and actual molecule numbers were derived based on the binomial distribution.

System for Real-Time PCR

The BioMark™ Reader is a commercially available real-time PCR instrument developed by Fluidigm and designed to run Fluidigm Integrated Fluidic Circuits (IFCs). The prototype version of this system allowed access to the flatbed thermocycler inside the enclosure, permitting the use of custom microfluidic devices in addition to the intended commercial IFCs.

Fundamental specifications for data collection include:

Image Resolution and bit depth: 4 Megapixel, 16 bit

Filters: FAM: Ex 485/20 Em 525/25;
  VIC: Ex 530/20 Em 570/30;
  ROX: Ex 580/25 Em 610/15;
  QAS: Ex 580/25 Em 680/25, Light Source: 175 W xenon arc bulb RT-qPCR Assays Measuring mRNA in the presence of genomic DNA requires primers designed to specifically target mature mRNA sequences. In many cases, this can be accomplished by designing intron-spanning primers. A specially designed stem-loop RT primer system (Applied Biosystems) is used for the specific targeting of mature miRNAs.

TaqMan assays for GAPDH (Applied Biosystems, Assay ID Hs99999905_m1) and miRNAs were obtained from Applied Biosystems. For GAPDH, a control experiment omitting the reverse transcriptase was performed off-chip, in microliter volumes with bulk cell lysate (at equivalent concentration of a single cell on-chip, $10^5$ cells/mL), and showed no amplification after 40 cycles of PCR.

OCT4 (POU5F1) primer sequences were obtained from RTPrimerDB and synthesized by Biosearch Technologies Inc; Forward primer: ACC CAC ACT GCA GCA GAT CA (SEQ ID NO: 49), Reverse primer: CAC ACT CGG ACC ACA TCC TTC T (SEQ ID NO: 50), Probe: Quasar670-CCA CAT CGC CCA GCA GCT TGG-BHQ-2 (SEQ ID NO: 51), RT primer: TTG TGC ATA GTC GCT GCT TGA T (SEQ ID NO: 52). Measurement of OCT4 in single hESCs by microfluidic RT-qPCR without reverse transcriptase showed no amplification after 40 cycles of PCR.

BHQ-Plus probes with enhanced duplex stabilization (Biosearch Technologies Inc) were used for SNV detection to allow for shorter sequence lengths and increased specificity. The SNV location for the SP1 locus was selected from Table 2 in Shah et al. (73). Two hundred bp flanking this location on the hg18 sequence were used for assay design using Primer3. The resulting primer and probe sequences are as follows (the SNV is underlined):

SP1 Mutant Probe:
                                    (SEQ ID NO: 53)
FAM-AGGCCAGCAAAAACAAGG-BHQ-1

5' Modification: FAM, 3' Modification: BHQ-1 Plus.
Tm = 62.7° C.

SP1 WT probe:
                                    (SEQ ID NO: 54)
Cal Fluor-CAGGCCAGCAAAAAGAA-BHQ-1

5' Modification: CAL Fluor Orange 560, 3' Modification: BHQ-1 plus. Tm = 62.1° C.

SP1 Forward Primer:
                                    (SEQ ID NO: 55)
CCAGACATCTGGAGGCTCATTG Tm = 65.8° C.

SP1 Reverse Primer:
                                    (SEQ ID NO: 56)
TGAACTAGCTGAGGCTGGATA Tm = 66.0° C.

Control experiments without reverse transcriptase showed positive amplification. Therefore the measurement of SP1 mutant and wilde-type abundance in single cells by RT-qPCR does not discriminate between mature mRNA transcript and genomic DNA.

Image Analysis

Fluorescence images of the entire device were taken in at least two different colors (one passive reference dye and one or more reporter dyes) after each PCR cycle and were analyzed using custom scripts written in MATLAB (MathWorks) to generate real-time amplification curves. Reaction chambers were segmented from the rest of the image using the first image of the passive reference dye. The image was manually rotated so that all of the reaction chambers were square with the edges of the image. Next, the average image intensities across each row and column were calculated and a threshold was manually set to differentiate bright areas from background. Regions containing both bright rows and bright columns were assigned to the reaction chambers.

All subsequent images were automatically aligned to this initial image by minimizing the absolute distance between the average row and column intensities of the initial image, and the one being analyzed. For each image, the intensities of the reporter and passive dyes were recorded for each reaction chamber. Real time amplification curves were generated by normalizing the intensity of each reporter dye to that of the passive dye. Linear components were removed from these curves by fitting the equation of a line to the pre-exponential region and extrapolating and subtracting the result from the entire curve. The threshold for determining CT values was automatically determined as the median normalized fluorescence value at the maximum second derivative of all amplification curves.

mRNA FISH

Microfluidic measurements of Oct4 expression in single cells were found to be consistent with OCT4 measurements obtained by mRNA FISH. For mRNA FISH measurements, cells grown on LABTEK chambered cover-glass were washed with PBS, fixed in 4% formaldehyde for 10 min at room temperature and permeabilized in 70% EtOH at 40° C. overnight. The next day cells were rinsed with wash buffer (15% Formamide in 2×SSC) and then hybridized with the appropriate dilution of mRNA FISH probes specific to OCT4 (see Table 2) in hybridization solution (dextran sulfate, Yeast tRNA, NEB, BSA, 15% Formamide in 2×SSC) overnight at 30° C. The next morning the OCT4 hybridization solution was aspirated and cells were sequentially rinsed and incubated with wash buffer at 30° C. for 30 minutes then washed with 2×SSC. One drop (25 µL) of Slowfade GOLD antifade reagent with DAPI was the added to the cells, covered immediately with a cover slip, and imaged. Stacks of 32-64 mRNA hybridization images (spaced by 0.5 µm) were acquired for each cell using a Leica DMI 6000B inverted microscope with a 100× objective (N.A. 1.3) in DAPI and Texas Red filter spectra.

Fluorescent spots corresponding to individual mRNA molecules in each image stack were evaluated manually since automatic thresholding using previously reported algorithms were found to be unreliable. Difficulty in automating this process was attributed to inconsistent signal to noise using reported protocols and may be related to the thickness of hESC cells (~15 µm). In addition, manual intervention was needed to ascertain the boundaries of adjacent cells. To optimize the signal to noise we systematically varied the probe concentration, incubation time, incubation temperature as well as the formamide concentration in the hybridization buffer solution.

TABLE 2

Sequence of mRNA FISH probes specific to OCT4

| Probe (5'→3') | Name | Probe # | Position | % GC | SEQ ID NO: |
|---|---|---|---|---|---|
| tgaaatgagggcttgcgaag | OCT4_1 | 1 | 2 | 50 | 1 |
| aaatccgaagccaggtgtcc | OCT4_2 | 2 | 61 | 55 | 2 |
| atcacctccaccacctggag | OCT4_3 | 3 | 95 | 60 | 3 |
| aggtccgaggatcaacccag | OCT4_4 | 4 | 138 | 60 | 4 |
| aggagggccttggaagctta | OCT4_5 | 5 | 161 | 55 | 5 |
| aatcccccacacctcagagc | OCT4_6 | 6 | 215 | 60 | 6 |
| atccccccacagaactcata | OCT4_7 | 7 | 253 | 50 | 7 |
| actagccccactccaacctg | OCT4_8 | 8 | 289 | 60 | 8 |
| tcaggctgagaggtctccaa | OCT4_9 | 9 | 322 | 55 | 9 |
| agttgctctcaccccgact | OCT4_10 | 10 | 354 | 60 | 10 |
| ttctccttctccagcttcac | OCT4_11 | 11 | 418 | 50 | 11 |
| ctcctccgggttttgctcca | OCT4_12 | 12 | 440 | 60 | 12 |
| ttctgcagagctttgatgtc | OCT4_13 | 13 | 466 | 45 | 13 |
| cttggcaaattgctcgagtt | OCT4_14 | 14 | 488 | 45 | 14 |
| tgatcctcttctgcttcagg | OCT4_15 | 15 | 510 | 50 | 15 |
| atcggcctgtgtatatccca | OCT4_16 | 16 | 533 | 50 | 16 |
| aaatagaaccccccagggtga | OCT4_17 | 17 | 560 | 50 | 17 |
| tcgtttggctgaataccttc | OCT4_18 | 18 | 582 | 45 | 18 |
| taagctgcagagcctcaaag | OCT4_19 | 19 | 612 | 50 | 19 |
| gcagcttacacatgttcttg | OCT4_20 | 20 | 636 | 45 | 20 |
| tccacccacttctgcagcaa | OCT4_21 | 21 | 661 | 55 | 21 |
| gattttcattgttgtcagct | OCT4_22 | 22 | 684 | 35 | 22 |
| tctgctttgcatatctcctg | OCT4_23 | 23 | 706 | 45 | 23 |
| actggttcgctttctctttc | OCT4_24 | 24 | 743 | 45 | 24 |
| ttgcctctcactcggttctc | OCT4_25 | 25 | 766 | 55 | 25 |
| ctgcaggaacaaattctcca | OCT4_26 | 26 | 788 | 45 | 26 |
| atctgctgcagtgtgggttt | OCT4_27 | 27 | 814 | 50 | 27 |
| atccttctcgagcccaagct | OCT4_28 | 28 | 851 | 55 | 28 |
| ttacagaaccacactcggac | OCT4_29 | 29 | 874 | 50 | 29 |
| tagtcgctgcttgatcgctt | OCT4_30 | 30 | 910 | 50 | 30 |
| ctcaaaatcctctcgttgtg | OCT4_31 | 31 | 932 | 45 | 31 |
| ctgagaaaggagacccagca | OCT4_32 | 32 | 954 | 55 | 32 |
| agaggaaaggacactggtcc | OCT4_33 | 33 | 976 | 55 | 33 |
| atagcctggggtaccaaaat | OCT4_34 | 34 | 1010 | 45 | 34 |
| agtacagtgcagtgaagtga | OCT4_35 | 35 | 1038 | 45 | 35 |
| ttcccccctcagggaaaggga | OCT4_36 | 36 | 1064 | 60 | 36 |
| tgacggagacagggggaaag | OCT4_37 | 37 | 1086 | 60 | 37 |
| agtttgaatgcatgggagag | OCT4_38 | 38 | 1116 | 45 | 38 |

Cell Culture

K562 cells were cultured in Dulbeco's Modified Eagle Medium (DMEM) (Gibco) supplemented with 10% fetal bovine serum (FBS) (Gibco). Purified RNA was extracted from K562 cells using RNA MiniPrep (Qiagen, USA).

CA1S hESCs (74, 75) were propagated in mTeSR (76) basal medium (STEMCELL Technologies, Inc., Vancouver, BC, Canada), additionally supplemented with antibiotic-antimycotic (100 U/mL penicillin, 100 mg/mL streptomycin and 0.25 mg/mL amphotericin B) (Invitrogen, Carlsbad, Calif., USA). Upon passaging, hESCs were washed with phosphate-buffered saline (PBS) prior to incubating with TrypLE Express (Invitrogen, Carlsbad, Calif., USA) at 37° C. for 10 minutes to detach single hESCs from 4-8 day-old cultures depending on confluency. TrypLE Express was neutralized with mTeSR supplemented with antibiotic-antimycotic and suspensions were then transferred into new tissue culture dishes containing a precoated layer of 1:30 diluted Matrigel (Becton Dickinson, San Jose, Calif., USA) and mTeSR supplemented with antibiotic-antimycotic. For differentiation, mTeSR was replaced with Dulbecco's modified eagle medium with 10% fetal bovine serum (FBS) 1 day after plating cells.

When harvesting hESCs for qRT-PCR, cells were incubated with TrypLE Express (Invitrogen, Carlsbad, Calif., USA) at 37° C. for 20 minutes in order to produce a more uniform single cell suspension from 4-8 day-old cultures.

Cryo-vials of primary cells isolated from a lobular breast cancer metastasis were provided by the BC Cancer Agency in accordance with ethical guidelines of the University of British Columbia. To increase viability, cells were transferred to fresh culture medium and incubated for 2 days before analyzing in the microfluidic device.

Transfer Efficiency Measurements

A solution containing 10 µM FAM-labeled 40-mer poly-A oligonucleotides (IDT, USA), 0.1% Tween 20, and ROX passive reference dye (from CellsDirect kit, Invitrogen, P/N 54880) diluted 100× was loaded into the cell capture chambers and sequentially pushed into the 10 nL and 50 nL chambers with water containing 0.1% Tween 20, and ROX reference dye diluted 100×. Fluorescence images acquired of FAM and ROX were used to measure the transfer of oligonucleotides from one chamber to the next. The transfer efficiency for each chamber was calculated as (Initial Signal−Final Signal)/(Initial Signal), where Signal=(FAM Intensity−FAM Background)/(ROX Intensity−ROX Background). A conservative estimate of the lower bound of transfer efficiency was taken to be one standard deviation from the mean measurement of transfer efficiency.

Cell Capture Measurements

A custom microfluidic device with a linear array of cell trap geometries was fabricated using protocols described above. The device was mounted on an inverted microscope (Leica DM IRE2) and imaged in bright field using a CCD camera (Hamamatsu ORCA-ER). The device was primed with 0.05% bovine serum albumen (BSA) (Gibco) in phosphate-buffered saline (PBS) (Gibco). Prior to loading in the device, cells were washed twice in fresh culture media (Dulbeco's Modified Eagle Medium (DMEM) (Gibco) supplemented with 10% Fetal Bovine Serum (Gibco)). After the final wash cells were resuspended to be at a concentration of 1 million per mL. Input sample viability was measured with the Cedex Automated Cell Counter (Roche innovatis AG).

To measure the capture efficiency, cells were pumped through the array using a downstream microfluidic peristaltic pump at a rate of approximately 1 nL/second and the number of cells that bypassed each trap before a successful trapping event was recorded. These counts were fit using a maximum-likelihood estimator for a geometric distribution with the fitdistr function (MASS package version 7.3-6) in R (version 2.11.1). Efficiencies are reported as the probability of a successful capture for each cell.

To measure cell viability after loading, cells were loaded into the array using pressure driven flow as described above until high trap occupancy was observed. 0.2% Trypan Blue (Gibco) in PBS was then flowed over the trapped cells. Viability was calculated as the number of unstained cells divided by the total number of cells.

Cell diameter was measured from Cedex images and images of cells trapped in the microfluidic device using ImageJ (version 1.43u). A two sample t-test was used to test the hypothesis that the resulting size distributions were significantly different. The assumption of equal variance was tested using an F test. For optimized cell trap geometries the cell trapping efficiency was improved to 87% by bringing the cup within one cell diameter of the focuser and by including a small bypass shunt through the cup, similar to the cup geometry presented in Skelley et al. (10).

Mixing by Diffusion

Mixing of solutions by diffusion was characterized in the microfluidic device by loading fluorescently labeled 40 bp poly-A oligonucleotides into the 10 nL chambers, and pushing the contents of the chamber into the adjacent 50 nL chambers. Time-lapse imaging was used to measure the evolution of the distribution of fluorescently labeled oligonuceotides in the PCR chambers over time (Figure S7). The standard deviation of the pixel intensities in each chamber through time was used as a metric of mixing. The resulting curves of all analyzed chambers (N=200) were each fit to a decaying exponential using least squares regression to determine the characteristic mixing time constant. This resulted in a mean mixing time of 15.2±1 minutes.

Using the Stokes-Einstein relation and assuming a random coil we estimate the diffusion constant of a 40 bp oligonucleotide to be:

$$D = \frac{K_B T}{6\pi\eta R} \cong \frac{K_B T}{6\pi\eta (Nd^2)^{1/2}},$$

where $K_B T$ is the thermal energy (4.1 pN·nm), $\eta$ is the fluid viscosity (~0.001 kg/m·s), d is the length of a DNA base pair (~3.3 Angstroms), and N is the number of base pairs. This yields a value of approximately $1.15 \times 10^{-10}$ m$^2$s$^{-1}$, which is comparable to the diffusion constant of polymerase, the largest molecule in the PCR mix. Since the template solution constitutes only ⅕ of the final PCR reaction it must diffuse the longest distance to equilibrate across the chamber. Therefore, the measured diffusion time of 15.2 minutes represents an upper bound to the time constant for complete mixing of all components.

Example 2.2: Precision and Sensitivity of Microfluidic RT-qPCR

Chamber volumes were designed to ensure sufficient dilution between each processing step to avoid reaction inhibition while at the same time maintaining high template concentrations and assay sensitivity.

Figure 13:
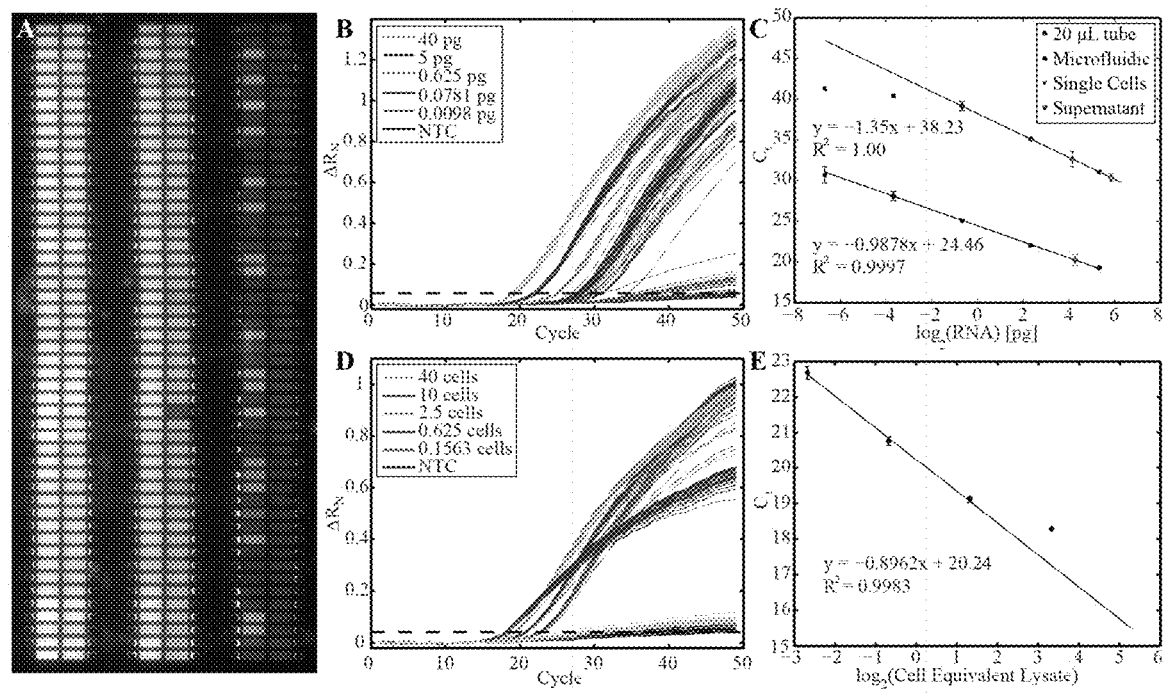
FIG. 13, panel A, is a fluorescence image of entire device of FIG. 12, panel A, showing 300 reactions in 6 lanes.

FIG. 13, panel A, is a fluorescence image of the entire device showing 300 reactions in 6 lanes, taken after 40 cycles of PCR from dilution series of purified total RNA from K562 cells. From left to right the samples are 40 pg/chamber, 5 pg/chamber, 625 fg/chamber, 78 fg/chamber, 10 fg/chamber, and no-template control (NTC). Single molecule amplification at limiting dilution results in a digital amplification pattern for 10 fg and 78 fg lanes. No amplification is observed in NTC lane (N=50). FIG. 13, panel B, shows 300 real time amplification curves generated from processing sequences of images similar to FIG. 13, panel A. The threshold for determining CT values is indicated by the dashed line. FIG. 13, panel C, depicts on-chip (lower) and off-chip (upper) RT-qPCR for GAPDH from a 8× serial dilution of purified total RNA shows improved sensitivity in nL volume reactions. In the microfluidic system, CT values for the 10 fg sample correspond to single molecule amplifications detected in 19 of 50 chambers. The mean and standard deviation from single cell measurements is shown in green for both on and off-chip analysis. CT values obtained on chip correspond to a mean of 20 pg of RNA per cell. Off-chip measurements of single K562 cells washed twice in PBS and isolated by glass capillary exhibit artificially increased levels due to residual signal from debris and free RNA in the supernatant. Cells were transferred in approximately 2 µL of supernatant, which was measured to contain ~20 pg of extracellular RNA. Error bars represent standard deviation of measured CT values for all amplified reactions. FIG. 13, panel D, shows the real-time amplification curves of GAPDH in K562 cell lysate dilutions. FIG. 13, panel E, shows the measured CT values for GAPDH in dilution series of cell lysate. No inhibition occurs for single cell lysates.

Cell lysate dilutions showed that reaction inhibition becomes significant at concentrations in excess of 0.2 cells/nL, or 10 cells per 50 nL reaction (FIG. 13, panel D). Experiments in tubes were performed to determine that a dilution ratio of at least 5:1 (PCR mix:RT product) is optimum for PCR efficiency. We therefore designed our combined reactors to have an aggregate total volume of 60.6 nL, consisting of a 0.6 nL cell capture chamber, a 10 nL RT chamber, and a 50 nL qPCR chamber. These volumes allow for the reliable amplification of single molecules (FIG. 13, panel A), and result in a final template concentration of 330 ng/mL when starting from a single cell equivalent of RNA (20 pg). The use of larger volume RT and PCR chambers has the added advantage of reducing their surface to volume ratio, thereby minimizing reagent evaporation through the gas permeable device material (polydimethylsiloxane).

Figure 14:
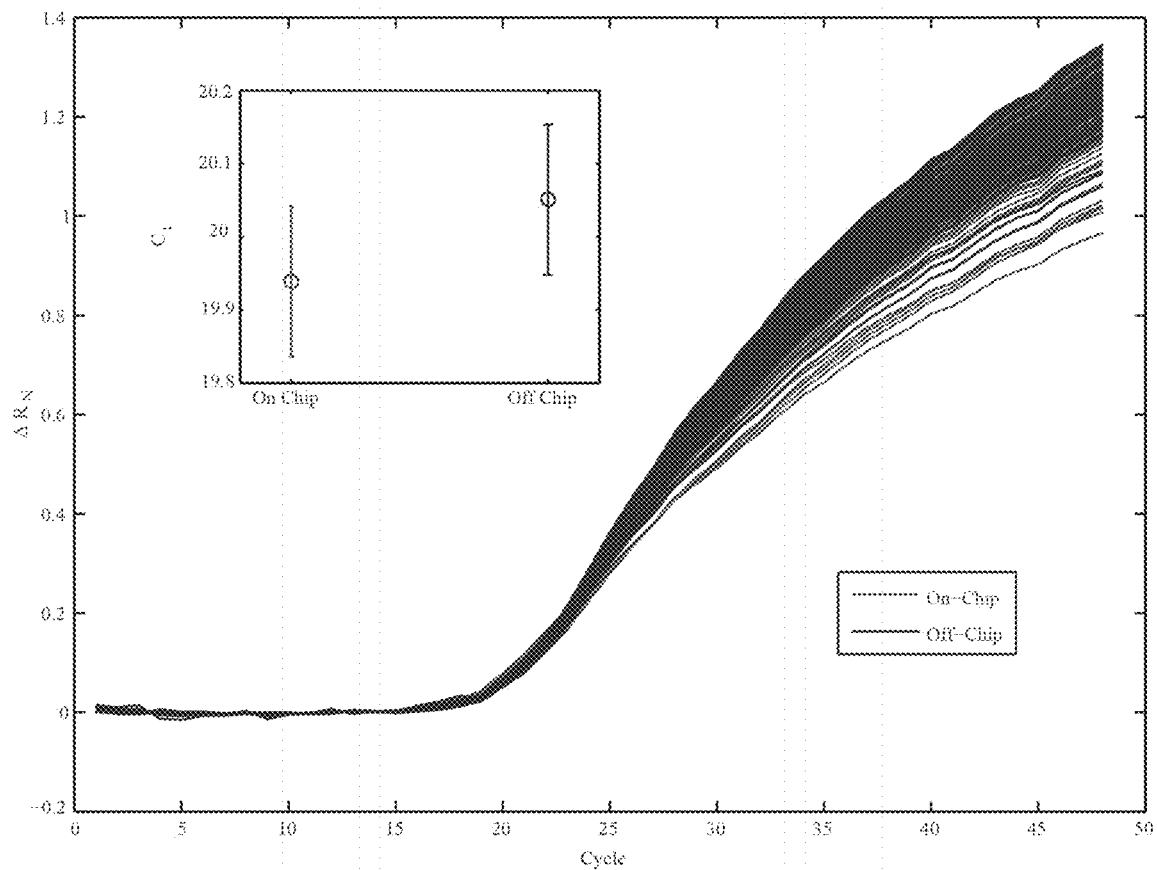
FIG. 14 is a graph comparing GAPDH measurements from K562 cell lysate with RT performed in the microfluidic device of FIG. 12, panel A, or RT performed in tubes prior to qPCR in the device.

The sensitivity and precision of RT-qPCR in the device was tested by performing measurements of GAPDH expression over an 8-fold dilution series of total RNA, ranging from 40 pg (~2 cell equivalents) to 10 fg (~1/2000 cell equivalents). RNA was purified from K562 cells, a BCR-ABL positive human cell line derived from a patient with chronic myeloid leukemia (77) (FIG. 13, panels A-C). The efficiency of amplification was determined over the four highest template concentrations (40 pg, 5 pg, 625 fg, 78.125 fg) as the slope from a linear least squares fit of log 2(C) vs. CT, and was found to be 0.988±0.055. The standard deviation of CT values was less than 0.15 at the three highest concentrations (s.d.=0.08, 0.10, 0.14 for the 40 pg, 5 pg, and 625 fg samples respectively), indicating uniform amplification across the array and technical error of less than 10% in absolute concentration, near the limit of qPCR precision. The highest measurement variability was observed in the 78 fg sample, where shot noise (Poisson sampling noise) is most pronounced and accounts for approximately 50% of the measurement variance. Template amounts below 625 fg resulted in a digital pattern characteristic of single molecule amplification (49/50 for 78 fg, 19/50 for 10 fg) and consistent with the expected occupancy of chambers as determined by a binomial distribution (2). Based on the frequency of single molecule detection in the 10 fg sample, we measured the average copy number of GAPDH to be 979±240 transcript copies per single cell equivalent (20 pg) (FIG. 13). A comparison of CT values obtained from on-chip qPCR from cDNA synthesized off-chip demonstrated that on-chip RT efficiency is equal to that obtained off-chip when working from the same RNA concentrations. FIG. 14 shows a comparison of GAPDH measurements from K562 cell lysate with RT performed in the microfluidic device or RT performed in tubes prior to qPCR in the device. Obtained CT values (inset) show no significant difference in efficiency. Finally, comparison of the same dilution series of RNA, assayed for GAPDH both on-chip and in tubes (20 µL volume) (FIG. 13, panel C), showed that on-chip analysis provides improved sensitivity.

Example 2.3: Cell Capture

Figure 15:
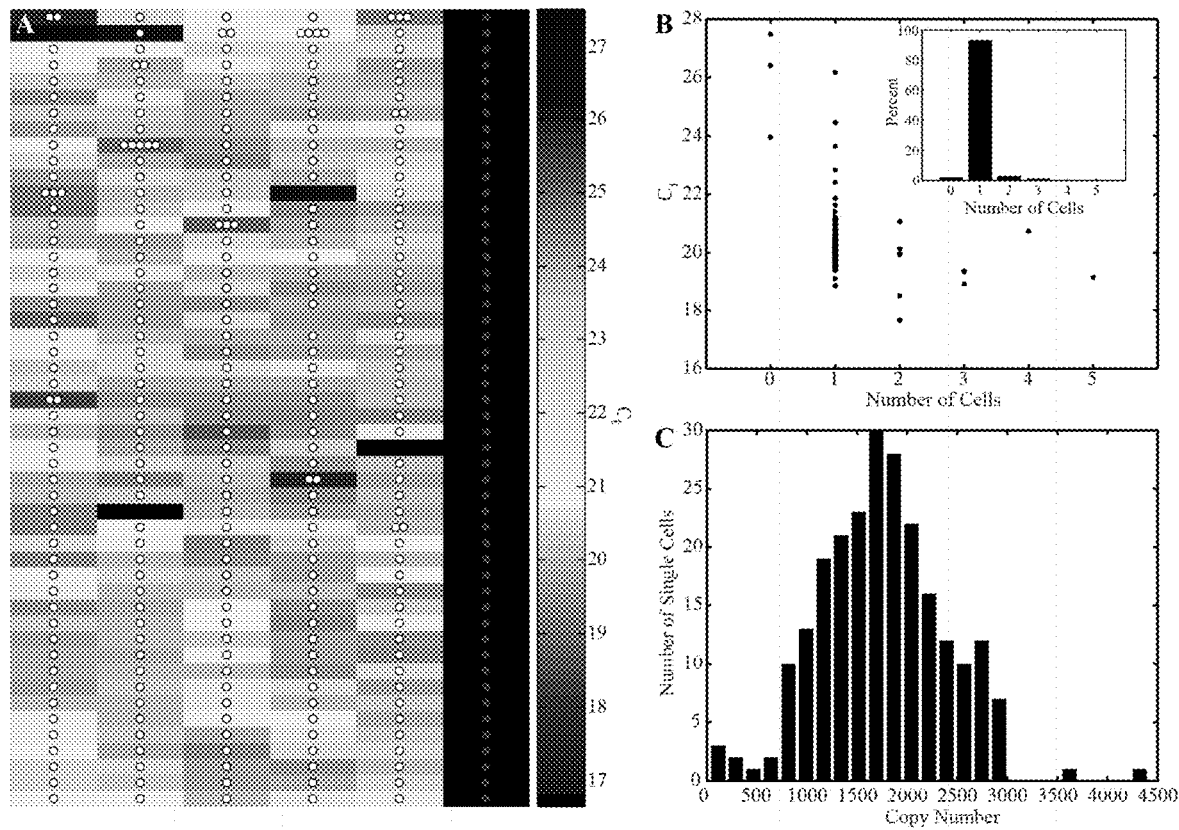
FIG. 15, panel A, is schematic drawing of the locations of cells in each chamber along all 6 lanes of a device of FIG. 12, panel A.
Figure 16:
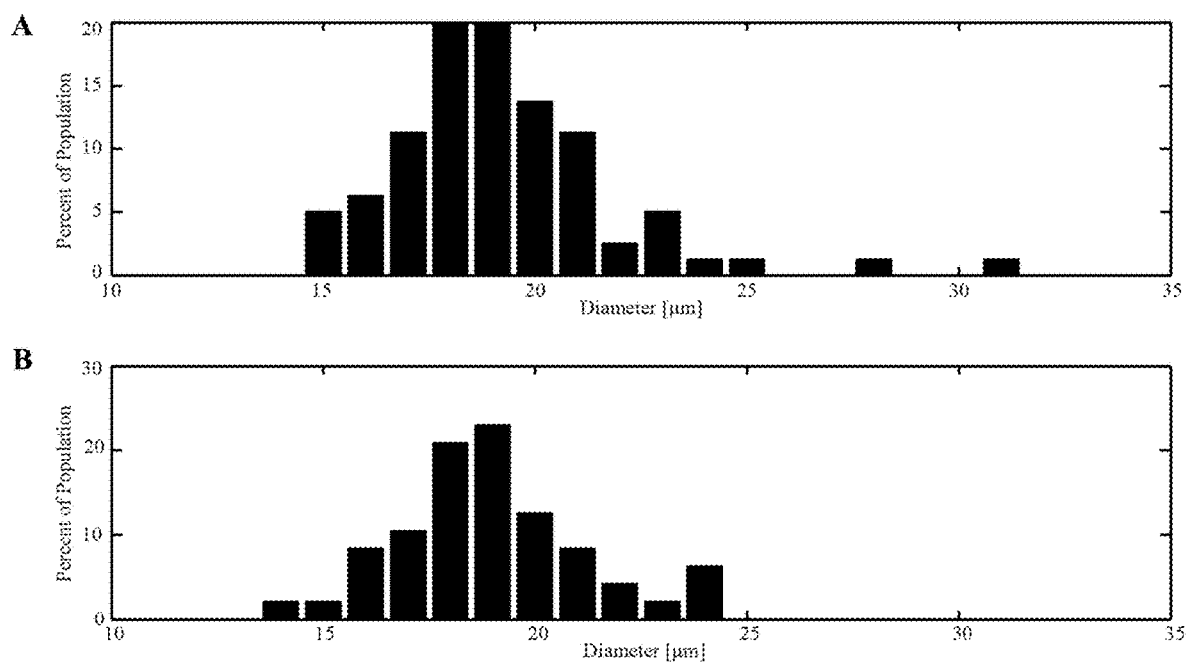
FIG. 16, panel A, is a histogram showing the size distribution of cells in original sample as measured by Cedex.

Cell capture chambers incorporated funnels (deflectors) located 22.5 µm from the trap, to focus cells into the central streamlines where capture is most efficient (FIG. 12, panel C,). Using these structures a high single cell occupancy of array locations was achieved (FIG. 15, panels A and B). Over 8 separate experiments, a loading protocol of ~60 seconds (106 cells/mL, 20 nL/s per lane) resulted in the successful isolation of single cells in 1518/1700 chambers (89.3%), with a cell capture efficiency of 5.0±0.5%. Staining with Trypan Blue™ was used to assess the viability of cells after loading and was determined to be equivalent to the viability of the input sample (97.4% viability vs. input 96.8%). Finally, measurements of the distribution of cell diameters prior to and after loading indicated that cell trapping did not introduce significant bias (p=0.67, two sample t-test) in selecting cells of different sizes FIG. 16 provides histograms showing the size distribution of cells in original sample as measured by Cedex (FIG. 16, panel A) are consistent with the size distribution of cells isolated by microfluidic traps (FIG. 16, panel B), with the assumption of spherical cell shape the distribution of diameters of trapped cells corresponds to a mean volume of 4.2 pL with a standard deviation of 2.0 pL. This cell trap geometry and loading protocol were used in all subsequent qPCR measurements presented below. Further improvement of trap and funnel (i.e deflector) geometries were found to achieve fill factors of >99% (100 single cells captured out of 100 traps analyzed) and cell capture efficiencies of 87.0±4.5%, with cell viability again matching the input sample (>98%) and not significantly biasing cell sizes (p=0.35, two-sample t-test), making this method applicable to the analysis of limited quantity samples such as rare stem cells or clinical samples.

FIG. 15, panel A, shows the locations of cells in each chamber along all 6 lanes of a device, as determined by brightfield microscopy, are represented as white circles and overlaid on a heat map of CT values obtained from RT-qPCR measurements of GAPDH in K562 cells. Dark circles indicate NTC. FIG. 15, panel B, is a scatter plot showing CT measurements for experiment shown in FIG. 15, panel A. The histogram on the inset shows 93.2% single cell occupancy. FIG. 15, panel C, shows the distribution of the number of GAPDH transcripts measured in single K562 cells (N=233).

Example 2.4

Figure 17:
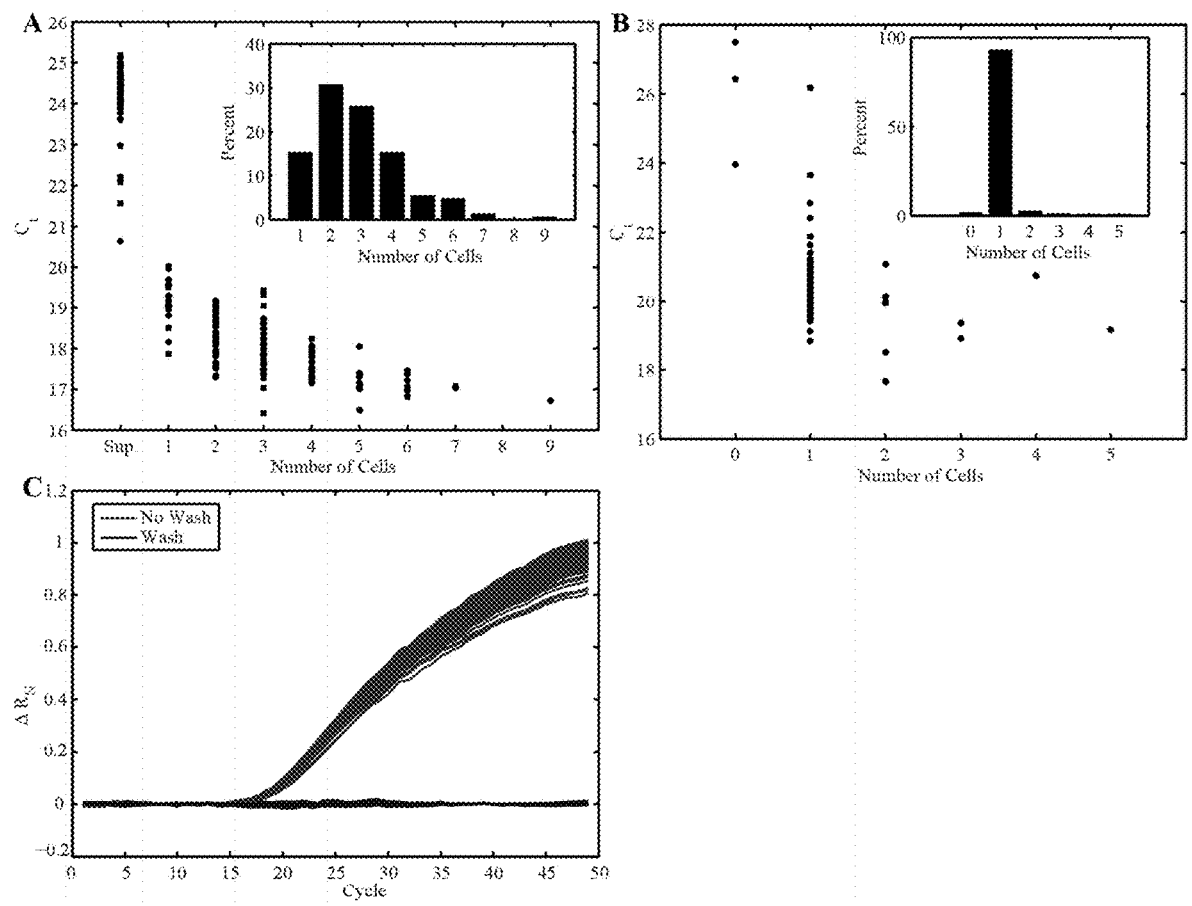
FIG. 17, panel A, is a scatterplot of GAPDH measurements in cells washed in PBS off-chip prior to injection into microfluidic device.
Figure 18:
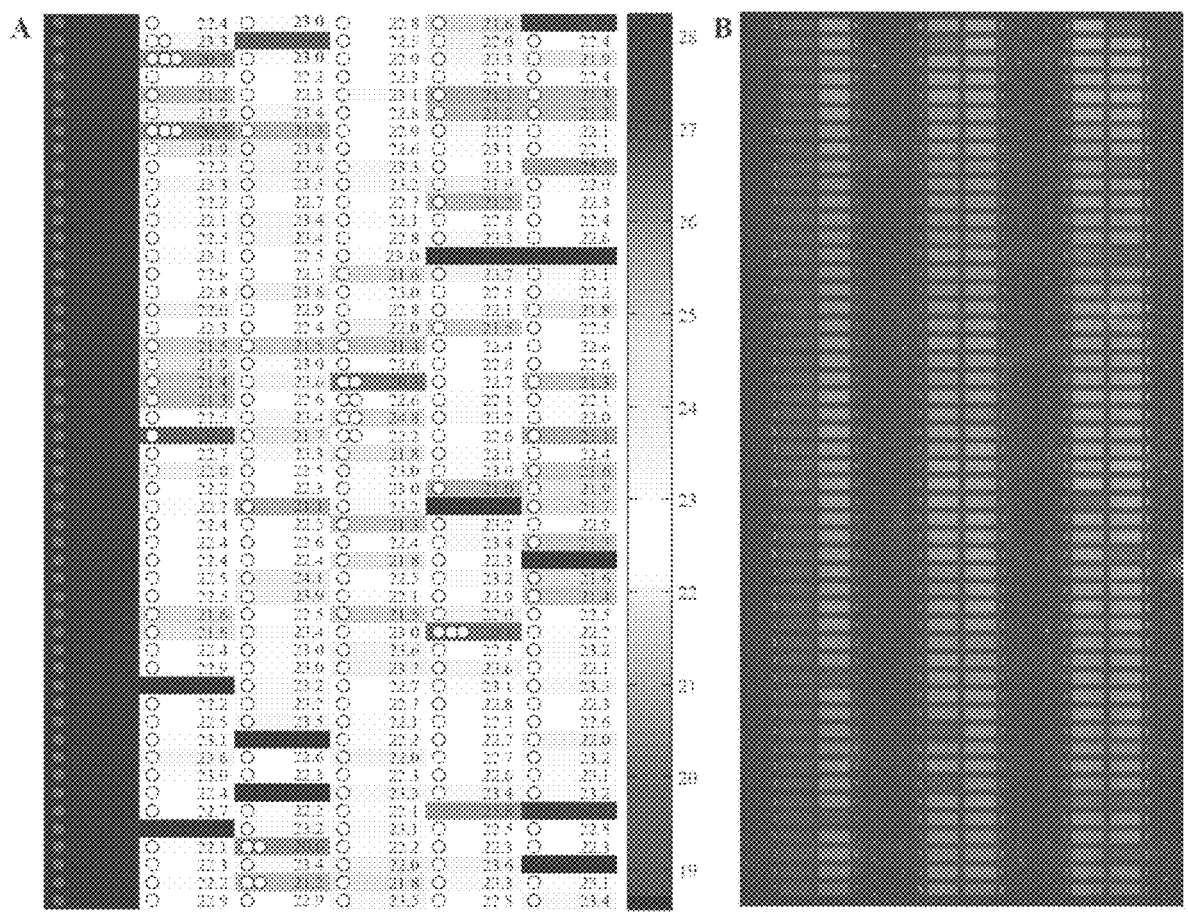
FIG. 18, panel A, is a schematic diagram of the locations of cells in each chamber along all 6 lanes of a device.

The immobilization of cells in traps in cell capture chambers was also used for on-chip washing of cells prior to lysis to remove free RNA, cellular debris, and untrapped cells that would otherwise give rise to background signal or result in low single cell occupancy. FIG. 17, panel A, provides measurements of GAPDH in cells washed in PBS off-chip prior to injection into microfluidic device, without an on-chip wash contain background signal from template in supernatant. Without on-chip washing, untrapped cells remain in the capture chambers, resulting in fewer single cell measurements (histogram inlayed). As shown in FIG. 17, panel B, on-chip washing was found to reduce the background signal from free RNA in the supernatant, and dramatically increased the number of single cells analyzed. As seen in FIG. 18, detection of residual RNA after washing is dramatically reduced by comparison to off-chip results due to small volume processing. FIG. 18, panel A, depicts the locations of cells in each chamber along all 6 lanes of a device, as determined by brightfield microscopy, and represented as white circles and overlaid on a heat map of CT values obtained from RT-qPCR measurements of miR27a in K562 cells. Shaded circles indicate NTC. FIG. 18, panel B, is a fluorescence image of the entire device corresponding to experiment depicted in FIG. 18, panel A, after 30 PCR cycles. Cell corpses remain after heat lysis and are visible as punctuate fluorescent spots adjacent to reaction chambers.

FIG. 17, panel C, provides a comparison of GAPDH measurements from loading purified RNA and washing, or not washing, the cell capture chambers. The efficiency of chamber washing, determined by loading purified RNA template (36.5 ng/mL), followed by washing and RT-qPCR analysis, was >99.99% (1.1'104 copies measured without wash, 0 copies detected after washing). In addition, RT-qPCR measurements testing different cell loading and washing protocols demonstrated that on-chip washing allows for loading directly from culture medium with low background as compared to off-chip wash steps followed by analysis in μL volumes (FIG. 17, panel C). Importantly, on-chip washing allows for lysis within seconds of washing, thereby minimizing spurious transcriptional responses that may arise from sequential medium exchange and spin steps.

Example 2.4

Figure 19:
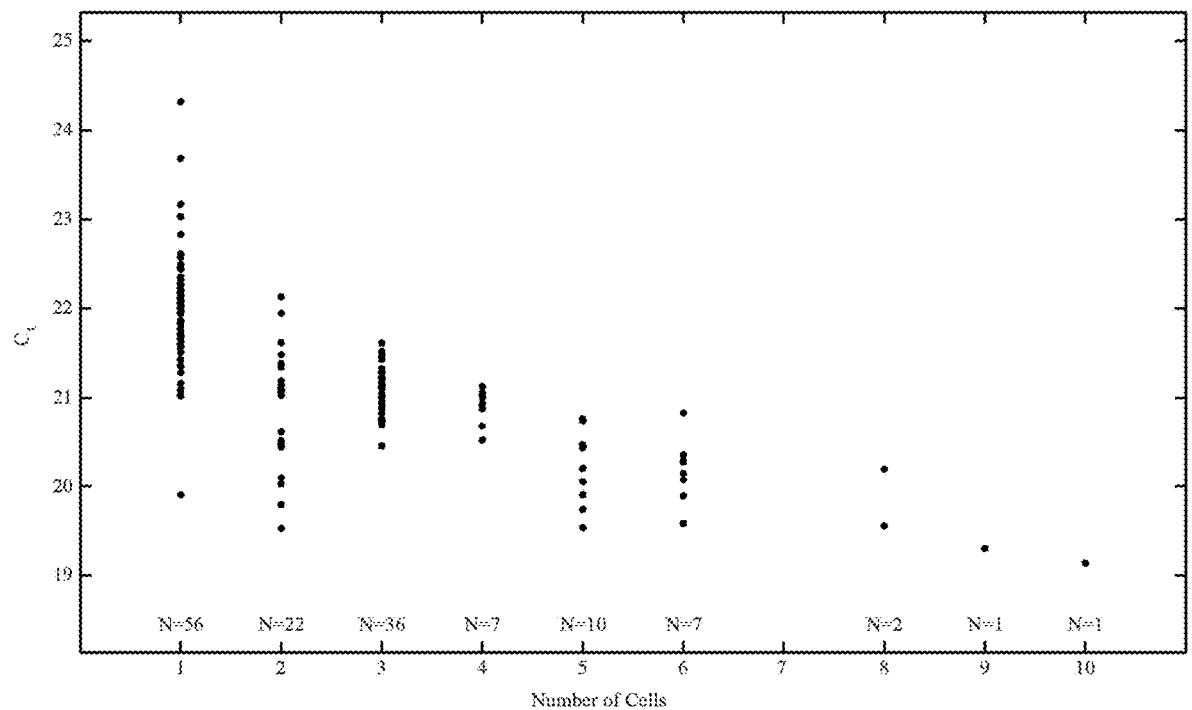
FIG. 19 is a scatterplot of miR16 measurements in hESC cell aggregates.

The efficiency and reliability of on-chip cell processing was evaluated by comparing the GAPDH measurements of purified RNA to measurements performed directly from single K562 cells (FIG. 13, panel C, FIG. 15, panel C). K562 cells were loaded directly from culture medium followed by washing and analysis using a chemical lysis and one-step RT-qPCR protocol (Cells Direct™, Invitrogen). Using a CT threshold of 31.5, corresponding to the mean CT of a single molecule of GAPDH (CT=30.5) plus two standard deviations (s.d.=0.5), successful amplification was observed in 100% of single cells (N=233) (FIG. 15, panels A-B). Adjacent chambers that did not contain a cell were distinguishable from single cell measurements with an average delta CT value of 5.7 (5 empty chambers, 3 of which amplified) (FIG. 15, panels A-B). A log-normal distribution of GAPDH in single cells was observed with mean CT values of 20.3 (s.d.=0.8) and an average of 1761 (s.d.=648) copies per cell (FIG. 15, panel C). Additionally, the mean CT of 20.3 observed for single cells matches measurements of single cell equivalent lysate (CT=20.2, FIG. 13, panel D). Using digital PCR on cDNA prepared from K562 cell lysate, an average of 1229±72 GAPDH molecules per single cell equivalent was measured. Finally, as expected, RT-qPCR measurements from chambers loaded with more than one cell show reduced variability and lower CT values (FIG. 16, panel A, FIG. 19). AS shown in FIG. 19, measurement of miR16 in hESC cell aggregates demonstrates that the number of cells is reflected in corresponding cycle threshold (CT) values.

Example 2.5 Application to Measurement of Single Cell miRNA Expression

The technology was next applied to the study of single cell miRNA expression. The short length of miRNAs (~22 nucleotides) makes them difficult to detect by hybridization approaches, so that RT-qPCR is the dominant quantification strategy. To demonstrate the robustness and throughput of this technology, a total of 1672 single cell measurements were performed to examine single-cell variability in the expression of 9 miRNAs spanning a wide range of abundance (>16000 copies per cell to <0.2 average copies per cell). K562 cells were again chosen as a heterogeneous population for this study since they are known to exhibit mixed characteristics of erythrocytes, granulocytes, and monocytes (77, 78). The expression of miR-16, a highly expressed microRNA that is found in many tissue types (79), was evaluated as an internal standard for normalization (57). miR-16 was log-normally distributed across K562 cells, but with slightly lower expression and notably tighter regulation than GAPDH, having an average of 804 (s.d.=261) copies per cell and a standard deviation of 30% (mean CT=21.4, s.d.=0.4). Matched experiments on single cells, isolated by micropipette into 20 μL volume tubes, displayed an increase in measurement variability to ~90% (mean CT=29.5, s.d.=0.9), demonstrating the improved precision of parallel microfluidic cell processing in nL volumes (FIG. 20, panel A). The observed shift in mean CT values between on and off-chip measurements is due to lower template concentrations, and hence increased required PCR cycles, in the off-chip samples.

(C) (D) 2072 single cell measurements of the expression of 9 miRNA in K562 cells. Reflected histograms represent the expression distributions for each miRNA.

To demonstrate the utility of this device for measuring differential expression in single cells, the expression of miR-223, a miRNA implicated in myeloid differentiation, was measured. In contrast to miR-16, K562 cell miR-223 expression was found to be highly variable (mean CT=22.2, s.d.=1.6, copy number=513, s.d.=406) and was not log-normally distributed (FIG. 20, panel B; the right-most bar indicates cells for which miR-223 was not detected (ND)), consistent with the known functional heterogeneity of K562 cells. These measurements highlight the utility of single cell miRNA expression analysis for assessing the heterogeneity of cell populations and for identifying miRNAs that are useful biomarkers of cellular state. To further explore this possibility, the expression of an additional 7 miRNAs (9 total) was measured, and the patterns of single cell expression in K562 populations were plotted. FIG. 20, panel C, shows mean single cell miRNA copy numbers measured by RT-qPCR in the microfluidic device compared to digital PCR measurements from bulk cell lysate. Error bars represent standard deviation of single cell measurements for each miRNA. Following the procedure described above, single molecule CT values obtained by digital PCR were used to translate measured CT values to absolute copy number. Assuming 100% efficient amplification, the copy number, calculated as 2(CT (single cell)−CT (single molecule)), was observed to correlate well (coefficient of 0.9932) with the average copy number obtained by digital PCR of cDNA prepared from bulk lysates. FIG. 20, panel D, shows 2072 single cell measurements of the expression of 9 miRNA in K562 cells. Reflected histograms represent the expression distributions for each miRNA.

Single cell measurements revealed distinct patterns of miRNA expression, with miR-16, miR-92, and miR-17-5p each exhibiting unimodal and tightly regulated distributions, while miR-223, miR-196a, and miR-145 showed multimodal distributions and a high level of cellular heterogeneity. For the lowest abundance miRNA, miR-200a, expression was detected in only a small fraction of cells and at levels below ~5 copies per cell. The average miR-200a copy number over all cells was within factor of two of that obtained by digital PCR (0.2 copies per cell). In contrast, miR-92 was found to be the most abundant miRNA and was present at approximately 60,000 copies per cell. These measurements established miRNA quantification in single cells with a dynamic range of greater than 104 and at single molecule sensitivity.

To illustrate the utility of single cell measurements in precisely assessing differences in both the average expression and the heterogeneity between two different cell populations, the expression levels of miR-16 and miR-223 in K562 cells were compared to those in CA1S cells, a human embryonic stem cell line (hESC). Although miR-16 was found to be expressed in hESC at similar levels to K562 ($\Delta CT=0.6$), approximately a two-fold greater variability in expression was observed (mean CT=22.0, s.d.=0.7) (FIG. 20, panel A). In contrast, when compared to K562, single CA1S cell measurements of miR-223 showed strong down-regulation, with miR-223 detected in only 3.6% of cells.

Example 2.6: Co-Regulation of miR-145 and OCT4 in Single Cells

Figure 21:
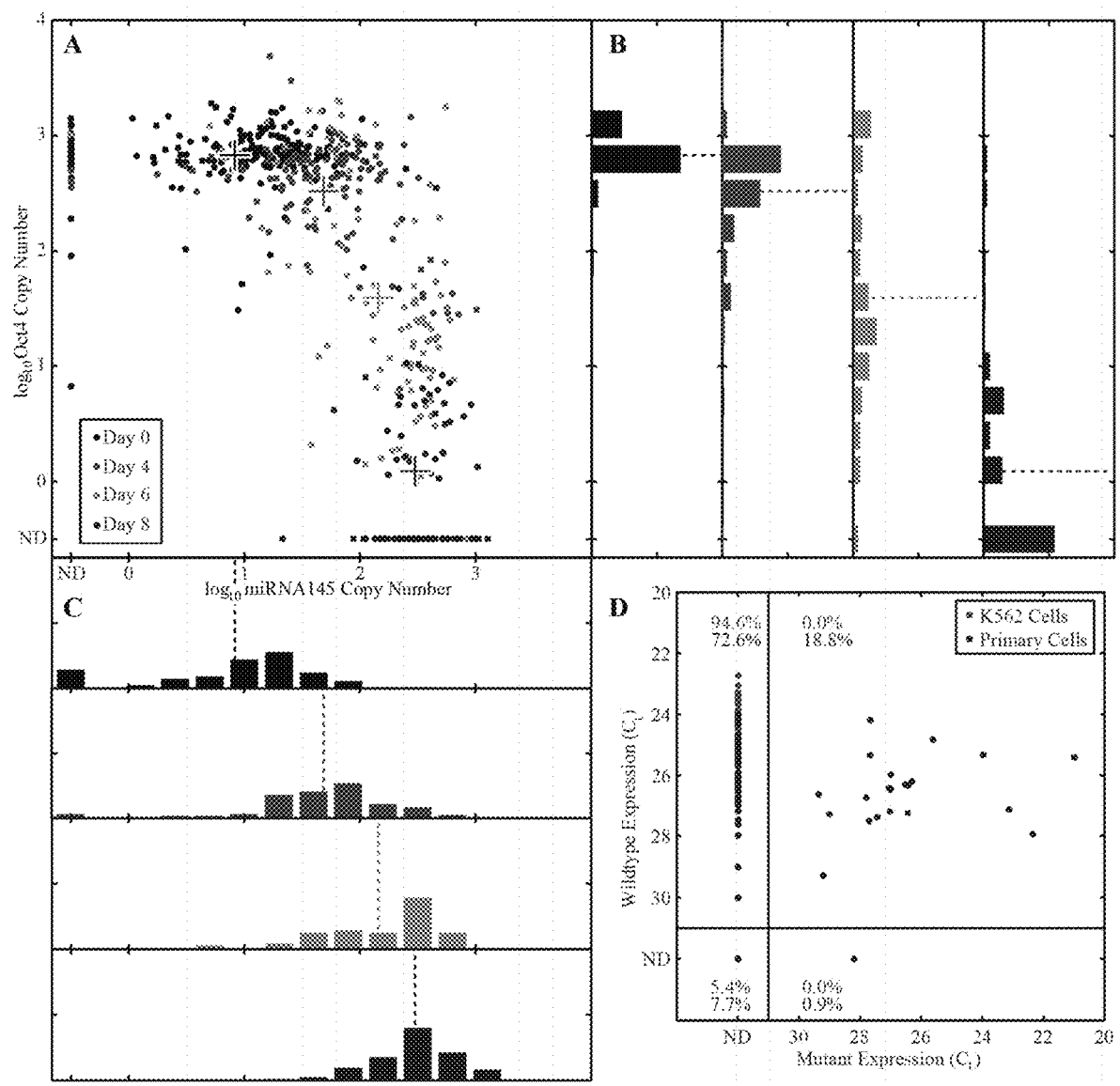
FIG. 21, panel A, is a histogram of single cell measurements of miR-16 expression in K562 cells and hESCs.
Figure 22:
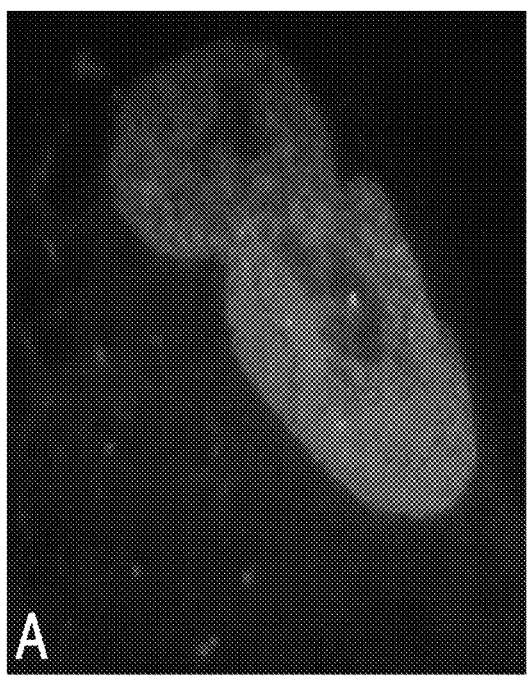
FIG. 22, panel A, is a representative image of mRNA-FISH of OCT4 in a CA1S cell after 7 days of FBS differentiation.
Figure 22:
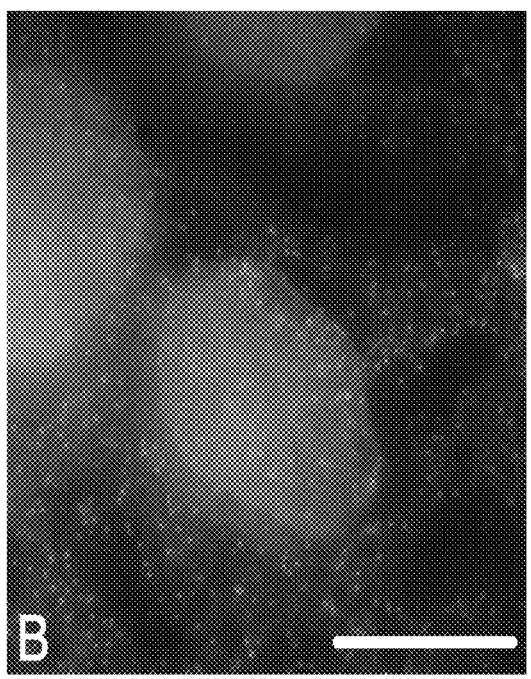

The measurement of multiple transcripts in single cells allows for quantitative measurements of gene co-regulation that would otherwise be masked by cellular heterogeneity. To demonstrate this capability, an optically multiplexed single cell RT-qPCR assay was conducted to study the co-regulation of miR-145 and OCT4, a known target of miR-145, during the differentiation of hESCs (FIG. 21, panels A-C). FIG. 21, panel A, is a scatterplot of a multiplexed analysis of the co-expression of OCT4 and miR145 in differentiating hESC. Points are color-coded to represent single cell measurements (N=547) for each time point. Crosses represent population mean copy number. FIG. 21, panels B and C, are histograms showing the distribution of each transcript are projected on the axes with the mean copy number indicated by a dashed line. A total of 1094 single cell measurements were performed at 0, 4, 6, and 8 days of differentiation. Cell distributions at each time point were used to map out the evolution of these transcripts and showed that average miR-145 levels increased approximately 20 fold (copy numbers: DO: mean=18.9, s.d.=25.5, D8: mean=380.3, s.d.=259.4) over 8 days. Increases in miR-145 were accompanied by progressive down-regulation of OCT4, ultimately reaching an average of 30-fold suppression (copy numbers: DO: mean=755.7, s.d.=306.4, D8: mean=27.8, s.d.=124.5) after 8 day. This was independently verified by mRNA-FISH, as shown in FIG. 22 images of mRNA-FISH of OCT4 counterstained with DAPI in CA1S cells. FIG. 22, panel A, is a representative image of mRNA-FISH of OCT4 in a CA1S cell after 7 days of FBS differentiation. The estimate of average copy number of OCT4 mRNA as determined by manual inspection of image stacks is 42 (s.d.=41, N=6). FIG. 22, panel B, is a representative image of undifferentiated CA1S cells. The estimate of average copy number as determined by manual inspection of image stacks is 988 (s.d.=368, N=6). The scale bar=10 am.

Notably, single cell analysis at day 6 showed a bimodal distribution in both OCT4 and miR-145, revealing a transition of cellular state. Without wishing to be bound by hypothesis, it is believed that this likely reflects the spontaneous differentiation of a subpopulation of cells. The observed single cell dynamics of miR-145 and OCT4 co-regulation are not apparent in population measurements, highlighting the use of scalable single cell transcriptional analysis in correlating molecular signatures to cellular decision making.

Example 2.7: SNV Detection in Primary Cells

To establish the specificity of the method, multiplexed measurements of mRNA single nucleotide variants (SNV) were used to assess the genomic heterogeneity within a primary tumor sample. A total of 117 single cells isolated from a plural effusion of a metastatic breast cancer were assayed for the expression of a SNV mutant of the transcription factor SP1, previously identified by deep sequencing (73) (FIG. 21, panel D). Primers were designed using sequences flanking the SNV location and do not discriminate between the genomic DNA and mRNA transcript. Of the 117 primary cells analyzed, 22 (18.8%) were heterozygous for the mutant and wildtype allele, 85 (72.6%) were homozygous wildtype, 1 (0.9%) was homozygous mutant and the transcripts were undetected in 9 (7.7%). The SP1 mutation was not detected in 37 control K562 cells, and the wild-type transcript was not detected in only 2 of these cells. In the absence of copy number alterations in the primary sample, these observed frequencies would suggest a mutant to wild-type SP1 ratio of 11.2% ($18.8\times1+0.9\times2=20.6$ mutant to $18.8\times1+72.6\times2=164$ wild-type). However, using digital PCR on purified DNA from the primary sample, the ratio of mutant to wild-type SP1 alleles was found to be 18.7±2.3%, in agreement with the previously reported ratio of 21.9%, obtained by deep sequencing (73). Given that the frequency of tumor cells within the original sample was approximately 89% (73), both DNA molecule counting and single cell RNA expression measurements show that the metastasis of this tumor is derived from multiple cancer cell lineages.

Example 3 Library Construction

A K52 cell suspension was loaded directly into a microfluidic device as previously described. Captured cells immobilized in the traps were washed with PBS solution for 10 min at 3 psi. Chambers containing single cells were isolated by actuation of valves, heat lysed (85 deg 5 min) and filled via a second inlet in the cell capture chamber upstream of the cell trap, with a first reaction mix comprising 3' miRNA adapters for ligation.

Next, a ligation mix that ligates 5' DNA adapters to the 5' end of miRNAs was added through the second inlet. An interface valve between the cell capture chamber, containing the lysed cell and the first reaction mix, and a larger first auxiliary chamber was opened, allowing the contents of the cell capture chamber to be flushed into the first auxiliary chamber along with the ligation mix under 5 psi of pressure.

Following ligation in the first auxiliary chamber, a cDNA synthesis mix was added via the second inlet to synthesize cDNA from the 5'adapter-miRNA-3'adapter molecules. An interface valve between the first auxiliary chamber, containing the lysed cell and the first reaction mix and ligation mix) and a larger second auxiliary chamber was opened to allow the contents of the second auxiliary chamber to be flushed into the second auxiliary chamber with the cDNA synthesis mix under 5 psi of pressure. Following cDNA synthesis, the reaction products were eluted through an elution port with 5 uL of fresh PCR mix for cDNA amplification, and subsequent high throughput sequencing on an Illumina sequencing instrument.

Figure 23:
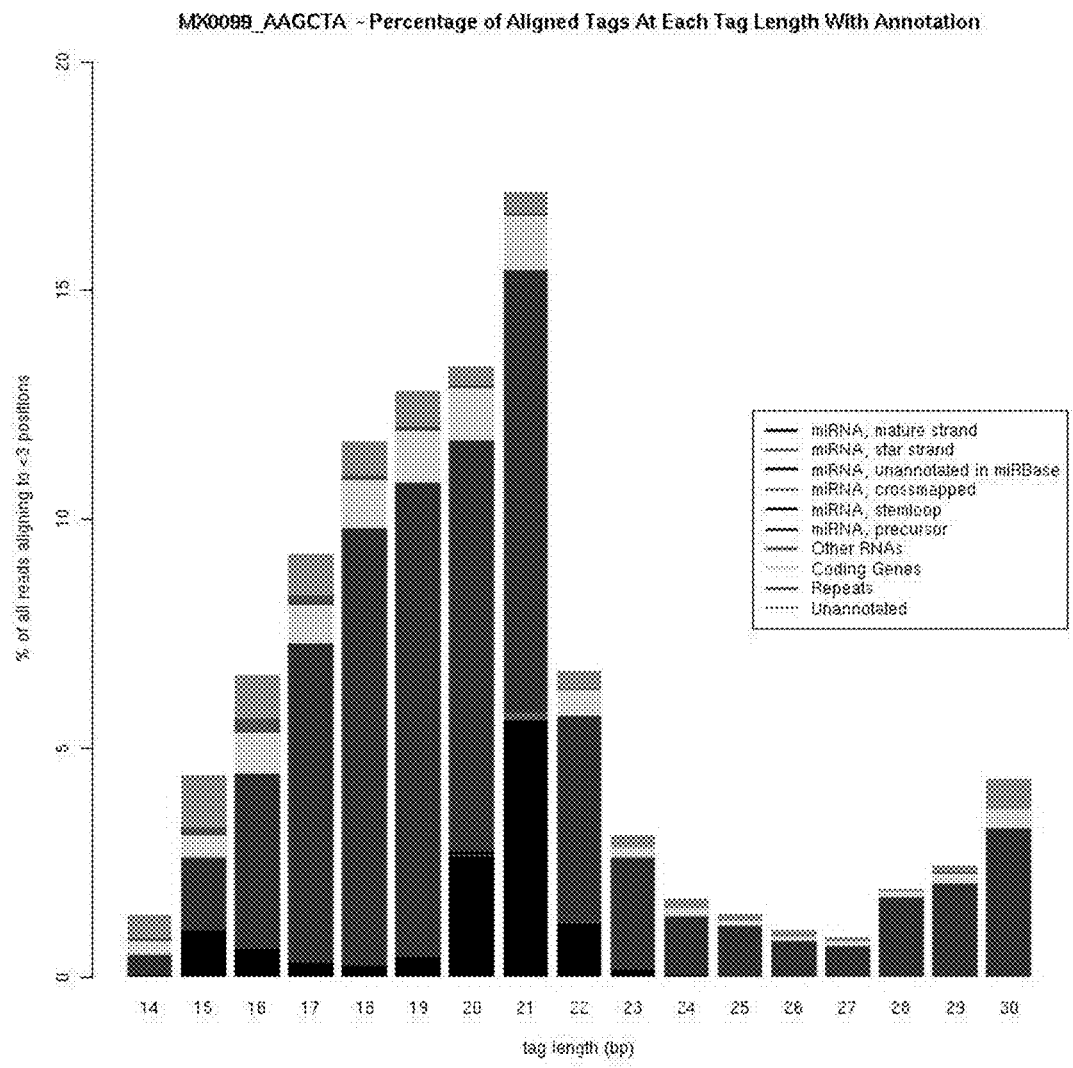
FIG. 23 is a histogram showing the percentage of aligned tags at each tag length in a miRNA sequence tag library constructed according to one embodiment of the invention.

Sequencing identified a number of RNA species (FIG. 23), including a high percentage of miRNAs. The miRNA species found in one single cell is listed in Table. In total, 11 single cells were processed in a single microfluidic device along with positive (purified RNA) and a negative (no cell) controls.

Example 4

Figure 24:
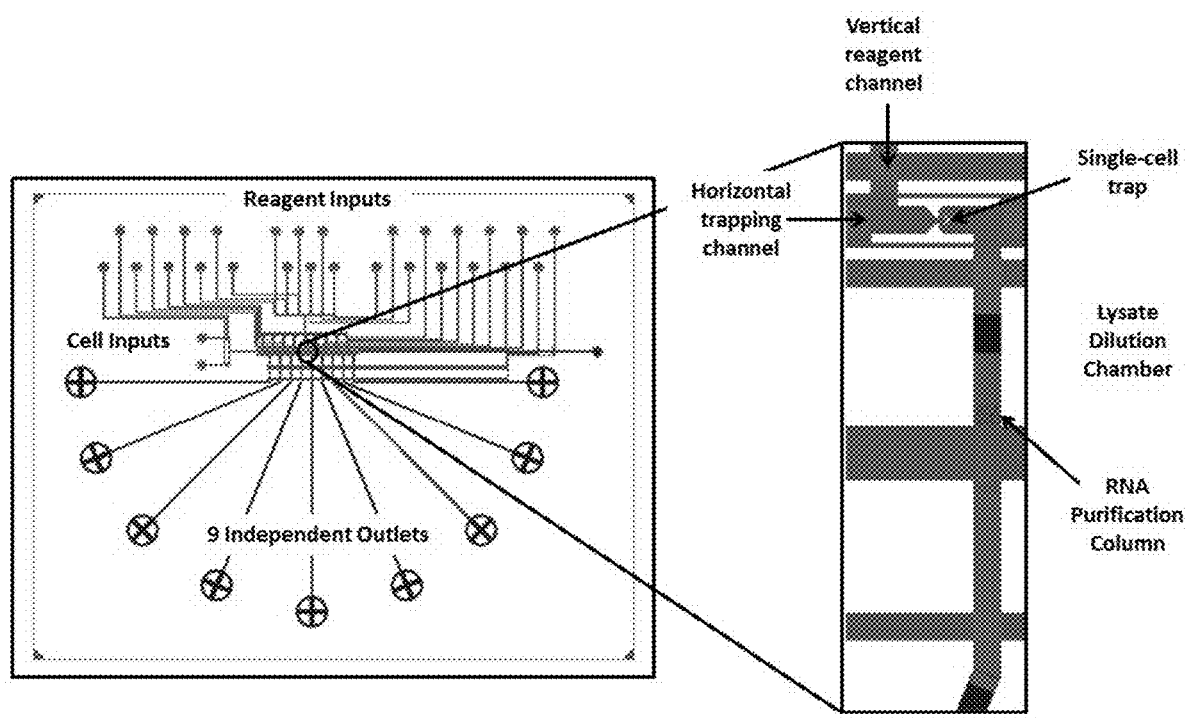
FIG. 24 is a schematic diagram of a microfludic device for sequencing and characterizing a single cell transcriptome according to one embodiment of the invention.

A microfluidic chip consisting of two fluidic paths was designed for sequencing and characterizing individual transcriptomes (FIG. 24). The first path leads from an inlet port, through a horizontal channel containing eight hydrodynamic cell traps, to an outlet. The horizontal channel can be partitioned to isolate the eight traps into eight individual cell capture chambers and one, equivalent volume, empty chamber for use as a control. The second fluidic path leads from second "reagent" inlets at the top of the chip and flows vertically down the chip into a series of nine reaction columns. Each columns intersects a partitioned cell capture chambers, or the control volume, and then flows through a sieve valve to an individual outlet port. A sieve valve is a "leaky" valve, allowing fluid to flow through, but stopping larger objects, such as RNA capture beads.

This chip is able to perform single-cell capture, lysis, mRNA purification and reverse-transcription. Briefly, mRNA capture beads are loaded through the reagent inlets and stacked against the sieve valves. A set of valves is then closed to isolate and protect the stacked columns. Next, cells are introduced through the horizontal channel and flowed until each cell trap has been filled, after which time the cells can be washed with clean buffer run through the horizontal channel. The cell capture chambers are then partitioned to isolate the cells, and the chip is transferred to flat-bed thermocycler for a heat lysis. The vertical path is then opened, and the lysate is passed over the bead columns, capturing the mRNA. As the lysate passes from the cell capture chamber to the column, it flows through a lysate dilution chamber. This chamber is important as pure lysate contains proteins and other material which can aggregate and clog the bead column. This dilution steps serves to avoid this. Once capture is complete, the chip is again incubated on a thermocycler, and reverse transcription mix introduced through the reaction inlet and flowed over the column. Finally, the sieve valve is opened, and beads, with cDNA now bound to them, are flowed to their respective outlet ports. The cDNA can then be used for PCR amplification and subsequent sequencing. In addition, random sequences can be incorporated on the capture beads, resulting in each captured mRNA molecule being given a unique barcode. As a result, the sequencing data can be used as a digital count of transcript abundance.

Results from the characterization of four cells in this way are presented in Tables 3 and 4. Table 3 is shown in FIG. 32.

Example 5

Figure 25:
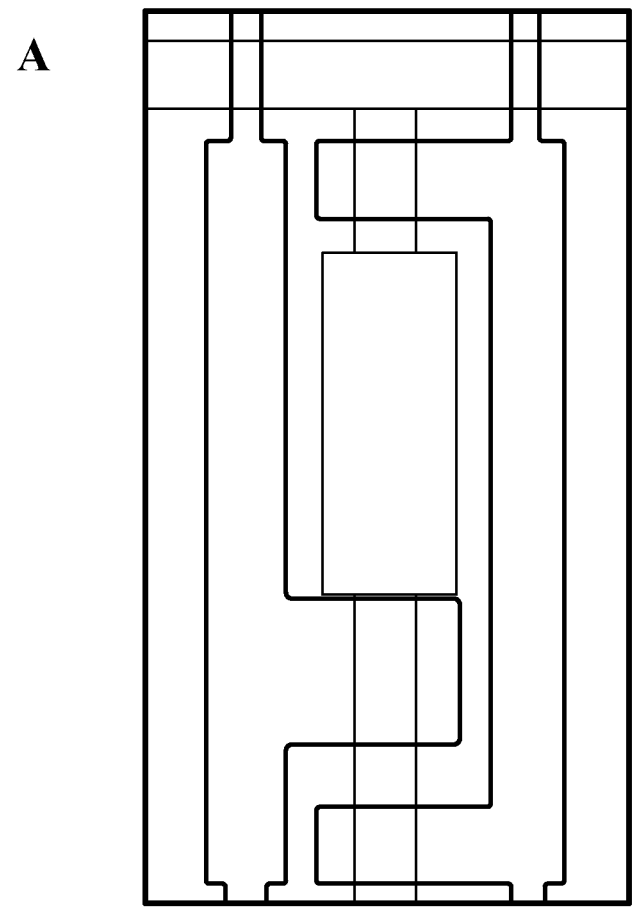
FIG. 25, panel A, is an image illustrating the mixing of functionalized beads and a cell for the purpose of purifying and immobilizing template (RNA) according to an embodiment of the invention.
Figure 25:
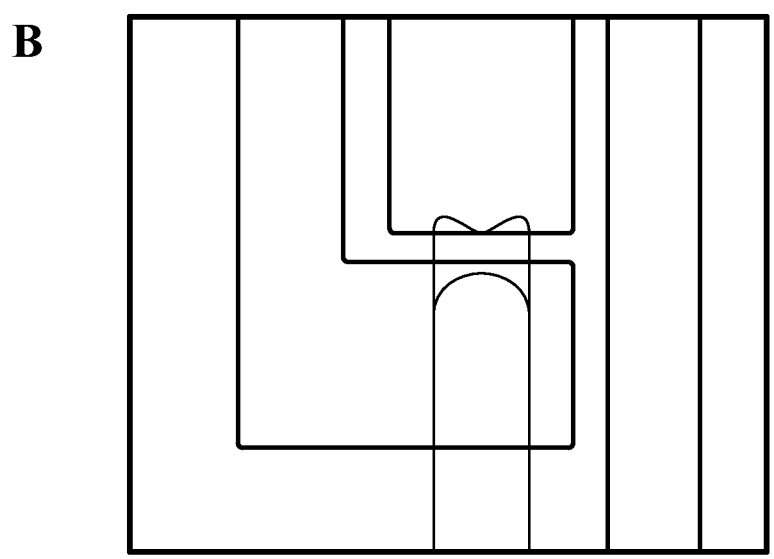

FIG. 25 shows a cell capture chamber with a downstream sieve valve. Functionalized beads (e.g. functionalized with oligo-dTs) are stacked against the sieve valves under flow pressure (FIG. 25, panel B), and then a single cell (or predetermined number of cells) is added to the chamber by deterministic cell loading, in which fluid routing through the use of valves can be used to isolate single cells from a bulk sample, or the use of cell traps as described above (FIG. 25, panel A). Cells may be immobilized at each directed location by a hydrodynamic cell trap or by a leaky 'sieve' valve. By flowing a chemical lysis reagent through the chamber, the cell is lysed, and the substrate (e.g. mRNA) is captured and purified on the beads. Subsequent reagents may be flowed through the reaction chamber while keeping the substrate-bound beads immobilized by the sieve valve. The chamber may be sealed by (non-leaky) valves to carry out each reaction step.

TABLE 4

Results from Illumina sequencing of single-cell, whole transcriptomes (no randomers) using a microfluidic chip.

| Description | Total reads | Total Gbp | Aligned reads | % Aligned | % Dups total | Genes detected | Genes detected at >=2 reads | Genes detected at >=10 reads | Coverage 5'/3' |
|---|---|---|---|---|---|---|---|---|---|
| Single Cell 1 | 14341272 | 0.64 | 10336447 | 72.1 | 91.8 | 1603 | 1304 | 668 | 86.7 |
| Single Cell 2 | 14916262 | 0.66 | 9171788 | 61.5 | 74.7 | 2719 | 2443 | 1864 | 14.9 |
| Single Cell 3 | 12994578 | 0.57 | 9154643 | 70.4 | 71.9 | 2197 | 1904 | 1271 | 42.9 |
| No Cell Cont. 1 | 14426522 | 0.64 | 9372123 | 65 | 94 | 1494 | 1185 | 582 | 43.4 |
| No Cell Cont. 2 | 16101806 | 0.71 | 10098883 | 62.7 | 94.5 | 6150 | 3283 | 528 | 15.9 |

Example 6

Figure 26:
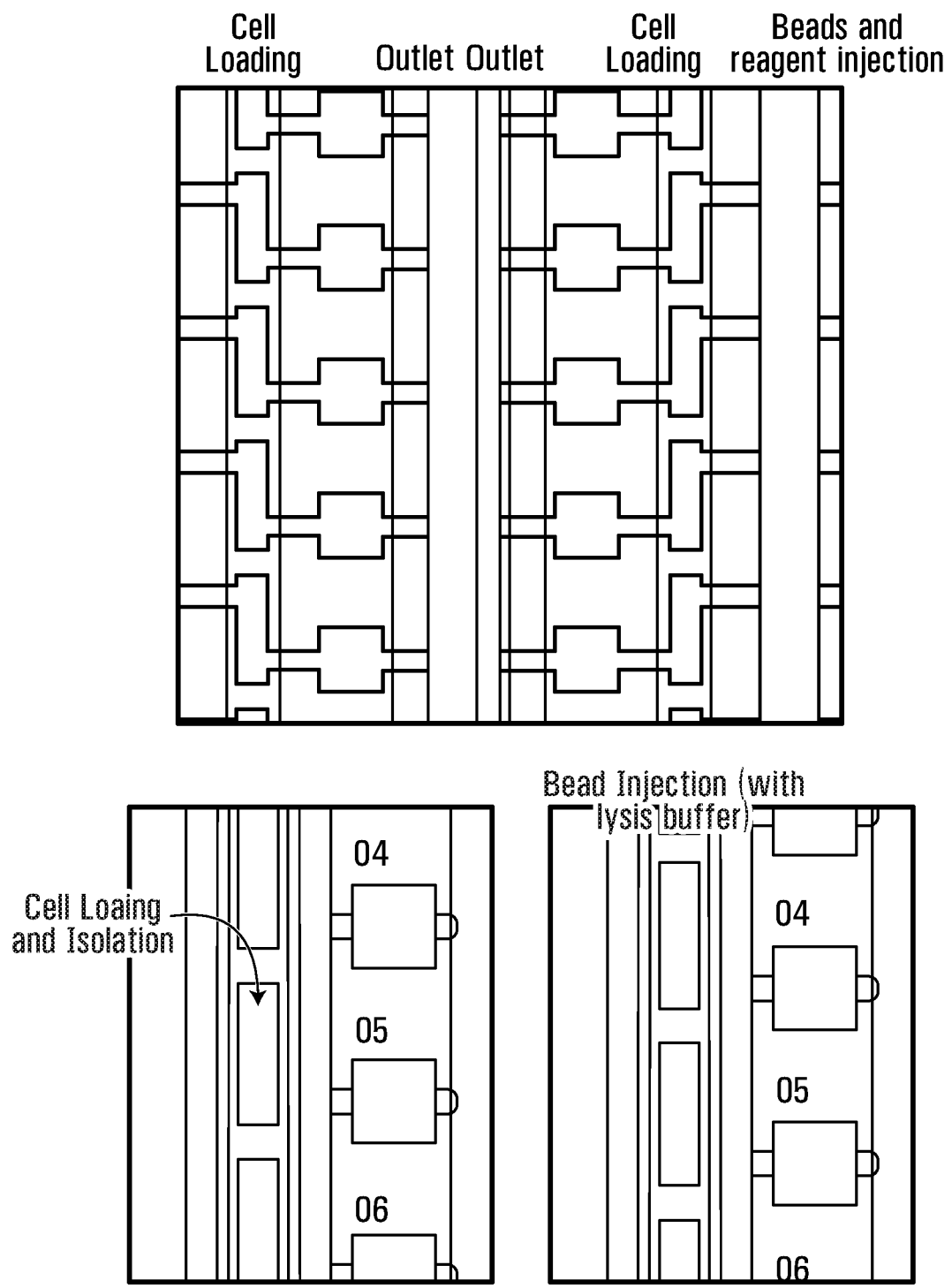
FIG. 26 is an of a microfluidic device for magnetic immobilization of functionalized beads to bind template (DNA/RNA) and enable multi-step reactions in a single chamber according to an embodiment of the invention.

FIG. 26 illustrates a microfluidic device for magnetic immobilization of functionalized beads to facilitate multi-step reactions in a single chamber. Cells are isolated in capture chambers adjacent to larger reaction chambers. Functionalized magnetic beads, e.g. with poly-T oligonucleotides, are suspended in lysis reagent and then injected through cell capture chamber and into a reaction chamber, lysing the cell(s) in the process. After binding substrate (e.g. mRNA), the beads are immobilized at the top of the chamber (or any suitable wall of the chamber) by a magnetic field, thereby allowing the fluidic contents of the reaction chamber to be replaced. This allows for substrate purification and multi-step processing of the bound substrate within a single chamber.

Example 7

Figure 27:
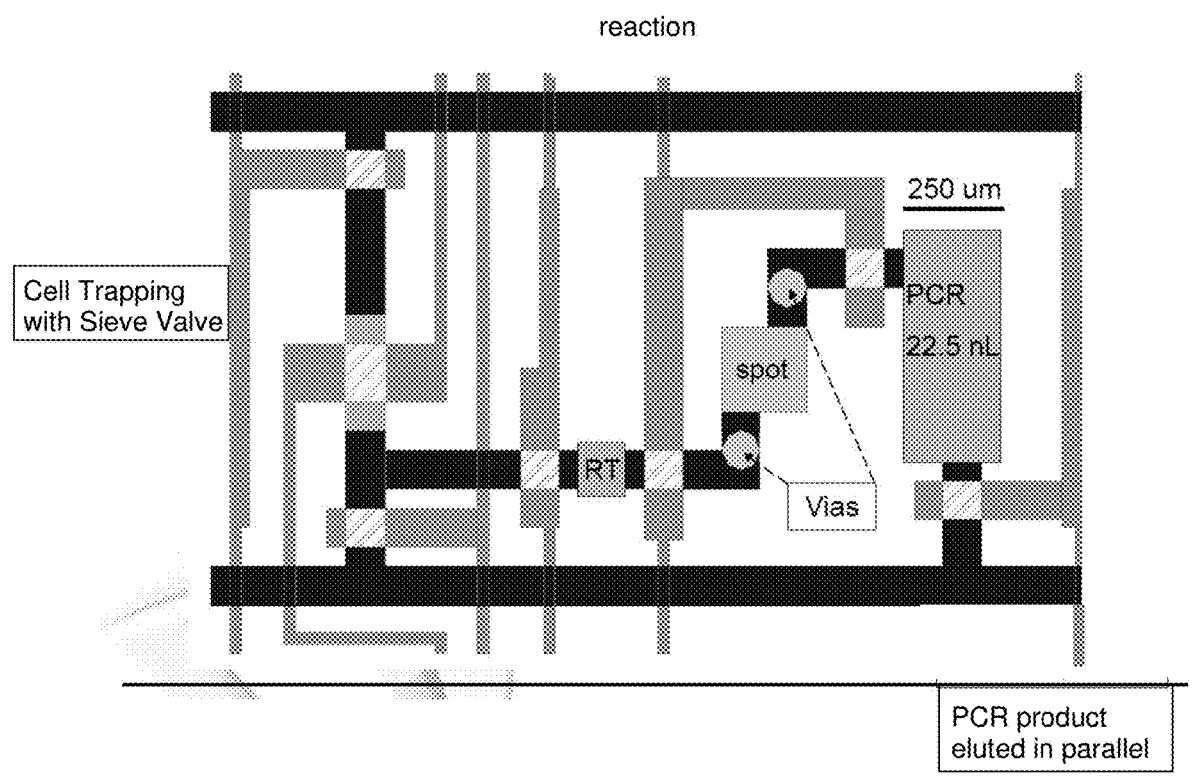
FIG. 27 is a schematic diagram of a microfluidic device integrating single cell processing with microarray spotting to address different reagents to different reactions.

FIG. 27 is a schematic diagram of a microfluidic device integrating single cell processing with microarray spotting to address different reagents (i.e. primers/probes) to different reactions according to one embodiment of the invention. In this a captured cell is heat lysed, and the cell lysate is then pushed with each subsequent reagent into the adjacent chambers (e.g., for reverse transcription (RT), and PCR). The reaction products are recoverable through an outlet in the chamber. In this design a laser may be used to ablate fluidic vias (interconnects) down to chambers aligned over an array of spotted reagents. Using a robotic microarray spotter, these spots can be used to provide each reaction with a different primer or probe. Primers may be spotted with a unique identifying sequence of DNA bases. This "barcode" is incorporated in each single cell reaction and facilitates DNA and/or RNA transcript sequencing of many single cells in parallel, with the cell of origin for each sequence encoded in the barcode.

Example 8

Figure 28:
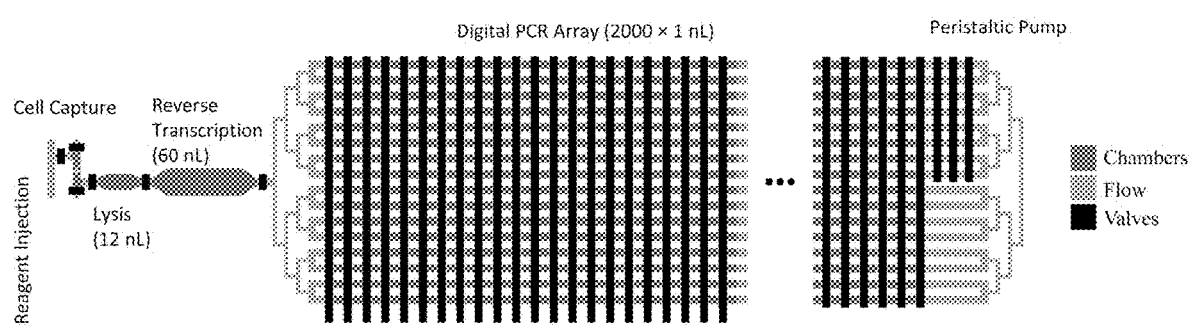
FIG. 28 is a schematic diagram of a microfluidic device for integrated single cell digital PCR according to one embodiment of the invention.
Figure 29:
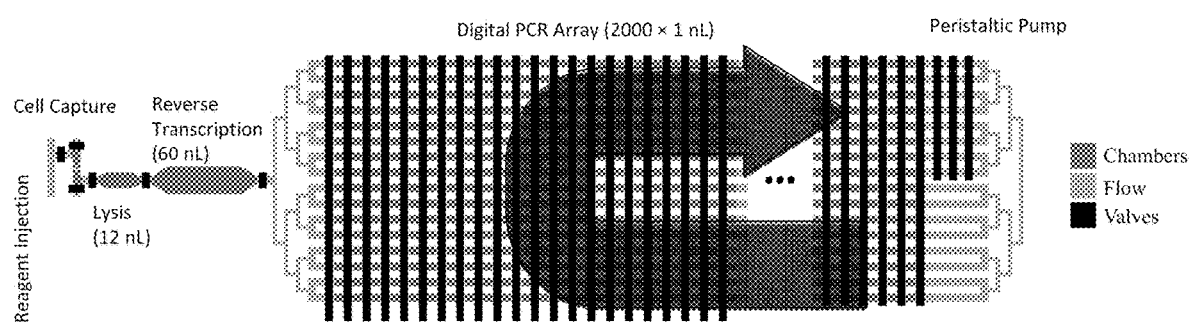
FIG. 29 is a schematic diagram of the microfluidic device of FIG. 28, depicting the mixing of the PCR solution and template molecules by a bifurcating rotary mixer.

A microfluidic device for integrated single cell digital PCR according to one embodiment of the invention is show in FIG. 28. This device cam perform all fluid handling steps for parallel single molecule amplification and counting of RNA transcripts from single cells. The device combines the cell processing presented in Example 2 with an array of 2000×1 nL chambers for digital PCR. Cells are captured by prior to being washed and lysed. The contents are passed to adjacent, larger chambers for reverse transcription. Finally, the DNA template (RT product) is pushed into the array of digital PCR chambers with PCR reagent. To mix the PCR solution and template molecules, the digital array was designed as a large bifurcating rotary mixer where the fluid revolves around the array by the use of a peristaltic pump (FIG. 29). After mixing, valves (in red) partition the lanes into 2000 reaction chambers. Digital PCR is performed, and the number of wells with amplification are counted to directly count single molecules from sample, i.e. single cell. This strategy, when combined with high-density digital PCR arrays, enables the high-throughput analysis of single cells by digital PCR with excellent efficiency in the transfer of cell-derived nucleic acids into the digital array; this is difficult to achieve if cells are processed in tubes and then transferred to a device for digital PCR analysis. It should be appreciated that this geometry may be used along with a chemical or enzymatic DNA fragmentation step to do digital PCR analysis on genomic DNA and that this may find applications in the analysis of copy number variations from single cells.

Example 9

Figure 30:
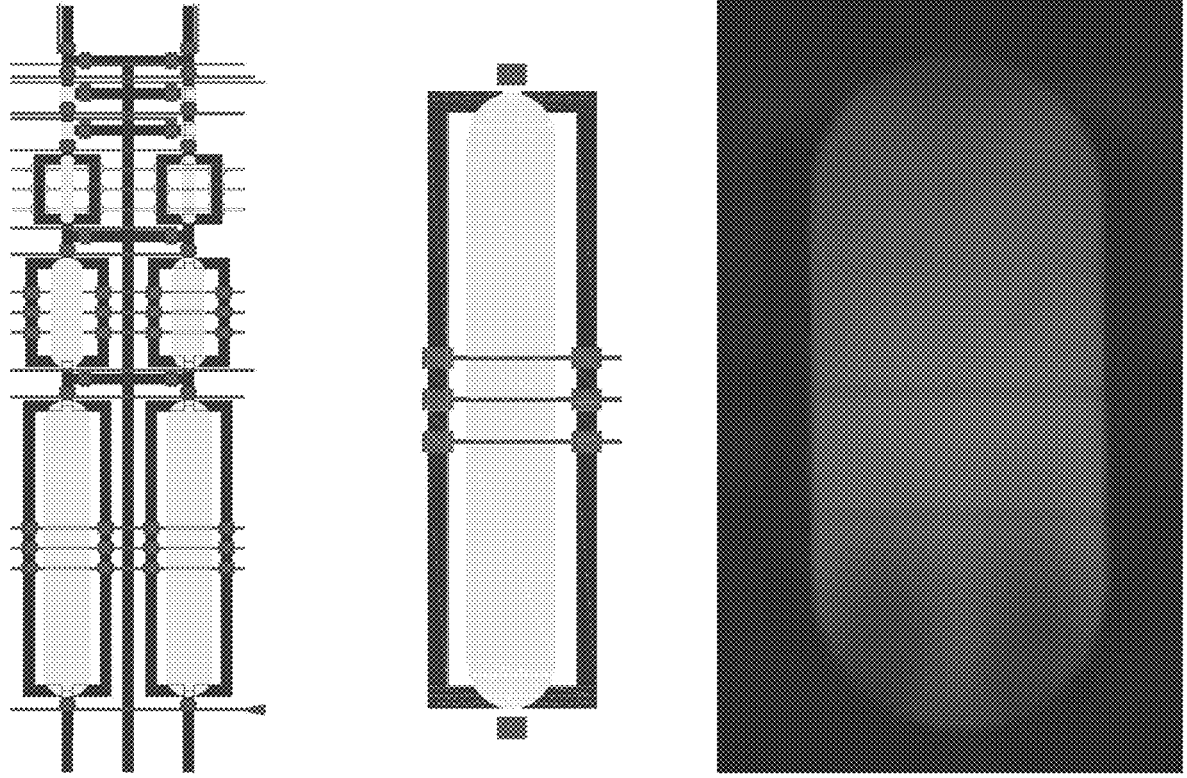
FIG. 30 is a schematic diagram of a microfluidic device for sequentially diluting cell products by passing them to larger chambers according to one embodiment of the invention

A microfluidic device for sequentially diluting cell products by passing them to larger chambers according to one embodiment of the invention, that may or may not include active mixing, is shown in FIG. 30. Seven sequential chambers are shown. Reagents are pushed from one chamber to the next by dilution with a subsequent reagent. Previous chambers can also be bypassed or flushed. Active mixing is used to increase the speed of mixing in large chambers. The right panel is a fluorescence image of active mixing by using valves as peristaltic pump in channels around outside of chamber to circulate solution. This design is optimized for multistep reactions such as described by Tang et al. (80) for the amplification of RNA from single cells to generate sufficient material for sequencing. For instance, multiple steps, including cell capture, cell lysis, cDNA synthesis, EXO1 degradation of primers, poly-A tailing, second strand synthesis, and PCR, can be executed by sequential transfer of cell contents between chambers. It should be noted here that each subsequent chamber provides a 3:1 dilution in order to achieve efficient transfer of contents at each step, and that this requires that the concentration of reagents at each step be chosen appropriately. Further, it should be appreciated that different dilution ratios are possible and may be desirable.

Example 10 Spatial Multiplexing

Figure 31:
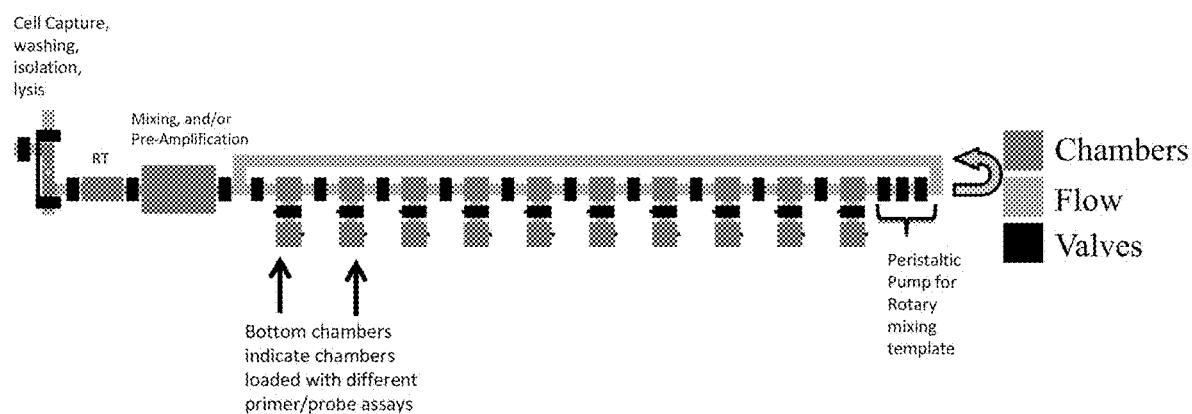
FIG. 31 is a schematic diagram of a microfluidic device for multiplexed single cell RT-qPCR according to one embodiment of the invention.

In yet another embodiment of the invention, cell lysate may be split into multiple chambers for parallel performance of different assays. FIG. 31 presents a microfluidic device for (low) special multiplexing according to one embodiment of the invention. Spatial multiplexing allows multiple assays to be spatially defined, and removes the optical limitations The device features cell processing units as described in Example 2, wherein a single cell is hydrodynamically trapped, washed and lysed. The lysate (DNA, RNA, or template) is transferred to the adjacent chamber by pushing with reverse transcription (RT) reagent. After RT, the product (cDNA) may be sequentially transferred and processed to multiple adjacent chambers. In FIG. 31 (below), a single larger chamber is illustrated that could be used for mixing the template and PCR solution by diffusion, and/or for pre-amplification of the template by PCR.

For multiplexing the template is pushed (with PCR reagent) down a channel with multiple (e.g. 10) chambers. The channel loops back onto itself, and template and reagents may be mixed by a rotary mixer. After mixing, the channel is partitioned into individual chambers. Different assays (i.e. primers/probes) are loaded into adjacent chambers (fluid routing facilitated by laser ablated inter-layer connections). The valve separating the combined PCR/template solution and the primer/probe assays is opened and the contents are allowed to mix by diffusion (an alternative design could combine these two solutions by advection). In this way, the contents of a single cell can be interrogated for multiple targets (i.e. different transcripts).

Example 11

In yet another embodiment of the invention, a microfluidic device could be used to treat single cells (or a pre-determined number of cells) prior to analysis. For example, immobilized cells can be stimulated in any number of ways (e.g. by chemicals, pathogens, electricity, etc.) and lysed, with lysates transferred to reaction chambers for analysis. For example, cells positioned in traps could be subjected to stimulation by signaling molecules included during the wash step. Following a defined amounts of time, potentially varied for different cells, the cells may then be lysed and the contents transferred to auxiliary chambers for the amplification and/or quantification of nucleic acids by RT-qPCR, digital PCR, sequencing, microarray analysis, and so forth. This would be useful for studying the early transcriptional events that result from stimulation with single cell precision, temporal resolution and throughput that is not possible using alternative methods.

A person skilled in the art will further understand that the method need not be destructive. For example, immobilized cells can be stimulated, and subsequent cell secretions could be washed to downstream reaction chambers for analysis. The intact cells could then be subjected to further treatment or recovered for culturing. Such secretions could include metabolites, hormones, cytokines, other proteins, miRNA, mRNA, and so forth. As an example of this the secreted proteins from a cell could be quantified using a fluorescent sandwich assay in which antibodies are used to capture and detect the protein of interest on a solid surface such as the channel walls or an immobilized microbead. Alternatively, secreted proteins could be detected using immuno PCR approaches with qPCR performed in a downstream chamber. Alternatively digital protein counting could be performed using enzymatic amplification and detection through cleavage of a fluorescent substrate or by performing digital immuno PCR wherein fewer than one protein is present in each of an array of downstream reactors. It should be appreciated by those skilled in the art that there are many possible assays that can be performed on DNA, RNA, proteins, and metabolites secreted from single cells.

Example 12

In another embodiment of the invention, microfluidic devices can be used to isolate cells for culture analysis under flow. In particular, if the traps are highly efficient and can only contain a single cell, then an array of traps in a channel could be used to sequentially catch the progeny of a cell (thereby allowing for lineage analysis). Such embodiments are of utility in the study of asymmetric division of stem cells where the progeny of a cell may be programmed to a differentiation state that is not identical to the cell of origin. For instance, the positioning of a single cell at the start of an array of traps could be used, through cell division, to populate the remaining traps in the array. The cells could then be individually processed to amplify and quantify mRNA or miRNA expression and thereby obtain information regarding the transcriptional state of stem cells and their progeny under defined conditions.

Example 13

In yet another embodiment of the invention, a microfluidic device could be used to trap and immobilize cells to improve transfection. In such an embodiment rare cell types could be immobilized and exposed to the flow of a solution of viruses to increase the efficiency of cell-virus interaction. In one scenario the cells could be positioned downstream of other cells that produce the virus of interest.

Example 14

In yet another embodiment of the invention, cell traps may be used to fix and stain cells, either pre- or post-lysis, including antibody staining, mRNA FISH, FISH, or chemical staining.

Example 15

In yet another embodiment of the invention, the cell corpse may be retained within a trap after lysis while cell contents are passed to downstream chambers, thereby enabling process of both DNA and other contents (e.g. RNA or protein) separately. For instance, chemical lysis with the detergent NP40 is known to leave the nucleus of cells intact. Alternatively, heat lysis may be used to disrupt the membrane, releasing cytosolic components, while preserving the localization of the genomic DNA.

Operation

While specific embodiments of the invention have been described and illustrated, such embodiments should be considered illustrative of the invention only and not as limiting the invention as construed in accordance with the accompanying claims.

REFERENCES

1. Taniguchi K, Kajiyama T, & Kambara H (2009) Quantitative analysis of gene expression in a single cell by qPCR. Nat Methods 6(7):503-506.
2. Warren L, Bryder D, Weissman I L, & Quake S R (2006) Transcription factor profiling in individual hematopoietic progenitors by digital RT-PCR. Proc Natl Acad Sci USA 103(47):17807-17812.
3. Raj A, van den Bogaard P, Rifkin S A, van Oudenaarden A, & Tyagi S (2008) Imaging individual mRNA molecules using multiple singly labeled probes. Nature Methods 5(10):877-879.
4. Larsson C, Grundberg I, Soderberg O, & Nilsson M (2010) In situ detection and genotyping of individual mRNA molecules. Nature Methods 7(5):395-U381.
5. Tang F, et al. (2009) mRNA-Seq whole-transcriptome analysis of a single cell. Nat Methods 6(5):377-382.
6. Bengtsson M, Hemberg M, Rorsman P, & Stahlberg A (2008) Quantification of mRNA in single cells and modelling of RT-qPCR induced noise. BMC Mol Biol 9:63.
7. Zare R N & Kim S (2010) Microfluidic platforms for single-cell analysis. Annu Rev Biomed Eng 12:187-201.
8. Sims C E & Allbritton N L (2007) Analysis of single mammalian cells on-chip. Lab Chip 7(4):423-440.
9. Wheeler A R, et al. (2003) Microfluidic device for single-cell analysis. Anal Chem 75(14):3581-3586.
10. Skelley A M, Kirak O, Suh H, Jaenisch R, & Voldman J (2009) Microfluidic control of cell pairing and fusion. Nat Methods 6(2):147-152.
11. Marcus J S, Anderson W F, & Quake S R (2006) Microfluidic single-cell mRNA isolation and analysis. Anal Chem 78(9):3084-3089.
12. Bontoux N, et al. (2008) Integrating whole transcriptome assays on a lab-on-a-chip for single cell gene profiling. Lab on a Chip 8(3):443-450.
13. Zhong J F, et al. (2008) A microfluidic processor for gene expression profiling of single human embryonic stem cells. Lab Chip 8(1):68-74.
14. Guo G J, et al. (2010) Resolution of Cell Fate Decisions Revealed by Single-Cell Gene Expression Analysis from Zygote to Blastocyst. Developmental Cell 18(4):675-685.
15. Petriv O I, et al. (2010) Comprehensive microRNA expression profiling of the hematopoietic hierarchy. Proc Natl Acad Sci USA 107(35):15443-15448.
16. Diehn M, et al. (2009) Association of reactive oxygen species levels and radioresistance in cancer stem cells. Nature 458(7239):780-783.
17. Toriello N M, et al. (2008) Integrated microfluidic bioprocessor for single-cell gene expression analysis. Proc Natl Acad Sci USA 105(51):20173-20178.
18 Rieseberg, M., Kasper, C., Reardon, K. & T, S. Flow cytometry in biotechnology. Applied Microbiology and Biotechnology 56, 350-360 (2001).
19 Cohen, D. et al. Chemical Cytometry: Fluorescence-Based Single-Cell Analysis. Annual Review of Analytical Chemistry 1, 165-190, doi:doi:10.1146/annurev.anchem.1.031207.113104 (2008).
20 Veening, J.-W., Smits, W. K., Hamoen, L. W. & Kuipers, O. P. Single cell analysis of gene expression patterns of competence development and initiation of sporulation in <i>Bacillus subtilis</i> grown on chemically defined media. Journal of Applied Microbiology 101, 531-541 (2006).
21 Kato, Y. et al. Real-time functional imaging for monitoring miR-133 during myogenic differentiation. The International Journal of Biochemistry & Cell Biology 41, 2225-2231, doi:DOI: 10.1016/j.biocel.2009.04.018 (2009).
22 Zhang, L. et al. Whole genome amplification from a single cell: implications for genetic analysis. Proc. Natl. Acad. Sci. U.S.A 89, 5847-5851 (1992).
23 Emmert-Buck, M. R. et al. Laser Capture Microdissection. SCIENCE 274, 998-1001, doi:10.1126/science.274.5289.998 (1996).
24 Orba, Y. et al. Application of laser capture microdissection to cytologic specimens for the detection of immunoglobulin heavy chain gene rearrangement in patients with malignant lymphoma. Cancer Cytopathology 99, 198-204 (2003).
25 Stich, M. et al. Live Cell Catapulting and Recultivation. Pathology—Research and Practice 199, 405-409, doi: Doi: 10.1078/0344-0338-00437 (2003).
26 Li, P. C. H., Camprieu, L. d., Cai, J. & Sangar, M. Transport, retention and fluorescent measurement of single biological cells studied in microfluidic chips. Lab on a Chip 4, 174-180 (2004).
27 Li, X. & Li, P. C. H. Microfluidic Selection and Retention of a Single Cardiac Myocyte, On-Chip Dye Loading, Cell Contraction by Chemical Stimulation, and Quantitative Fluorescent Analysis of Intracellular Calcium. Anal. Chem. 77, 4315-4322, doi:10.1021/ac048240a (2005).
28 Di Carlo, D., Aghdam, N. & Lee, L. P. Single-Cell Enzyme Concentrations, Kinetics, and Inhibition Analysis Using High-Density Hydrodynamic Cell Isolation Arrays. Anal. Chem. 78, 4925-4930, doi:10.1021/ac060541s (2006).
29 Rowat, A. C., Bird, J. C., Agresti, J. J., Rando, O. J. & Weitz, D. A. Tracking lineages of single cells in lines using a microfluidic device. Proceedings of the National Academy of Sciences 106, 18149-18154, doi:10.1073/pnas.0903163106 (2009).
30 Kobel, S., Valero, A., Latt, J., Renaud, P. & Lutolf, M. Optimization of microfluidic single cell trapping for long-term on-chip culture. Lab on a Chip 10, 857-863 (2010).
31 King, K. R. et al. A high-throughput microfluidic real-time gene expression living cell array. Lab on a Chip 7, 77-85 (2007).
32 Marcy, Y. et al. Dissecting biological "dark matter" with single-cell genetic analysis of rare and uncultivated TM7 microbes from the human mouth. Proc. Natl. Acad. Sci. U.S.A 104, 11889-11894 (2007).
33 Voldman, J., Gray, M. L., Toner, M. & Schmidt, M. A. A microfabrication-based dynamic array cytometer. Anal. Chem. 74, 3984-3990, doi:10.1021/ac0256235 (2002).
34 Braschler, T., Johann, R., Heule, M., Metref, L. & Renaud, P. Gentle cell trapping and release on a microfluidic chip by in situ alginate hydrogel formation. Lab on a Chip 5, 553-559 (2005).
35 Neuman, K. C., Chadd, E. H., Liou, G. F., Bergman, K. & Block, S. M. Characterization of photodamage to <i>Escherichia coli</i> in optical traps. Biophys. J. 77, 2856-2863 (1999).
36 Bartel, D. P. MicroRNAs: Genomics, Biogenesis, Mechanism, and Function. Cell 116, 281-297, doi:Doi: 10.1016/s0092-8674(04)00045-5 (2004).
37 O'Donnell, K. A., Wentzel, E. A., Zeller, K. I., Dang, C. V. & Mendell, J. T. c-Myc-regulated microRNAs modulate E2F1 expression. Nature 435, 839-843, doi:http://www.nature.com/nature/journal/v435/n7043/suppinfo/nature03677_S1.html (2005).
38 Chen, C.-Z., Li, L., Lodish, H. F. & Bartel, D. P. MicroRNAs Modulate Hematopoietic Lineage Differentiation. SCIENCE 303, 83-86, doi:10.1126/science.1091903 (2004).
39 Miska, E. et al. Microarray analysis of microRNA expression in the developing mammalian brain. Genome Biology 5, R68 (2004).
40 Sindelka, R., Jonak, J., Hands, R., Bustin, S. A. & Kubista, M. Intracellular expression profiles measured by real-time PCR tomography in the <i>Xenopus laevis</i> oocyte. Nucleic Acids Research 36, 387-392 (2008).
41 Chang, S., Johnston, R. J. & Hobert, O. A transcriptional regulatory cascade that controls left/right asymmetry in chemosensory neurons of C. elegans. Genes & Development 17, 2123-2137, doi:10.1101/gad.1117903 (2003).
42 Krichevsky, A. M., King, K. S., Donahue, C. P., Khrapko, K. & Kosik, K. S. A microRNA array reveals extensive regulation of microRNAs during brain development. RNA 9, 1274-1281, doi:10.1261/rna.5980303 (2003).
43 Niu, Q.-W. et al. Expression of artificial microRNAs in transgenic <i>Arabidopsis thaliana</i> confers virus resistance. Nat Biotech 24, 1420-1428, doi:http://www.nature.com/nbt/journal/v24/n11/suppinfo/nbt1255_S1.html (2006).
44 Scaria, V., Hariharan, M., Maiti, S., Pillai, B. & Brahmachari, S. Host-virus interaction: a new role for microRNAs. Retrovirology 3, 68 (2006).
45 Calin, G. A. et al. MicroRNA profiling reveals distinct signatures in B cell chronic lymphocytic leukemias. Proc. Natl. Acad. Sci. U.S.A 101, 11755-11760 (2004).
46 Cui, J.-W. et al. Retroviral insertional activation of the Fli-3 locus in erythroleukemias encoding a cluster of microRNAs that convert Epo-induced differentiation to proliferation. Blood 110, 2631-2640, doi:10.1182/blood-2006-10-053850 (2007).
47 Lu, J. et al. MicroRNA expression profiles classify human cancers. Nature 435, 834-838, doi:http://www.nature.com/nature/journal/v435/n7043/suppinfo/nature03702_S1.html (2005).
48 Ikeda, S. et al. Altered microRNA expression in human heart disease.
49 Physiol. Genomics 31, 367-373, doi:10.1152/physiolgenomics.00144.2007 (2007).
50 Thum, T., Catalucci, D. & Bauersachs, J. MicroRNAs: novel regulators in cardiac development and disease. Cardiovasc Res 79, 562-570, doi:10.1093/cvr/cvn137 (2008).
50 Thum, T. et al. MicroRNAs in the Human Heart: A Clue to Fetal Gene Reprogramming in Heart Failure. Circulation 116, 258-267, doi:10.1161/circulationaha.107.687947 (2007).
51 Wang, N., Zhou, Z., Liao, X. & Zhang, T. Role of microRNAs in cardiac hypertrophy and heart failure. IUBMB Life 61, 566-571 (2009).
52 Gibson, U. E., Heid, C. A. & Williams, P. M. A novel method for real time quantitative RT-PCR. Genome Research 6, 995-1001, doi:10.1101/gr.6.10.995 (1996).
53 Ginzinger, D. G. Gene quantification using real-time quantitative PCR: An emerging technology hits the mainstream. Experimental Hematology 30, 503-512, doi:Doi: 10.1016/s0301-472x(02)00806-8 (2002).

54 Nolan, T., Hands, R. E. & Bustin, S. A. Quantification of mRNA using real-time RT-PCR. Nat. Protocols 1, 1559-15382 (2006).
55 Bengtsson, M., Hemberg, M., Rorsman, P. & Stahlberg, A. Quantification of mRNA in single cells and modelling of RT-qPCR induced noise. Bmc Molecular Biology 9 (2008).
56 Taniguchi, K., Kajiyama, T. & Kambara, H. Quantitative analysis of gene expression in a single cell by qPCR. Nature Methods 6, 503-U550 (2009).
57 Tang, F. C., Hajkova, P., Barton, S. C., Lao, K. Q. & Surani, M. A. MicroRNA expression profiling of single whole embryonic stem cells. Nucleic Acids Research 34 (2006).
58 Tang, F. C. et al. 220-plex microRNA expression profile of a single cell. Nature Protocols 1, 1154-1159 (2006).
59 Kamme, F. et al. Single-Cell Microarray Analysis in Hippocampus CA1: Demonstration and Validation of Cellular Heterogeneity. J. Neurosci. 23, 3607-3615 (2003).
60 Kloosterman, W. P., Wienholds, E., de Bruijn, E., Kauppinen, S. & Plasterk, R. H. A. In situ detection of miRNAs in animal embryos using LNA-modified oligonucleotide probes. Nat Meth 3, 27-29, doi:http://www.nature.com/nmeth/journal/v3/n1/suppinfo/nmeth843_S1.html (2006).
61 Lu, J. & Tsourkas, A. Imaging individual microRNAs in single mammalian cells in situ. Nucleic Acids Research 37 (2009).
62 Neely, L. A. et al. A single-molecule method for the quantitation of microRNA gene expression. Nat Meth 3, 41-46,
63 Unger, M. A. et al. Microfabricated Elastomeric Valve and Pump Systems USA patent (2005).
64 Lee, R. C., Feinbaum, R. L. & Ambros, V. The *C. elegans* heterochronic gene lin-4 encodes small RNAs with antisense complementarity to lin-14. Cell 75, 843-854, doi: Doi: 10.1016/0092-8674(93)90529-y (1993).
65 Nelson, P. T. et al. Microarray-based, high-throughput gene expression profiling of microRNAs. Nat Meth 1, 155-161, doi:http://www.nature.com/nmeth/journal/v1/n2/suppinfo/nmeth717_S1.html (2004).
66 Thomson, J. M., Parker, J., Perou, C. M. & Hammond, S. M. A custom microarray platform for analysis of microRNA gene expression. Nat Meth 1, 47-53, doi:http://www.nature.com/nmeth/journal/v1/n1/suppinfo/nmeth704_S1.html (2004).
67 Willenbrock, H. et al. Quantitative miRNA expression analysis: comparing microarrays with next-generation sequencing. RNA 15, 2028-2034, doi:doi: 10.1261/rna.1699809 (2009).
68 Chen, C. et al. Real-time quantification of microRNAs by stem-loop RT-PCR. Nucl. Acids Res. 33, e179-, doi: 10.1093/nar/gni178 (2005).
69 Livak, K. J., Flood, S. J., Marmaro, J., Giusti, W. & Deetz, K. Oligonucleotides with fluorescent dyes at opposite ends provide a quenched probe system useful for detecting PCR product and nucleic acid hybridization. Genome Research 4, 357-362 (1995).
70 Unger, M. A., Chou, H. P., Thorsen, T., Scherer, A. & Quake, S. R. Monolithic microfabricated valves and pumps by multilayer soft lithography. SCIENCE 288, 113-116 (2000).
71 Thorsen T, Maerkl S J, & Quake S R (2002) Microfluidic large-scale integration. Science 298(5593):580-584.
72 Warren L, Bryder D, Weissman I L, & Quake S R (2006) Transcription factor profiling in individual hematopoietic progenitors by digital RT-PCR. Proc Natl Acad Sci USA 103(47):17807-17812.
73 Shah S P, et al. (2009) Mutational evolution in a lobular breast tumour profiled at single nucleotide resolution. Nature 461(7265):809-813.
74 Schulze H G, et al. (2010) Assessing Differentiation Status of Human Embryonic Stem Cells Noninvasively Using Raman Microspectroscopy. Analytical Chemistry 82(12):5020-5027.
75 Adewumi O, et al. (2007) Characterization of human embryonic stem cell lines by the International Stem Cell Initiative. Nature Biotechnology 25(7):803-816.
76 Ludwig T E, et al. (2006) Feeder-independent culture of human embryonic stem cells. Nat Methods 3(8):637-646.
77. Lozzio B B, Lozzio C B, Bamberger E G, & Feliu A S (1981) A multipotential leukemia cell line (K-562) of human origin. Proc Soc Exp Biol Med 166(4):546-550.
78. Yuan J Y, et al. (2009) MicroRNA-223 reversibly regulates erythroid and megakaryocytic differentiation of K562 cells. J Cell Mol Med 13(11-12):4551-4559.
79. Landgraf P, et al. (2007) A mammalian microRNA expression atlas based on small RNA library sequencing. Cell 129(7):1401-1414.
80. Tang F C, Barbacioru C, Nordman E, Li B, Xu N L, Bashkirov V I, Lao K Q, Surani M A: RNA-Seq analysis to capture the transcriptome landscape of a single cell. Nature Protocols 5:516-535.

What is claimed is:

1. A microfluidic device comprising:
a cell capture chamber, the cell capture chamber comprising:
a first inlet for admitting flow of fluid into the cell capture chamber;
at least one mechanical cell funnel; and
a corresponding trap positioned generally downstream from each of the at least one cell funnels, wherein each or a subset of the corresponding cell traps is a mechanical cell trap,
wherein each of the at least one mechanical cell funnels is operable to direct flow of fluid at the corresponding cell trap, and wherein each cell trap is positioned to receive a cell flowing in the fluid downstream from the cell funnel while permitting the fluid and additional cells therein to flow beyond and downstream of the cell trap.

2. The microfluidic device of claim 1, further comprising an auxiliary chamber, wherein the cell capture chamber comprises an outlet in fluid communication with the auxiliary chamber, wherein the outlet has an open and a closed position, wherein the open position allows for fluid to enter the auxiliary chamber from the cell capture chamber and the closed position prevents fluid flow into the auxiliary chamber from the cell capture chamber.

3. The microfluidic device of claim 1, wherein each or a subset of the at least one cell funnels comprises two or more nested funnel elements.

4. The microfluidic device of claim 1, wherein each or a subset of the at least one cell funnels is sized to permit passage of a single cell at a time.

5. The microfluidic device of claim 1, wherein each or a subset of the corresponding cell traps is sized to receive a single cell.

6. The microfluidic device of claim 1, further comprising a fluid injection channel in fluid communication with the cell capture chamber through a second inlet, wherein the second inlet has an open and a closed position, wherein the open position allows for fluid to enter the cell capture chamber from the fluid injection channel and in the closed position prevents fluid from flowing into the cell capture chamber from the fluid injection channel.

7. The microfluidic device of claim 1, further comprising a fluid injection channel in fluid communication with the cell capture chamber through the first inlet.

8. The microfluidic device of claim 1, further comprising a plurality of auxiliary chambers, wherein the plurality of auxiliary chambers comprises a first auxiliary chamber and a second auxiliary chamber,
wherein the cell capture chamber comprises an outlet in fluid communication with the first auxiliary chamber, wherein the outlet has an open and a closed position, wherein the open position allows for fluid to enter the first auxiliary chamber from the cell capture chamber and the closed position prevents fluid flow into the auxiliary chambers from the cell capture chamber, and
wherein the second auxiliary chamber is in fluid communication with the first auxiliary chamber through a first valve between the first and second auxiliary chambers, wherein the first valve has an open position to allow fluid flow from the first auxiliary chamber to the second auxiliary chamber and a closed position to prevent fluid flow from the first auxiliary chamber to the second auxiliary chamber.

9. The microfluidic device of claim 8, further comprising a third auxiliary chamber in fluid communication with the second auxiliary chamber and a second valve between the second and third auxiliary chambers, wherein the second valve has an open position to allow fluid flow from the second auxiliary chamber to the third auxiliary chamber and a closed position to prevent fluid flow from the second auxiliary chamber to the third auxiliary chamber.

10. The microfluidic device of claim 1, further comprising a plurality of auxiliary chambers, wherein the cell capture chamber further comprises a plurality of outlets, wherein each of the plurality of outlets is in fluid communication with a corresponding auxiliary chamber, wherein each outlet has an open and a closed position, wherein the open position allows for fluid to enter the corresponding auxiliary chamber from the cell capture chamber and the closed position prevents fluid flow into the corresponding auxiliary chamber from the cell capture chamber.

11. The microfluidic device of claim 1, wherein each of the at least one mechanical cell funnels or a subsect thereof comprises a pair of cell deflectors each having a proximal and a distal end, wherein the proximal ends are positioned at opposite sides of the capture chamber, and wherein each distal end of the cell deflector is angled on the diagonal in a downstream direction relative to the proximal ends, whereby the distal ends of the cell deflectors provide an opening sized to permit the passage of a cell between the distal ends of the cell deflectors.

12. The microfluidic device of claim 2, wherein the auxiliary chamber is expandable.

13. The microfluidic device of claim 8, wherein one or more of the plurality of auxiliary chambers is expandable.

14. The microfluidic device of claim 8, wherein the ratio between the second auxiliary chamber and the first auxiliary chamber is 5:1 by volume.

15. The microfluidic device of claim 1, wherein each cell trap or a subset thereof comprises a perforation for permitting fluid flow through the cell trap.

16. The microfluidic device of claim 12, wherein the ratio between the expanded auxiliary chamber and unexpanded auxiliary chamber is 5:1 by volume.

17. The microfluidic device of claim 2, wherein, when the outlet is in the open position, the cell capture chamber and the auxiliary chamber form a compound chamber.

18. The microfluidic device of claim 17, wherein the ratio between the cell capture chamber and the compound chamber is 1:5 by volume.

19. The microfluidic device of claim 10, wherein, when the outlets or a subset thereof are in the open position, the cell capture chamber and the auxiliary chambers corresponding to outlets in the open position form a compound chamber.

20. The microfluidic device of claim 17, wherein the ratio between the cell capture chamber and the compound chamber is 1:5 by volume.

21. The microfluidic device of claim 1, wherein the cell capture chamber is expandable.

22. The microfluidic device of claim 8, wherein, when the outlet is in the open position, and optionally the first valve is in the open position, the cell capture chamber and at least one of the plurality of auxiliary chambers form a compound chamber.

* * * * *